United States Patent [19]

Shutske et al.

[11] Patent Number: 4,673,746

[45] Date of Patent: Jun. 16, 1987

[54] 1,2-BENZISOXAZOLOXYACETIC ACIDS AND RELATED COMPOUNDS

[75] Inventors: Gregory M. Shutske, Nauheim, Fed. Rep. of Germany; Linda L. Setescak, Somerville; Richard C. Allen, Flemington, both of N.J.

[73] Assignee: Hoechst-Roussel Pharmaceuticals, Inc., Bridgewater, N.J.

[21] Appl. No.: 201,083

[22] Filed: Oct. 27, 1980

Related U.S. Application Data

[63] Continuation-in-part of Ser. No. 949,128, Oct. 6, 1978, abandoned, which is a continuation-in-part of Ser. No. 853,213, Nov. 21, 1977, abandoned.

[51] Int. Cl.$^4$ .................. C07D 261/20; C07D 275/04; A61K 31/42; A61K 31/425
[52] U.S. Cl. ..................................... 546/272; 546/274; 548/207; 548/241
[58] Field of Search ................ 548/241, 207; 546/272, 546/274

[56] References Cited

U.S. PATENT DOCUMENTS

| | | | |
|---|---|---|---|
| 3,352,877 | 11/1967 | Hollander | 260/296 |
| 3,642,897 | 2/1972 | Hardtmann | 260/570 |
| 3,652,575 | 3/1972 | Hutton et al. | 548/206 |
| 3,948,928 | 4/1976 | Nishimura et al. | 548/241 |
| 3,951,999 | 4/1976 | Saunders et al. | 548/241 |
| 4,085,114 | 4/1978 | Adachi et al. | 260/307 DA |
| 4,104,387 | 8/1978 | Wade et al. | 548/207 |
| 4,104,388 | 8/1978 | Wade et al. | 548/207 |
| 4,122,176 | 10/1978 | Katsube et al. | 424/250 |
| 4,174,442 | 11/1979 | Wade et al. | 548/207 |
| 4,217,349 | 8/1980 | Katsube et al. | 424/248.4 |

FOREIGN PATENT DOCUMENTS

| | | | |
|---|---|---|---|
| 1503 | 4/1979 | European Pat. Off. | 424/270 |
| 2450053 | 10/1973 | Fed. Rep. of Germany | 548/241 |
| 769318 | 12/1971 | France | 548/207 |
| 51-136666 | 11/1976 | Japan . | |
| 7808801 | 1/1979 | Netherlands | 424/270 |

OTHER PUBLICATIONS

Burger, Alfred, Medicinal Chemistry, 3rd Ed., p. 957 (1971).
Adachi, et al.; Chem. Abst. 87: 39460 (3, 1977).
Adachi, et al.; Chem. Abst. 90: 87436b (1978).
Uno, et al.; Chem. Abst. 87: 39459c (1976).
Cutter Labs., "Alkyl Esters of ... Indazol-3-yl Oxyacetic Acids," Chem. Abst. 75: 49074(q) (1971).
Yabuuchi et al., "(1-Benzyl-3-Indazolyl) Oxyacetic Acid," Chem. Abst. 82: 156290y (1974).
Wada et al., "Indazole-3-Acetic Acid Derivatives," Chem. Abst. 83: 10069(g).
Chem. Abstr. 83, 131575c (1975).
Derwent, S 1621 W/31 (1975).
Chem. Abstr. 58, 12568b (1963).
Derwent, 7752 (1963).
"Medicinal Chemistry", de Stevens (Ed.), vol. 11, "Drug Design, "Ariens, vol. 1, Academic Press, N.Y. (1971), pp. 241-253.
Friedman, 1st Symposium on Chemical-Biological Correlation, NRC, Natl. Acad. Sci, Publn. 20, pp. 296-358.
Burger's Medicinal Chemistry, 4th Edn., Part 1, Wolff (Ed.), John Wiley & Sons, N.Y. (1980), p. 6.

Primary Examiner—Donald G. Daus
Assistant Examiner—G. Hendricks
Attorney, Agent, or Firm—Curtis, Morris & Safford

[57] ABSTRACT

Novel 1,2-benzisoxazoloxyacetic acids and related compounds, methods for preparing same and methods of treatment by administering compositions containing such a compound are described. These compounds are useful as diuretic, uricosuric and antihypertensive agents.

114 Claims, No Drawings

1,2-BENZISOXAZOLOXYACETIC ACIDS AND RELATED COMPOUNDS

This is a continuation-in-part application of prior application Ser. No. 949,128, filed Oct. 6, 1978, which is a continuation-in-part application of original application Ser. No. 853,313, filed Nov. 21, 1977 both now abandoned.

This invention relates to novel 1,2-benzisoxazoloxyacetic acids and related compounds which are useful as diuretics, uricosurics, and antihypertensives, to methods of their preparation, to methods of treatment with pharmaceutically effective amounts thereof and to pharmaceutical compositions containing such a compound as an active ingredient.

To the best of our knowledge, the compounds of the present invention have not been heretofore made, described or suggested. Although 1,2-benzisoxazoles are known, none are known which suggest the instantly described compounds or their utility.

The compounds of this invention can be depicted by the general formula

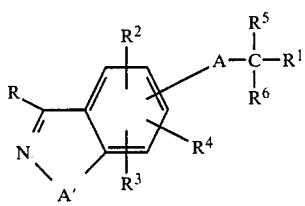

in which R is hydrogen, loweralkyl, loweralkenyl, loweralkynyl, cycloalkyl, cycloalkenyl, bycycloalkyl, tricycloalkyl, cycloalkylloweralkyl, cycloalkenyloweralkyl, naphthyl,

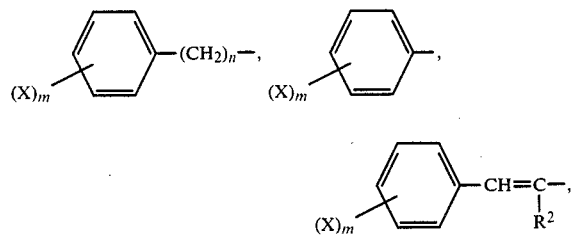

thienyl, furyl, pyrryl, pyridyl or pyridyl N-oxide; $R^1$ is a free or esterified carboxyl group of from 1 to 8 carbon atoms,

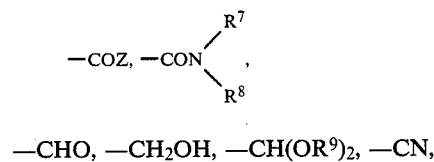

—CHO, —CH$_2$OH, —CH(OR$^9$)$_2$, —CN,

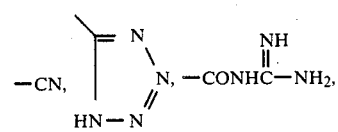

-continued

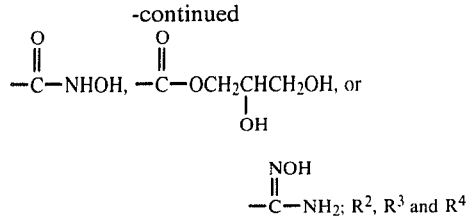

$R^2$, $R^3$ and $R^4$ are the same or different and each can be hydrogen, halogen or loweralkyl; X is hydrogen, halogen, loweralkyl, loweralkylthio, loweralkoxy, hydroxy, trifluoromethyl, nitro, amino or acylamino; $R^5$, $R^6$, $R^7$, $R^8$ and $R^9$ are the same or different and each can be hydrogen or loweralkyl; A and A' are the same or different and may be O or S; Z is chlorine, bromine or fluorine; and m and n are the same or different and each can be the integer 1, 2 or 3. Also included within the scope of the present invention are the physiologically acceptable salts of the above-depicted compounds which are capable of forming same.

Some compounds within the scope of this invention have greater pharmaceutical activity than others. Some of the latter, such as those in which $R^1$ is an esterified carboxyl group CN, CH$_2$OH or CHO are nevertheless desirable as intermediates for the preparation of the more active compounds. As indicated above, R may be a heterocyclic group such as thienyl, fury, pyrryl or pyridyl, as well as an aliphatic or carbocyclic group. A preferred group of compounds are those in which R is an aromatic ring having an ortho fluoro with respect to the position of attachment to the overall ring structure.

In the foregoing definitions and throughout this application the following terms have the following meanings.

"Thienyl, furyl, pyrryl or pyridyl" means unsubstituted and substituted moieties wherein the substituents are halogen or loweralkyl;

"lower" means from 1 to 4 carbon atoms;

"cycloalkyl" means a saturated carbocyclic ring of from 3 to 8 carbon atoms;

"bicyclo- and tricycloalkyl," respectively, mean bi- and tricarbocyclic ring systems containing from 7 to 10 carbon atoms; and "cycloalkenyl" means an unsaturated carbocyclic ring of from 5 to 8 carbon atoms.

The physiologically acceptable salts of this invention include those formed with an alkali or alkaline earth metal base or with a non-toxic organic base such as ethanolamine, diethanolamine or N-methylglucamine.

The compounds of the present invention can be prepared by one of the following multi-step sequences of reactions in which unless otherwise indicated R, $R^1$ through $R^8$, X, m and n are as previously defined and Y is chlorine or fluorine and ambient temperature means about 20°-25° C.

A. A phenol or alkoxybenzene of the formula

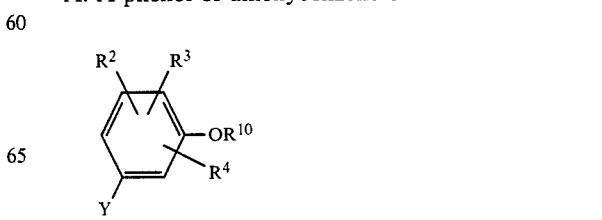

in which $R^{10}$ is hydrogen or loweralkyl, is reacted under Friedel-Crafts conditions with an acid halide of the formula

RCOZ in which R is as defined earlier and Z is chlorine, bromine or fluorine to provide a compound of the formula

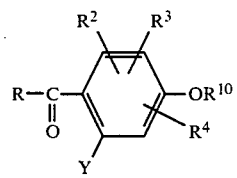
I

A preferred method involves the use of 1,2-dichloroethane as a solvent and aluminum chloride as the Friedel-Crafts catalyst.

B. A compound of the formula R-H in which R is

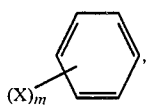

thienyl pyrryl or furyl is reacted under Friedel-Crafts conditions with an acid halide of the formula

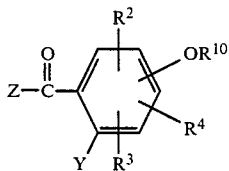

in which Y, Z and $R^{10}$ are as defined in sequence A, above, to provide a compound of the formula

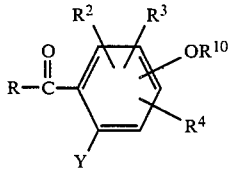
II

A preferred method involves use of 1,2-dichloroethane as a solvent and aluminum chloride as the Friedel-Crafts catalyst.

C. A compound of the formula

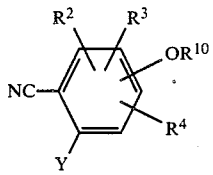

in which $R^{10}$ is loweralkyl is reacted with a compound of the formula R—MgZ or R—Li where R is not hydrogen followed by hydrolysis to afford a compound of Formula II.

Preferred conditions include use of tetrahydrofuran as solvent at a temperature of $-70°$ C. to ambient.

D. A compound of Formula II in which R is hydrogen and $R^{10}$ is loweralkyl is reacted according to Method C to provide a compound of the formula

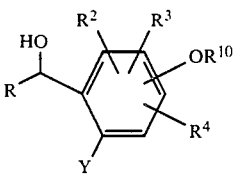

where R is not hydrogen.

E. A compound as prepared in Method D is oxidized to provide a compound of Formula II wherein R is not hydrogen. One such method involves use of chromium trioxide in glacial acetic acid.

F. A compound of Formula I or II in which $R^{10}$ is loweralkyl, can be dealkylated by methods known in he art to obtain the corresponding compound I or II in which $R^{10}$ is hydrogen. One such method involves treating with aluminum chloride in benzene.

G. A compound of Formula I or II is treated with hydroxylamine hydrochloride in a solvent such as pyridine to provide the corresponding compound of the formula

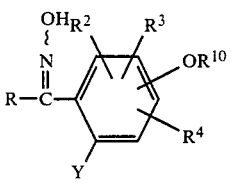
III

H. A compound of Formula III is cyclized by treatment with a base in the presence of a solvent at a temperature of from ambient to reflux of the reaction medium to provide the corresponding bicyclic compound of the formula

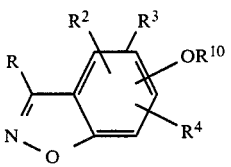
IV

A preferred method of cyclizing utilizes the base sodium hydride in the solvent dimethylformamide-benzene mixture at reflux.

I. A diphenol or dialkoxybenzene of the formula

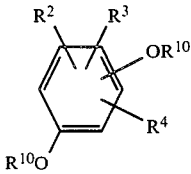

wherein $R^2$, $R^3$, $R^4$ and $R^{10}$ are as previously defined is reacted according to the procedure of Method A to provide a compound of the formula J. A compound of the formula R-H in which R is

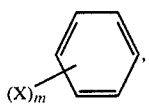

thienyl, pyrryl or furyl is reacted under Friedel-Crafts conditions with an acid halide of the formula

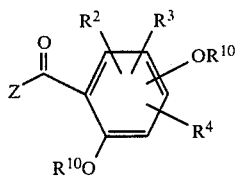

in which Z and $R^2$, $R^3$, $R^4$ and $R^{10}$ are as previously defined to provide a compound of the formula

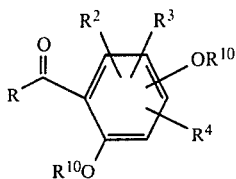

V

K. A compound of the formula

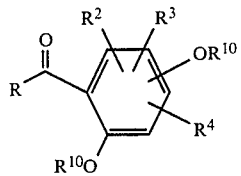

in which $R^{10}$ is loweralkyl is treated according to Method C to produce a corresponding compound of formula V.

L. A compound of Formula V wherein R is hydrogen and $R^{10}$ is loweralkyl is reacted according to Method C to provide a compound of the formula

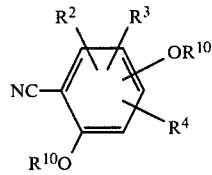

in which R is not hydrogen.

M. A compound as prepared in Method L is oxidized to provide a compound of formula V wherein R is not hydrogen. One such method involves the use of chromium trioxide in glacial acetic acid.

N. A compound of formula V in which $R^{10}$ is loweralkyl can be selectively dealkylated to provide the corresponding compound V in which $R^{10}$ ortho to the carbonyl group is hydrogen or fully dealkylated to provide a compound as depicted in formula V in which both $R^{10}$ groups are hydrogen. The former process can be effected by use of one equivalent of aluminum chloride, the latter by two equivalents, both processes occuring in such solvents as benzene.

O. A compound of formula V in which at least the $R^{10}$ which is ortho to the carbonyl group is hydrogen is treated according to the procedure of Method G to provide a compound of the formula

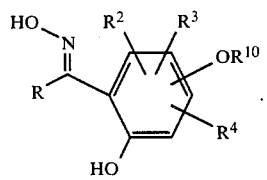

VI

P. A compound of formula VI is acetylated to provide a compound of the formula

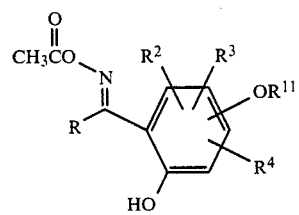

VII in which $R^{11}$ is hydrogen, loweralkyl or acetyl.

A preferred method utilizes acetic anhydride as a reactant and solvent.

Q. A compound of formula VII is cyclized by treatment with a base in the presence of a solvent at a temperature of from ambient to reflux of the reaction mixture to provide the corresponding bicyclic compound

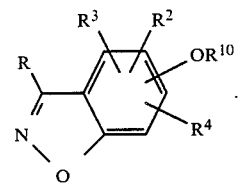

IV

R. A compound of formula IV in which $R^{10}$ is loweralkyl can be dealkylated to afford the corresponding compound in which $R^{10}$ is hydrogen. One preferred method is treatment with pyridine hydrochloride at 170°–200° C.

S. A compound of formula IV in which $R^{10}$ is hydrogen is reacted with a compound of the formula

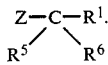

wherein $R^1$ is a free or esterified carboxyl group, CN, $CH_2OH$, $CH(OR^9)_2$ or $CO_2CH_2CH(OH)CH_2OH$ and $R^9$ is loweralkyl in the presence of a base and a solvent to provide a compound of the invention of the formula

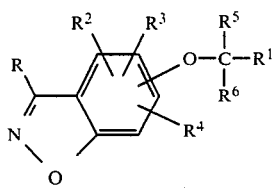

VIII with $R^1$ so defined. A preferred method utilizes sodium hydride as the base and dimethylformamide as the solvent.

T. A phenoxyalkanoic acid ester or nitrile of the formula

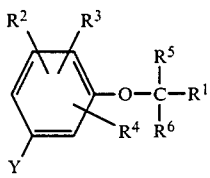

is treated according to the procedure of Method A to provide a compound of the formula

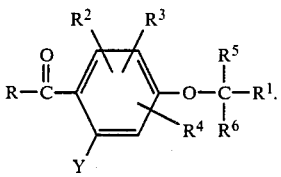

IX

A preferred method is carried out with an aluminum chloride catalyst and carbon disulfide solvent.

U. A compound of formula I or II wherein $R^{10}$ is hydrogen can be treated according to the procedure of Method S to provide a compound of the formula

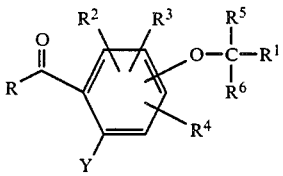

X in which $R^1$ is a free or esterified carboxyl group, CN, $CH_2OH$ or $CH(OH^9)_2$.

V. A compound of the formula IX or X can be treated according to the procedure of Method G to provide a compound of the formula

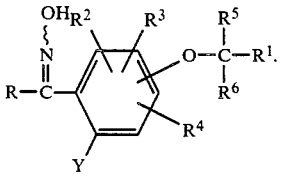

XI

W. A compound of Formula XI is treated according to the procedure of Method H to provide the corresponding compound of the invention of the formula VIII.

X. A compound of formula V in which $R^{10}$ is H is treated according to the procedure of Method S to provide a compound of the formula

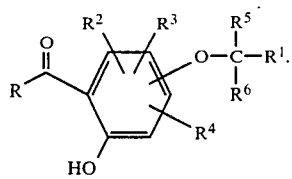

XII

Y. A compound of formula XII is treated according to the procedure of Method G to provide a compound of the formula

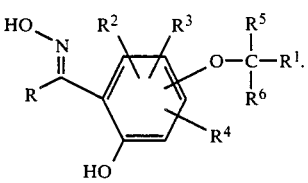

XIII

Z. A compound of formula XIII is treated according to the procedure of Method P to provide a compound of the formula

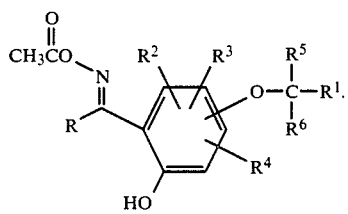

XIV

AA. A compound of the formula XIV is treated according to the procedure of Method Q to provide a compound of the invention VIII.

BB. A compound of the formula V, as prepared in Method N, in which R is hydrogen is treated with hydroxylamine-o-sulfonic acid in a solvent such a water to produce a compound of the formula IV.

CC. A compound of formula XII in which R is hydrogen is treated according to the procedure of Method BB to produce a compound of the invention VIII.

DD. A compound of formula IV in which $R^{10}$ is hydrogen and X is other than hydroxy or amino is treated with a dialkylthiocarbamoyl halide in the presence of a base to produce a compound of the formula

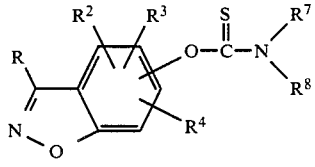

XV in which $R^7$ and $R^8$ are loweralkyl.

A preferred method involves the use of dimethylthiocarbamoyl chloride in dimethylformamide as a solvent and sodium hydride as the base.

EE. A compound of formula XV is thermally rearranged to a compound of the formula

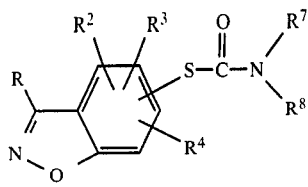
XVI by heating as a melt.

FF. A compound of the formula XVI is hydrolyzed by an convenient method known to the art to provide a compound of the formula

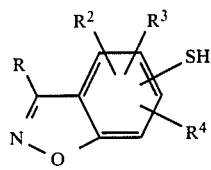
XVII

One such method utilizes dilute sodium hydroxide as the hydrolyzing agent.

GG. A compound of formula XVII is treated according to the procedure of Method S to produce a compound of the invention of formula

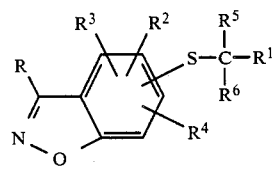
XVIII

HH. A compound of the formula

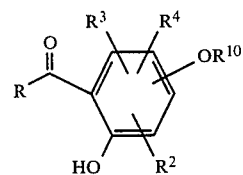

as described in Method N wherein $R^{10}$ is loweralkyl and X may not be amino or hydroxyl, is treated successively according to the methods of DD, EE and FF to yield a compound of the formula

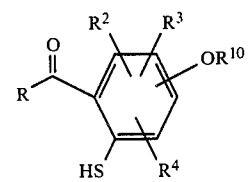
XIX

II. A compound of Formula XIX is treated successively according to Methods G, P. Q and R to yield a compound of the formula

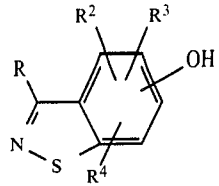
XX

JJ. A compound of formula XX is treated according to Method S to yield a compound of the invention

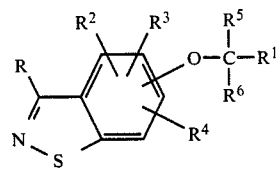
XXI

KK. A compound of formula XX is successively treated according to Methods DD, EE and FF to yield a compound of the formula

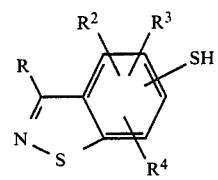
XXII

LL. A compound of formula XXII is treated according to Method S to yield a compound of the invention of the formula

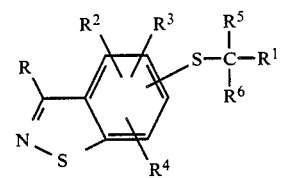
XXIII

MM. A compound of the invention of the formula VIII, XVIII, XXI or XXIII in which $R^1$ is a carboxylic acid ester or CN is readily converted to a corresponding compound in which $R^1$ is COOH.

One such suitable method is hydrolysis with a base such as sodium hydroxide.

NN. A compound of the invention of the formula VIII, XVIII, XXI or XXIII in which $R^1$ is $CH(OR^9)_2$ is readily converted to a corresponding compound in which $R^1$ is CHO.

One suitable method is hydrolysis with dilute mineral acid.

OO. A compound of the formula VIII in which X, $R^2$, $R^3$ and $R^4$ are not loweralkyl in which $R^1$ is $CH_2OH$ or as prepared in Method NN in which $R^1$ is CHO is converted to a corresponding compound in which $R^1$ is COOH.

A suitable method is oxidation with potassium permanganate

PP. A compound of the invention of the formula

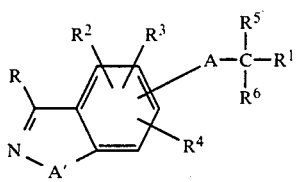

in which $R^1$ is COOH is readily converted to a compound in which $R^1$ is COZ. A suitable method is treatment with $SOZ_2$.

QQ. A compound of the formula

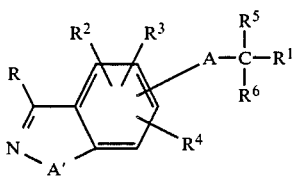

in which $R^1$ is COZ is readily converted to the corresponding compound in which $R^1$ is

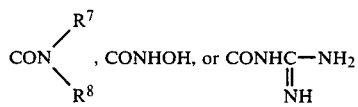

via treatment respectively with

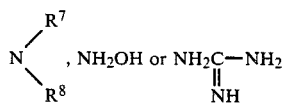

in the presence or absence of an acid scavenger.

RR. A compound of the invention of the formula

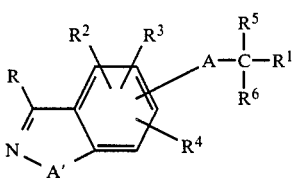

in which $R^1$ is CN is readily converted to the corresponding compound in which $R^1$ is

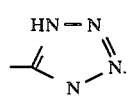

A suitable method is the treatment with $HN_3$ in dimethylformamide.

SS. A compound of the formula

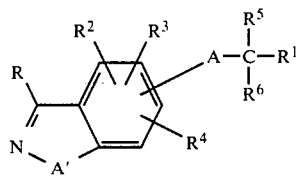

in which $R^1$ is COZ,

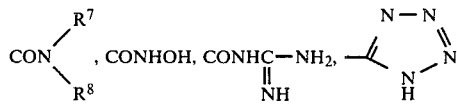

or any other non-specifically defined group which is convertible by a hydrolytic procedure to a COOH group is converted to a compound of the invention in which $R^1$ is COOH via acid or basic hydrolysis.

TT. A compound of the formula

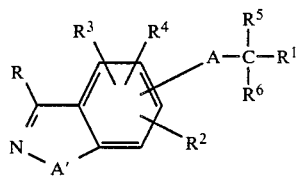

in which $R^1$ is COOH may be converted to a salt via treatment in a suitable solvent with an appropriate organic or alkali/alkaline earth base.

UU. A compound of the formula

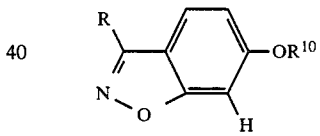

in which R is

$R^{10}$ is loweralkyl and X is not hydroxy or amino is treated with a strong base followed by a suitable electrophile to provide a compound of the formula

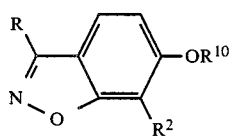

in which $R^2$ is halogen or loweralkyl. A preferred base is n-butyllithium and preferred electrophiles include bromine, iodine, chlorine, N-halosuccinimides and alkylhalides.

VV. A compound of the formula

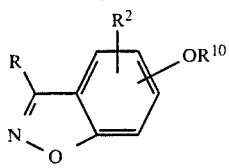

in which $R^2$ is hydrogen or halogen, $R^{10}$ is hydrogen or loweralkyl, R is

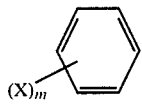

and X is halogen is treated with elemental halogen in a solvent such as acetic acid to provide a compound of the formula

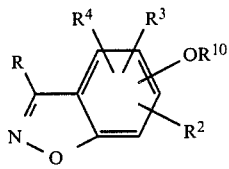

wherein $R^3$ and $R^4$ or both may be halogen. WW. A compound of the invention of the formula

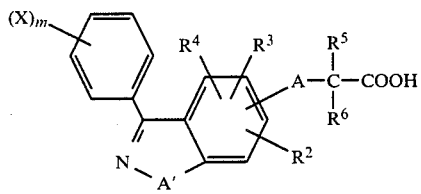

in which m is 1 or 2 and X is not $NO_2$ is nitrated via treatment with nitric acid in glacial acetic acid to provide the corresponding compound of the formula

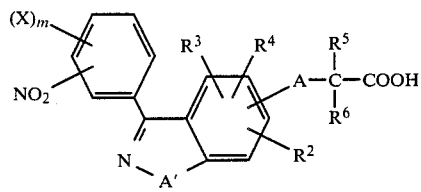

XX. A compound of the invention of the formula

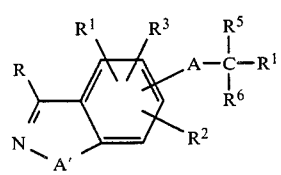

in which R is

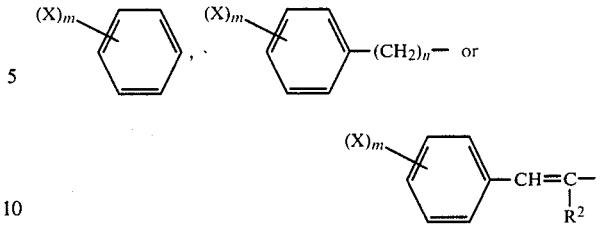

and X is alkoxy is dealkylated to provide a corresponding compound of the invention in which X is hydroxy. A method is the careful treatment with boron tribromide.

YY. A compound as described for the starting material of Method XX, above, except that X is nitro and may be reduced by any convenient method known to the art to provide the corresponding compound in which X is amino. A method involves the use of iron filings in aqueous ethanolic hydrochloric acid.

ZZ. A compound as described for the starting material of Method XX, above, except that X is amino and may be acylated by methods known to the art to provide the corresponding compound of the invention in which X is acylamino. A suitable method is acylation with an anhydride.

AAA. A compound formula IV in which R is pyridyl is treated with an oxidizing agent to provide a corresponding compound of formula IV in which R is

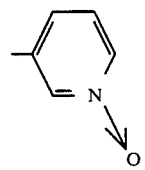

One such suitable oxidizing agent is 3-chloroperbenzoic acid.

BBB. A compound of formula VIII wherein $R^1$ is CN and R, $R^2$, $R^3$, $R^4$, $R^5$ and $R^6$ are as hereinbefore is reacted with a hydroxylamine hydrohalide in the presence of a base and a solvent to provide a compound of the formula

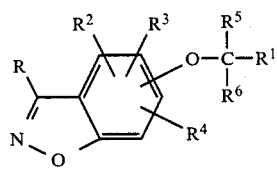

wherein $R^1$ is

and R, $R^2$, $R^3$, $R^4$, $R^5$ and $R^6$ are as above.

It can be appreciated that reaction times and exact reaction conditions of any and all of the above reaction steps of the above-shown sequences of reactions are dependent upon particular reactants and solvents involved.

All starting materials shown above are either known compounds or can easily be prepared by routine methods known to the art from readily available materials.

For example, a starting material applicable in sequence B, D, E, L and M to produce a compound of the invention wherein the O—CH$_2$—R$^1$ group occupies the 5-position in 2-chloro-5-methoxybenzoic acid. Such a material can be prepared from the readily available 2-chloro-5-nitroaniline via procedures readily known to one skilled in the art, e.g., diazotization and treatment with CuCN to afford 2-chloro-5-nitrobenzonitrile; followed by reduction with iron filings in aqueous ethanolic hydrochloric acid to 5-amino-2-chlorobenzonitrile; followed by diazotization to give 2-chloro-5 hydroxybenzonitrile; followed by methylation with dimethylsulfate to give 2-chloro-5-methoxybenzonitrile; concluded with hydrolysis to 2-chloro-5-methoxybenzoic acid. It is readily apparent that other required substituted alkoxy-ortho-halbenzoic acids, alkoxy(hydroxy)ortho-alkoxy(hydroxy)benzoic acids, -aldehydes, and -nitriles, and various halo-alkoxy(hydroxy)-, and dialkoxy(hydroxy)-benzenes can be readily obtained by similar sequences or other common reactions shown to one skilled in the art.

The compounds of the invention are useful as diuretic agents due to their ability to produce diuresis in mammals. Diuretic activity is measured in mice by a method similar to that described by C. M. Kagawa and M. J. Kalm, Arch. Intern, Pharmcodyn. 137, 241 (1962). Drugs are dosed orally to a group of 6 mice and the average volume of urine excreted is compared to (divided by) the average volume excreted by a positive control group of 6 mice dosed orally with 1000 ml/kg or urea, a known diuretic agent. The resulting drug-/urea ratios if greater than one are indicative of diuretic activity. The diuretic activity in this test of some of the compounds of this invention and of tienilic acid and ethacrynic acid, standard diuretics, is illustrated in Table I.

TABLE I

| COMPOUND | DOSE MG/KG P.O. | DRUG/UREA RATIO |
| --- | --- | --- |
| {[7-chloro-3-(2-fluorophenyl)-1,2-benzisoxazol-6-yl]oxy}acetic acid | 4 | 2.2 |
|  | 32 | 6.1 |
| {[7-chloro-3-(2-thienyl)-1,2-benzisoxazol-6-yl]oxy}acetic acid | 6.4 | 1.2 |
| {[7-chloro-3-phenyl-1,2-benzisoxazol-6-yl)oxy]}acetic acid | 64 | 2.0 |
| {[7-chloro-3-(2-furyl)-1,2-benzisoxazol 6-yl]oxy}acetic acid | 64 | 1.1 |
| {[7-chloro-3-(4-tolyl)-1,2-benzisoxazol-6-yl]oxy}acetic acid | 4 | 1.2 |
|  | 64 | 2.0 |
| {[7-chloro-3-chlorophenyl)-1,2-benzisoxazol-6-yl]oxy}acetic acid | 64 | 1.5 |

TABLE I-continued

| COMPOUND | DOSE MG/KG P.O. | DRUG/UREA RATIO |
| --- | --- | --- |
| }[7-chloro-3-(5-methyl-2-furyl)-1,2-benzisoxazol-6-yl]oxy}acetic acid | 64 | 2.0 |
| {[7-chloro-3-(3-furyl)-1,2-benzisoxazol-6-yl]oxy}acetic acid | 64 | 2.0 |
| {[7-chloro-3-(2-chlorophenyl)-1,2-benzisoxazol-6-yl]oxy}acetic acid | 4 | 1.3 |
|  | 16 | 2.4 |
|  | 32 | 5.6 |
| {[7-chloro-3-(2-tolyl)-1,2-benzisoxazol-6-yl]oxy}acetic acid | 64 | 2.3 |
| [(3-benzyl-7-chloro-1,2-benzisoxazol-6-yl)]acetic acid | 64 | 1.2 |
| {[7-chloro-3-(1-napthyl)-1,2-benzisoxazol-6-yl]oxy}acetic acid | 64 | 1.1 |
| {[7-chloro-3-(3-methyl-2-thienyl)-1,2-benzisoxazol-6-yl]oxy}acetic acid | 64 | 1.4 |
| {[7-chloro-3-(2,6-difluorophenyl)-1,2-benzisoxazol-6-yl]oxy}acetic acid | 4 | 3.1 |
|  | 64 | 7.0 |
| [3-(2-fluorophenyl)-1,2-benzisoxazol-6-yl]oxy}acetic acid | 4 | 1.3 |
|  | 64 | 4.6 |
| {[3-(2-fluorophenyl)-7-methyl-1,2-benzisoxazol-6-yl]oxy}acetic acid | 8 | 2.1 |
|  | 64 | 6.4 |
| {[3-(2-fluorophenyl)-7-iodo-1,2-benzisoxazol-6-yl]oxy}acetic acid | 64 | 2.3 |
| {[7-bromo-3-(2-fluorophenyl)-1,2-benzisoxazol-6-yl]oxy}acetic acid | 4 | 1.7 |
|  | 64 | 6.2 |
| {[7-chloro-3-trans-β-fluorostyrl)-1,2-benzisoxazol-6-yl]oxy}acetic acid | 64 | 1.0 |
| {[5,7-dichloro-3-(2-fluorophenyl)-1,2-benzisoxazol-6-yl]thio}acetic acid | 64 | 3.1 |
| Tienilic Acid | 64 | 1.8 |
|  | 16 | 1.2 |
| Ethacrynic Acid | 64 | 2.5 |

Such utility is effected when a compound of the invention is administered to a patient requiring appropriate treatment at an oral, parenteral or intravenous dose of from 0.1–500 mg/kg of body weight per day. Preferred ranges include 1.0–200 mg/kg of body weight per day.

Compounds of the invention ae also useful as antihypertensive agents due to their ability to depress blood pressure in mammals. Antihypertensive activity is measure in the spontaneous hypertensive rat by the indirect tail cuff method described by A. Schwartz, Ed., *Methods in Pharamacology*, Vol, I, page 135, Appleton-Century-Crofts, New York, N.Y. 1971. In this procedure a group of 5 animals are treated orally with the drug for 3 days in relation to a control group of the same number. The drop in blood pressure is measured on the third day following administration. The antihypertensive activity expressed as mm decrease in mean arterial blood pressure in this test of some of the compounds of this invention is illustrated in Table II.

TABLE II

| COMPOUND | MG/KG P.O. | BLOOD PRESSURE DECREASE mm/HG |
| --- | --- | --- |
| {[7-chloro-3-phenyl-1,2-benzisoxazol-6-yl]oxy}acetic acid | 50 | 15 |
| {[7-chloro-3-(2-furyl)-1,2-benzisoxazol-6-yl]oxy}acetic acid | 50 | 22 |
| {[7-chloro-3-(4-tolyl)-1,2-benzisoxazol-6-yl]oxy}acetic acid | 50 | 16 |
| {[7-chloro-3-(4-chlorophenyl)-1,2-benzisoxazol-6-yl]oxy}acetic acid | 50 | 16 |
| {[7-chloro-3-(5-methyl-2-thienyl)-1,2-benzisoxazol-6-yl]oxy}acetic acid | 50 | 53 |
|  | 10 | 35 |
| [(3-benzyl-)-chloro-1,2-benzisoxazol-6-yl)oxy[acetic acid | 50 | 27 |
| {[7-chloro-3-(1-napthyl)-1,2-benzisoxazol- | 50 | 39 |

TABLE II-continued

| COMPOUND | MG/KG P.O. | BLOOD PRESSURE DECREASE mm/HG |
|---|---|---|
| 6-yl]oxy}acetic acid | | |
| {[7-chloro-3-(2,3-dimethylphenyl)-1,2-benzisoxazol-6-yl]oxy}acetic acid | 50 | 21 |
| {[7-chloro-3-(4-fluorophenyl)-1,2-benzisoxazol-6-yl]oxy}acetic acid | 50 | 19 |
| {[7-chloro-3-(2-pyridyl)-1,2-benzisoxazol-6-yl]oxy}acetic acid oxide | 50 | 21 |
| {[3-(2-fluorophenyl)-7-methyl-1,2-benzisoxazol-6-yl]oxy}acetic acid | 50 | 28 |
| {[7-chloro-3-(trans-β-fluorostyryl)-1,2-benzisoxazol-6-yl]oxy}acetic acid | 50 | 27 |

Such utility is effected when a compound of the invention is administered to a patient requiring appropriate treatment at an oral, parenteral or intravenous dose of from 0.1–500 mg/kg of body weight per day. Preferred ranges include 1.0–200 mg/kg of body weight per day.

The compounds of the invention are further useful as uricosuric agents due to their ability to cause increased uric acid excretion in mammals. Uricosuric activity is measured in a procedure whereby groups of six Wistar rats are dosed orally with the test compound suspended or dissolved in sufficient distilled water such that the volume dosed is equivalent to 25 ml/kg. A corresponding control group is dosed with water only at this level. Urine is collected for five hours and uric acid content determined on an Abbott Biochromatic Analyzer using Uricosquant ® reagent. The results for each group are expressed as average mg of uric acid excreted/kg of rat. Treated groups are compared with control groups for statistical significance. In general, values of 2.5 mg U.A./kg or greater are considered to indicate uricosuric activity. Representative data is given in Table III.

TABLE III

| COMPOUND | DOSE MG/KG | MG U.A./KG. |
|---|---|---|
| {[7-chloro-3-(2-thienyl)-1,2-benzisoxazol-6-yl]oxy}acetic acid | 256 | 3.5 |
| [7-chloro-3-phenyl-1,2-benzisoxazol-6-yl)oxy]acetic acid | 128 | 2.6 |
| }[7-chloro-3-(2-furyl-1,2-benzisoxazol-6-yl]oxy}acetic acid | 128 | 2.5 |
| {[7-chloro-3-(5-methyl-2-thienyl)-1,2-benzisoxazol-6-yl]oxy}acetic acid | 128 | 3.4 |
| {[7-chloro-3-(3-furyl)-1,2-benzisoxazol-6-yl]oxy}acetic acid | 128 | 2.7 |
| {[7-chloro-3-(2-fluorophenyl)-1,2-benzisoxazol-6-yl]oxy}acetic acid | 64 | 3.3 |
| | 128 | 4.0 |
| | 256 | 5.7 |
| | 512 | 13.5 |
| {[7-chloro-3-(4-fluorophenyl)-1,2-benzisoxazol-6-yl]oxy}acetic acid | 32 | 3.0 |
| {[7-chloro-3-(2,6-difluorophenyl)-1,2-benzisoxazol-6-yl]oxy}acetic acid | 64 | 2.5 |
| {[7-chloro-3-(2,4-difluorophenyl)-1,2-benzisoxazol-6-yl]oxy}acetic acid | 64 | 4.4 |
| {[3-(2-fluorophenyl)-1,2-benzisoxazol-6-yl]oxy}acetic acid | 128 | 2.5 |
| {[5,7-dichloro-3-(2-fluorophenyl)-1,2-benzisoxazol-6-yl]thio}acetic acid | 128 | 3.8 |
| Tienilic Acid | 64 | 2.9 |
| Ethacrynic Acid | | inactive |

Such utility is effected when a compound of the invention is administered to a patient requiring appropriate treatment at an oral, parenteral or intravenous dose of from 0.1–500 mg/kg of body weight per day. Preferred ranges include 1.0–200 mg/kg of body weight per day.

It is noteworthy that a significant advantage of these compounds is their dual ability as diuretics and uricosurics. As is known, many paitents experience an increase in uric acid concentration of the blood during treatment with most of the currently marketed diuretics. Elevated uric acid levels are a serrious problem in patients with gouty arthritis. Additionally, elevated uric acid levels are increasingly being considered a risk factor in cardiovascular disease. Accordingly, this concomitant ability to produce diuresis and increase uric acid excretion represents a major advantage of the compounds disclosed herein. Compounds of the invention include:

{[7-chloro-3-(1-buten-2-yl)-1,2-benzisoxazol-6-yl]oxy}acetic acid;

[(7-chloro-3-ethyl-1,2-benzisoxazol-6-yl)oxy]acetic acid;

[(7-chloro-3-cyclopropyl-1,2-benzisoxazol-6-yl)oxy]acetic acid;

[(7-chloro-3-cyclohexyl-1,2-benziosoxazol-6-yl)oxy]acetic acid;

{[7-chloro-3-(2-norbornyl)-1,2-benzisoxazol-6-yl]oxy}acetic acid;

{[3-(1-adamantyl)-7-chloro-1,2-benzisoxazol-6-yl]oxy}acetic acid;

{[7-chloro-3-(1-cyclohexen-1-yl)-1,2-benzisoxazol-6-yl]oxy}acetic acid;

[(7-chloro-3-cyclopropylmethyl-1,2-benzisoxazol-6-yl)oxy]acetic acid;

[(7-chloro-3-cyclopentylmethyl-1,2-benzisoxazol-6-yl)oxy]acetic acid;

{[7-chloro-3-(2-cyclopenten-1-methyl)-1,2-benzisoxazol-6-yl]oxy}acetic acid;

[(7-chloro-3-propargyl-1,2-benzisoxazol-6-yl)oxy]acetic acid;

{[7-chloro-3-(4-methoxyphenyl)-1,2-benzisoxazol-6-yl]oxy}acetic acid;

{[7-chloro-3-(4-hydroxy-2-fluorophenyl)-1,2-benzisoxazol-6-yl]oxy}acetic acid;

{[7-chloro-3-(3-trifluoromethylphenyl)-1,2-benzisoxazol-yl]oxy}acetic acid;

{[7-chloro-3-(4-nitrophenyl)-1,2-benzisoxazol-6-yl]oxy}acetic acid;

{[7-chloro-3-(4-aminophenyl)-1,2-benzisoxazol-6-yl]oxy}acetic acid;

{[7-chloro-3-(4-acetamidophenyl)-1,2-benzisoxazol-6-yl]oxy}acetic acid;

{[4,5-dichloro-3-(2-fluorophenyl)-1,2-benzisoxazol-6-yl]oxy}acetic acid;

{[(4,7-dichloro-3-(2-fluorophenyl)-1,2-benzisoxazol-6-yl]oxy}acetic acid;

[(4-methyl-3-phenyl-1,2-benzisoxazol-6-yl)oxy]acetic acid
[(5-methyl-3-phenyl-1,2-benzisoxazol-6-yl)oxy]acetic acid
{[7-chloro-3-(2-pyrryl)-1,2-benzisoxazol-6-yl]oxy}acetic acid;
[(3-phenyl-1,2-benzisoxazol-4-yl)oxy]acetic acid;
[(3-phenyl-1,2-benzisoxazol-5-yl)oxy]acetic acid;
[(3-phenyl-1,2-benzisoxazol-7-yl)oxy]acetic acid;
benzyl [7-chloro-3-(2-fluorophenyl)-1,2-benzisoxazol-6-yl]oxy acetate;
n-propyl}3-(2-thienyl)-1,2-benziosoxazole-6-yl]oxy}acetate
t-butyl[(3-phenyl-1,2-benziosoxazol-7-yl)oxy]acetate.
{[7-chloro-3-(2-fluorophenyl)-1,2-benzisoxazol-6-yl]oxy}acetyl chloride;
{[7-bromo-3-(2-fluoro-4-hydroxyphenyl)-1,2-benzisoxazol-6-yl]oxy}acetic acid;
{[7-chloro-3-(2-fluorophenyl)-1,2-benzisoxazol-6-yl]oxy}acetamide;
N,N-diethyl-{[7-chloro-3-(2-fluorophenyl)-1,2-benzisoxazol-6-yl]oxy}acetamide;
2-{[7-bromo-3-(2-fluorophenyl)-1,2-benzisoxazol-6-yl]oxy}ethanol;
1,1-diethoxy-2-{[7-chloro-3-(2-fluorophenyl)-1,2-benzisoxazol-6-yl]oxy}ethane;
{[7-chloro-3-(2-fluorophenyl)-1,2-benzisoxazol-6-yl]oxy}acetaldehyde;
{[7-bromo-3-(2-fluorophenyl)-1,2-benzisoxazol-6-yl]oxy}acetonitrile;
N-hydroxy-{[7-chloro-3-(2-fluorophenyl)-1,2-benzisoxazol-6-yl]oxy}acetamide;
N-amidino-{[7-chloro-3-(2-fluorophenyl)-1,2-benzisoxazol-6-yl]oxy}acetamide;
5-{[7-chloro-3-(2-fluorophenyl)-1,2-benzisoxazol-6-yl]oxymethyl}tetrazole;
{[7-bromo-5-chloro-3-(2-fluorophenyl)-1,2-benzisoxazol-6-yl]oxy}acetic acid;
{[7-bromo-5-methyl-3-(2-fluorophenyl)-1,2-benzisoxazol-6-yl]oxy}acetic acid;
glyceryl{[7-chloro-3-(2-fluorophenyl)-1,2-benzisoxazol-6-yl]oxy}acetate;
{[7-chloro-3-(2-fluorophenyl)-1,2-benzisothiazol-6-yl]thio}acetic acid;
{[7-bromo-3-(2-fluorophenyl)-1,2-benzisothiazol-6-yl]thio}acetic acid;
{[7-bromo-3-(2,6-difluorophenyl)-1,2-benzisoxazol-6-yl]oxy}acetic acid;
{[7-methyl-3-(2,5-difluorophenyl)-1,2-benzisoxazol-6-yl]oxy}acetic acid;
{[7-bromo-3-(2,3-difluorophenyl)-1,2-benzisoxazol-6-yl]oxy}acetic acid;
{[7-bromo-3-(2,5-difluorophenyl)-1,2-benzisoxazol-6-yl]oxy}acetic acid.
{[7-chloro-3-(2-fluorophenyl)-1,2-benzisothiazol-6-yl]oxy}acetic acid;
{[7-bromo-3-(2-fluorophenyl)-1,2-benzisothiazol-6-yl]oxy}acetic acid;
{[7-chloro-3-[4-(methylthio)phenyl]-1,2-benzisoxazol-6-yl]oxy}acetic acid;
{[7-fluoro-3-(2-fluorophenyl)-1,2-benzisoxazol-6-yl]oxy}acetic acid; and
{[7-chloro-3-(3-fluoro-2-thienyl)-1,2-benzisoxazol-6-yl]oxy}acetic acid.

Effective quantities of the compounds of the invention may be administered to a patient by any one of various methods, for example, orally as in capsules or tablets, parenterally in the form of sterile solutions or suspensions, and in some cases intravenously in the form of sterile solutions. The free acid final products, while effective themselves, may be formulated and administered in the form of their pharmaceutically acceptable salts for purposes of stability, convenience of crystallization, increased solubility and the like.

The active compounds of the present invention may be orally administered, for example, with an inert diluent or with an edible carrier, or they may be enclosed in gelatin capsules, or they may be compressed into tablets. For the purpose of oral therapeutic administration, the active compounds of the invention may be incorporated with excipients and used in the form of tablets, troches, capsules, elixirs, suspensions, syrups, wafers, chewing gum and the like. These preparations should contain at least 0.5% of active compound, but may be varied depending upon the particular form and may conveniently be between 4% to about 70% of the weight of the unit. The amount of active compound in such compositions is such that a suitable dosage will be obtained. Preferred compositions and preparations according to the present invention are prepared so that an oral dosage unit form contains between 1.0-300 milligrams of active compound.

The tablets, pills, capsules, troches and the like may also contain the following ingredients: a binder such as microcrystalline cellulose, gum tragacanth or gelatin; and excipient such as starch or lactose, a disintegrating agent such as alginic acid, Primogel, corn starch and the like; a lubricant such as magnesium stearate or Sterotex; a glidant such as colloidal silicon dioxide; and a sweetening agent such as sucrose or saccharin may be added or a flavoring agent such as peppermint, methyl salicylate, or orange flavoring. When the dosage unit form is a capsule, it may contain, in addition to materials of the above type, a liquid carrier such as fatty oil. Other dosage unit forms may contain other various materials which modify the physical form of the dosage unit, for example, as coatings. Thus, tablets or pills may be coated with sugar, shellac, or other enteric coating agents. A syrup may contain, in addition to the active compounds, sucrose as a sweetening agent and certain preservatives, dyes and colorings and flavors. Materials used in preparing these various compositions should be pharmaceutically pure and non-toxic in the amounts used.

For the purposes of parenteral therapeutic administration, the active compounds of the invention may be incorporated into a solution or suspension. These preparations should contain at least 0.1% of active compound, but may be varied to be between 0.5 and about 30% of the weight thereof. The amount of active compound in such compositions is such that a suitable dosage will be obtained. Preferred compositions and preparations according to the present invention are prepared so that a parenteral dosage unit contains between 0.5 to 100 milligrams of active compound.

The solutions or suspensions may also include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in ampoules, disposable syringes or multiple dose vials made of glass or plastic.

The present invention is further illustrated by the following examples of representative compounds and procedures.

EXAMPLE 1 a. To a solution of 31.6 g of 2-fluorobenzoyl chloride in 100 ml of dichloroethane there is added incrementally 26.5 g of aluminum chloride over a 30 minute period. Upon completion of the addition the mixture turns yellow and then darkens. Thereafter to this darkened mixture there is added dropwise a solution of 32 g of 2,3-dichloroanisole in 50 ml of 1,2-dichloroethane. After the addition is complete the mixture is stirred for 2 hours before being poured over a mixture of 100 ml of concentrated hydrochloric acid and 100 ml of crushed ice.

The organic phase of the two-phase mixture is evaporated under vacuum and the aqueous mixture is extracted with either. The combined ether extracts successively are washed with a 10% potassium carbonate solution, washed with water and dried and the ether is evaporated to dryness leaving an off-white solid which is recrystallized from an ether-hexane mixture to yield the product 2'-fluoro-4-methoxy-2,3-dichlorobenzophenone having a melting point of 74° to 77° C.

b. To a mixture of 38.5 g of 2'-fluoro-4-methoxy-2,3-dichlorobenzophenone and 34.7 g of aluminum chloride in 250 ml of benzene is refluxed for 5 hours, then poured over a mixture of 100 ml of concentrated hydrochloric acid and 100 ml of ice. The two-phase mixture is extracted with ethyl acetate and the combined extracts are dried and concentrated to dryness leaving a solid residue. The residue is triturated with hexane and the resulting solid is recrystallized from an ether-hexane mixture to yield the product 2,3-dichloro-4-hydroxy-2'-fluoro-benzophenone having a melting point of 128° to 131° C.

c. A solution of 31.8 g of 2,3-dichloro-4-hydroxy-2'-fluoro-benzophenone and 15.3 g of hydroxylamine hydrochloride in 150 ml of pyridine is refluxed for 64 hours. Thereafter the pyridine is evaporated under vacuum and a 5% aqueous hydrochloric acid solution is added. The acidified solution is extracted with ethyl acetate and the combined extracts are dried before being concentrated to dryness. The resulting solid is recrystallized from an aqueous ethanol solution to yield the product 2,3-dichloro-4-hydroxy-2'-fluorobenzophenone oxime with a melting point of 168° to 175° C.

d. A solution of 18.4 g of 2,3-dichloro-4-hydroxy-2'-fluorobenzophenone oxime and 3.6 g of sodium hydride in 120 ml of dimethylformamide and 120 ml of benzene is maintained at a temperature of from 80°–85° C. for 3 hours. Thereafter, the mixture is permitted to reach ambient temperature after which a solution of 11.0 g of ethyl bromoacetate in 20 ml of dimethylformamide is added dropwise. After the addition is complete, the mixture is stirred for 30 minutes and then water is added to decompose any excess sodium hydride. The mixture is extracted with ethyl acetate and the combined extracts are dried and evaporated to dryness leaving a solid residue. The residue is recrystallized several times from 95% ethyl alcohol to yield the pure product ethyl{[7-chloro-3-(2-fluorophenyl)-1,2-benzisoxazol-6-yl]oxy}acetate having a melting point of 102° to 104° C.

Analysis: Calculated for $C_{17}H_{13}ClFNO_4$: 58.38%C; 3.75%H; 4.01N. Found: 58.11%C; 3.62%H; 3.86%N.

EXAMPLE 2

A mixture of 10.0 g of ethyl{[7-chloro-3-(2-fluorophenyl)-1,2-benzisoxazol-6-yl]oxy}acetate, 100 ml of 10% sodium hydroxide, and 350 ml of ethyl alcohol is refluxed for 3.5 hours. Thereafter, the ethyl alcohol is removed under vacuum and the residue is acidified with a 5% hydrochloric acid solution effecting a solid precipitate. The precipitate is collected by filtration and dried. The dried product is recrystallized from 95% ethyl alcohol to yield the product {[7-chloro-3-(2-fluorophenyl)-1,2-benzisoxazol-6-yl]oxy}acetic acid having a melting point of 190° to 191° C.

EXAMPLE 3 a. To a mixture of 12.5 g of aluminum chloride and 45 ml of carbon disulfide there is added dropwise 7.1 g of 2-fluorobenzoyl chloride while maintaining the temperature below 0° C. This low temperature is maintained for 1.5 hours. While maintaining this same low temperature, 5 g of 2,3-dichlorophenoxyacetic acid is added incrementally. After addition is complete, the reaction mixture is maintained at low temperature for 30 minutes and then permitted to reach ambient temperature after which it is refluxed for 28 hours. The carbon disulfide is decanted from the refluxed solution leaving a dark orange residue which is poured onto a mixture of 500 ml of ice/water and 100 ml of concentrated hydrochloric acid. The resulting pink precipitate is collected by filtration, rinsed with 300 ml of warm water (50° C.) and dried in vacuum oven. The dried product is recrystallized twice from aqueous ethyl alcohol to form the product 2,3-dichloro-4-(2-fluorobenzoyl)phenoxyacetic acid having a melting point of 153° to 156° C.

b. A mixture of 1.0 g of 2.3-dichloro-4-(2-fluorobenzoyl)phenoxyacetic acid and 1 g of hydroxylamine hydrochloride in 10 ml of pyridine is refluxed for 2 hours. Thereafter, the solvent is evaporated in vacuo and the residue is stirred for 16 hours with 5% hydrochloric acid. The product is filtered off and the collected solid is recrystallized from aqueous ethyl alcohol to give the product 2,3-dichloro-4-(2-fluorobenzohydroximoyl)phenoxyacetic acid having a melting point of 91° to 96° C.

c. A mixture of 0.3 g of 2,3-dichloro-4-(2-fluorobenzohydroximoyl)phenoxyacetic acid and 0.05 g of sodium hydride in 5 ml of benzene and 5 ml of dimethylformamide is refluxed for 3 hours. To the mixture, after it has been permitted to cool there is added 5% hydrochloric acid causing the benzene to separate. The benzene is evaporated in vacuo and the resulting precipitate is collected by filtration and recrystallized from aqueous ethyl alcohol to yield the product {[7-chloro-3-(2-fluorophenyl)-1,2-benzisoxazol-6-yl]oxy}acetic acid having a melting point of 188° to 189° C.

Analysis: Calculated for $C_{15}H_9ClFNO_4$: 56.00%C; 2.83%H; 4.36%N; Found: 55.94%C; 2.86%H; 4.32%N

EXAMPLE 4 a. A mixture of 3.8 g of (2,3-dichloro-4-hydroxyphenyl) 2'-thienylmethanone and 2.0 g of hydroxylamine hydrochloride in 20 ml of pyridine is refluxed for 6 hours. Thereafter, the pyridine is evaporated in vacuo. To the residue there is added 5% hydrochloric acid and the acidified mixture is extracted with ethyl acetate. The extract, sequentially, is washed with water, dried and evaporated to dryness. The residue is recrystallized from an ethanol and water mixture to yield the produce (2,3-dichloro-4-hydroxyphenyl)-2'-thienylmethanone oxime having a melting point of 179° to 183° C.

b. To a mixture of 3.0 g of (2,3-dichloro-4-hydroxyphenyl)-2'-thienylmethanone oxime in 30 ml of dimethylformamide and 30 ml of toluene is added 0.62 g of sodium hydride. Thereafter, the reaction mixture is maintained at 100° C. for 2 hours and then at 115° C. for 2.5 hours. The mixture is permitted to cool prior to adding thereto dropwise a solution of 1.9 g of ethyl bromoacetate in 10 ml of dimethylformamide. After addition is complete, the reaction mixture is stirred for 2.25 hours and then water is added to decompose any excess sodium hydride. The reaction mixture is extracted with ethylacetate and the extract is, sequentially, washed with water, dried and evaporated. The residue is recrystallized from ethanol to yield the product ethyl{[7-chloro-3-(2-thienyl)-1,2-benzisoxazol-6-yl]oxy}acetate having a melting point of 142° to 143° C.

Analysis: Calculated for $C_{15}H_{12}ClNO_4S$: 53.33%C; 3.58%H; 4.15%N; Found: 53.28%C; 3.58%H; 4.17%N

EXAMPLE 5 a. A solution of 18.0 g of 2,3-dichloro-4-hydroxybenzophenone and 9.3 g of hydroxylamine hydrochloride in 100 ml of pyridine is refluxed for 2 hours. Thereafter, the pyridine is evaporated under vacuum and the residual liquid is partitioned between 5% hydrochloric acid and ethyl acetate. The ethylacetate extract is washed with water, dried, and evaporated to give 2,3-dichloro-4-hydroxy-benzophenone oxime.

Said 2,3-dichloro-4-hydroxybenzophenone is prepared in a manner consistent with the procedure described in Example 1(a) and (b) with benzoyl chloride replacing 2-fluorobenzoyl chloride.

b. A solution of 2,3-dichloro-4-hydroxybenzophenone oxime and 2.6 g of sodium hydride in 50 ml of dimethylformamide and 50 ml of toluene is heated to 118° C. and maintained at this temperature for 50 minutes. Thereafter, the reaction is permitted to cool prior to the dropwise addition of 7.9 g of ethyl bromoacetate in 50 ml of dimethylformamide. After the addition is complete the reaction mixture is stirred at ambient temperature for 40 minutes. To the well stirred mixture water is added dropwise to decompose any excess sodium hydride. The toluene is evaporated under vacuum and the resulting precipitate is collected by filtration and then rinsed with ether to yield the product ethyl[(7-chloro-3-phenyl-1,2-benzisoxazol-6-yl)oxy]acetate having a melting point of 130° to 132° C.

Analysis: Calculated for $C_{17}H_{14}ClNO_4$: 61.54%C; 4.25%H; 4.22%N; Found: 61.34%C; 4.15%H; 4.17%N

EXAMPLE 6

To a solution of 8.3 g of ethyl[7-chloro-3-phenyl-1,2-benzisoxazol-6-yl)oxy]acetate, Example 5, in 160 ml of ethyl alcohol is added 6 ml of 7N sodium hydroxide. Thereafter, the reaction mixture is refluxed for 45 minutes. The precipitate is collected by filtration and then successively rinsed with ethyl alcohol and ether. The precipitate is suspended in 200 ml of hot water and this mixture is acidified with concentrated hydrochloric acid. The acidified mixture is stirred for 1 hour and the gray precipitate is collected by filtration. The precipitate is recrystallized from ethyl acetate to yield the pure product [(7-chloro-3-phenyl-1,2-benzisoxazol-6-yl)oxy]acetic acid having a melting point of 219° to 221° C.

Analysis: Calculated for $C_{15}H_{10}ClNO_4$: 59.32%C; 3.32%H; 4.61%N; Found: 59.33%C; 3.38%H; 4.57%N

EXAMPLE 7

19.8 g of 3,2-dichloro-4-hydroxyphenyl-2'-furylmethanone oxime is dissolved in 200 ml of dimethylformamide, then 4.8 g of sodium hydride is added thereto. After hydrogen gas evolution ceases the reaction mixture is heated at 130° C. The mixture is cooled to 5° C. and to the cooled mixture is added a solution of 16.7 g of bromoacetate in 20 ml of dimethylformamide. After stirring for 45 minutes the reaction mixture is then poured into water to produce a crystalline product. The product is collected by filtration, sucessively washed with ethyl alcohol and ether and finally recrystallized from an ethyl alcohol-ethyl acetate mixture to yield the product ethyl[(7-chloro-3-(2-furyl)-1,2-benzisoxazol-6-yl)oxy]acetate having a melting point of 151° to 152° C.

Analysis: Calculated for $C_{15}H_{12}ClNO_5$: 56.00%C; 3.76%H; 4.35%N; Found: 55.91%C; 3.83%H; 4.32%N

EXAMPLE 8

To a boiling suspension of 15.0 g of ethyl[(7-chloro-3-(2-furyl)-1,2-benzisoxazol-6-yl)oxy]acetate, Example 7, in 500 ml of boiling 95% ethyl alcohol there is added 10 ml of a 50% sodium hydroxide solution causing the sodium salt to precipitate out almost immediately. An additional 300 ml of 95% ethyl alcohol is added and boiling is maintained for 30 minutes. The reaction mixture is permitted to cool slightly, after which 100 ml of a 5% hydrochloric acid solution is added thereto. The product begins to separate with cooling, 250 ml of water is added and the diluted mixture is chilled with ice. The precipitate is collected by filtration and recrystallized from isopropyl alcohol to yield the product {[7-chloro-3-(2-furyl)-1,2-benzisoxazol-6-yl]oxy}acetic acid having a melting point of 230° to 233° C.

Analysis: Calculated for $C_{13}H_8ClNO_5$: 53.17%C; 2.74%H; 4.77%N; Found: 52.83%C; 2.83%H; 4.74%N

EXAMPLE 9 a. A mixture of 28.3 g of (2,3-dichloro-4-hydroxyphenyl)-(5'-methyl-2'-thienyl)methanone and 14.0 g of hydroxylamine hydrochloride in 300 ml of pyridine is refluxed for 16 hours. Thereafter, the solvent is removed under vacuum and the residue is treated with 5% hydrochloric acid. The treated residue is successively extracted with a mixture of dichloroethane and ether and dried and the solvent removed by evaporation. The product is triturated with hexane to produce the desired oxime, (2,3-dichloro-4-hydroxyphenyl)-(5'-methyl-2'-thienyl)methanone oxime.

b. To a mixture of the above oxime in 200 ml of dimethylformamide there is added 5.3 g of sodium hydride. The reaction mixture is maintained, successively, at 120° C. for 1.5 hours, 130° C. for 1 hour, and 140° C. for 1 hour, then cooled to 35° C. To this cooled mixture 18.3 g of the ethyl bromoacetate in 20 ml of dimethylformamide there is added and the mixture is stirred for 20 minutes. The reaction mixture is poured into a saturated sodium chloride solution to yield a crystalline product which is collected by filtration. The product is washed successively with methyl alcohol and ether and then recrystallized from isopropyl alcohol to give the product ethyl{[7-chloro-3-(5-methyl-2-thienyl)-1,2-benzisoxazol-6-yl]oxy}acetate having a melting point of 149° to 150° C.

Analysis: Calculated for $C_{16}H_{14}ClNO_4S$: 54.62%C; 4.04%H; 3.98%N; Found: 54.60%C; 3.97%H; 3.98%N

EXAMPLE 10

The substitution of (2,3-dichloro-4-hydroxyphenyl)-(5'-methyl-2'-furyl)methanone for (2,3-dichloro-4-hydroxyphenyl)-(5'-methyl-2'-thienyl)methanone in the procedure described in Example 9(a) and, thereafter following the procedure described in Example 9(b) provides ethyl{[7-chloro-3-(5-methyl-2-furyl)-1,2-benzisoxazol-6-yl]oxy}acetate, having a melting point of 139° to 141° C.

Analysis: Calculated for $C_{16}H_{14}ClNO_5$: 57.23%C; 4.20%H; 4.17%N; Found: 57.28%C; 4.18%H; 3.93%N

EXAMPLE 11

To a suspension of 15.0 g of ethyl[7-chloro-3-(5-methyl-2-furyl)-1,2-benzisoxazol-6-yl]oxy acetate, Example 10, in 800 ml of ethyl alcohol there is added 10 ml of a 50% sodium hydroxide solution. The reaction mixture is refluxed with vigorous stirring for 1.5 hours and 100 ml of 5% hydrochloric acid is added thereto. The resulting solution is sequentially chilled and diluted with water as the product begins to crystallize. The product is collected by filtration and recrystallized from methyl alcohol to yield {[7-chloro-3-(5-methyl-2-furyl)-1,2-benzisoxazol-6-yl]oxy}acetic acid, mp 217°–219° C.

Analysis: Calculated for $C_{14}H_{10}ClNO$: 54.65%C; 3.28%H; 4.55%N; Found: 54.74%C; 3.40%H; 4.49%N

EXAMPLE 12 a. A mixture of 2,3-dichloro-4-hydroxy-4'-methylbenzophenone and 12.5 g of hydroxylamine hydrochloride in 200 ml of pyridine is refluxed for 2 hours. Thereafter the pyridine is evaporated off under vacuum and the residue is partitioned between ethyl acetate and 5% hydrochloric acid. The ethyl acetate extract is, successively, washed with water, dried and concentrated to dryness leaving 2,3-dichloro-4-hydroxy-4'-methylbenzophenone oxime.

b. A mixture of the above oxime and 5.2 g of sodium hydride in 300 ml of dimethylformamide is maintained at 87° C. for 3 hours. This mixture is permitted to cool to ambient temperature, after which 16.0 g of ethyl bromoacetate in 50 ml of dimethylformamide is added thereto dropwise. After addition is complete the mixture is stirred for 30 minutes and poured into water to produce a precipitate which is ethyl{[7-chloro-3-(4-tolyl)-1,2-benzisoxazol-6-yl]oxy}acetate, mp 157°–159° C.

EXAMPLE 13

A mixture of 20 g of ethyl{[7-chloro-3-(4-tolyl)-1,2-benzisoxazol-6-yl]oxy}acetate, Example 12, and 15 ml of 50% sodium hydroxide in 600 ml of ethyl alcohol is refluxed for 1 hour. Thereafter, the hot mixture is diluted with 500 ml of water and acidified with concentrated hydrochloric acid. The acidified suspension is, successively, stirred for 30 minutes and filtered and the filter cake is recrystallized from dimethylformamide to yield the product {[7-chloro-3-(4-tolyl)-1,2-benzisoxazol-6-yl]oxy}acetic acid having a melting point of 257° to 260° C.

Analysis: Calculated for $C_{17}H_{14}ClNO_4$: 60.48%C; 3.78%H; 4.41%N; Found: 60.39%C; 3.77%H; 4.38%N

EXAMPLE 14 a. A mixture of 41 g of (2,3-dichloro-4-hydroxyphenyl)-4'-chlorobenzophenone and 18.9 g of hydroxylamine hydrochloride in 300 ml of pyridine is refluxed for 2 hours. Thereafter, the pyridine is removed under vacuum and the residue is partitioned between ethyl acetate and 5% hydrochloric acid. The ethyl acetate portion is, successively, washed with water, dried and concentrated to dryness leaving 2,3-dichloro-4-hydroxy-4'-chlorobenzophenone oxime.

b. A mixture of the 41.5 g of the above oxime and 7.9 g of sodium hydride in 300 ml of dimethylformamide is maintained at a temperataure of 111° C. for 2 hours. Thereafter, the reaction mixture is permitted to cool to ambient temperature after which a mixture of 23 g of ethyl bromoacetate in 50 ml of dimethylformami is added thereto dropwise. After addition is complete the reaction mixture is stirred for 30 minutes and permitted to stand for 16 hours. The mixture is poured into water to yield a precipitate, collected by filtration, of ethyl{[7-chloro-3-(4-chlorophenyl)-1,2-benzisoxazol-6-yl]oxy}acetate, m.p. 179° C.

EXAMPLE 15

A mixture of 25 g of ethyl{[7-chloro-3-(4-chlorophenyl)-1,2-benzisoxazol-6-yl]oxy}acetate, Example 14, and 20 ml of 50% The hot mixture is diluted with 300 ml of water and then acidified with concentrated hydrochloric acid. The acidified mixture is stirred for 30 minutes and then filtered and the filter cake is recrystallized from a dimethylformamide-ethylacetate mixture to yield the product {[7-chloro-3-(4-chlorophenyl)-1,2-benzisoxazol-6-yl]oxy}acetic acid having a melting point of 254° to 257° C.

Analysis: Calculated for $C_{15}H_9Cl_2NO_4$: 53.28%C; 2.68%H; 4.14%N; Found: 53.01%C; 2.39%H; 4.03%N In the above examples, where not specifically shown, the oxime precursor is prepared from the appropriate ketone in a fashion similar to Example 1c.

EXAMPLE 16

A suspension of 0.72 g of ethyl{[7-chloro-3-(2-thienyl)-1,2-benzisoxazol-6-yl]oxy}acetate, Example 4, and 10 ml of concentrated aqueous sodium hydroxide in 40 ml of ethyl alcohol is refluxed for 1 hour. Thereafter, the ethyl alcohol is removed by evaporation in vacuo. The residual suspension is acidified with concentrated hydrochloric acid and then stirred at ambient temperature for 30 minutes. The resulting crude product is collected by filtration and then recrystallized from ethyl alcohol to provide the product, mp 217°–220° C., of {[7-chloro-3-(2-thienyl)-1,2-benzisoxazol-6-yl]oxy}acetic acid.

Analysis: Calculated for $C_{13}H_8ClNO_4S$: 50.41%C; 2.60%H; 4.52%N. Found: 50.13%C; 2.47%H; 4.48%N.

EXAMPLE 17 a. A reaction mixture of 32.8 g of 3-methyl-2-thiophene carboxylic acid chloride and 35.4 g of 2,3-dichloroanisole and 26.7 g of aluminum chloride in 200 ml of carbon disulfide is refluxed for 40 hours before being poured into ice-hydrochloric acid. The resulting crystalline product is collected by filtration and then sequentially washed with hexane and recrystallized from a toluene-hexane mixture to provide the product, mp 136°–138° C., of (2,3-dichloro-4-methoxy)(3-methyl-2-thienyl)methanone.

Analysis: Calculated for $C_{13}H_{10}Cl_2O_2S$: 51.48%C; 3.35%H; 10.65%S. Found: 51.81%C; 3.35%H; 10.85%S.

b. A mixture of 0.6 g of (2,3-dichloro-4-methoxy)(3-methyl-2-thienyl)methanone and $NH_2OH \cdot HCl$ in pyridine is converted to its corresponding oxime. Thereafter, the oxime (mixture of isomers) (37.8 g) is dissolved in 70 ml of dimethylformamide and the solution added to a suspension of 3.3 g of sodium hydride in 100 ml of dimethylformamide. After the reaction is completed it is poured into water. The pH of the aqueous mixture is adjusted to 6–7 with dilute hydrochloric acid. The resulting precipitate is collected by filtration and then sequentially washed well with ether and recrystallized from a toluene-hexane mixture to provide the product, mp 154°–156° C., 7-chloro-3(3-methyl-2-thienyl)-6-1,2-benzisoxazole.

Analysis: Calculated for $C_{13}H_{10}ClNO_2S$: 55.81%C; 3.60%H; 5.01%N; 11.46%S. Found: 55.90%C; 3.54%H; 4.98%N; 11.22%S.

c. A mixture of 13.3 g of 7-chloro-3-(3-methyl-2-thienyl)-6-methoxy-1,2-benzisoxazole and 25 g of $BBr_3$ in $CH_2Cl_2$ is refluxed about 18 hours and then poured into $H_2O$ and extracted with ether. The ether extract is dried and evaporated and then triturated with hexane to yield 7-chloro-6-hydroxy-3-(3-methyl-2-thienyl)-1,2-benzisoxalole, mp 197°–198° C.

Analysis: Calculated for $C_{12}H_8ClNO_2S$: 54.24%C; 3.03%H; 5.27%N. Found: 54.22%C; 3.05%H; 5.08%N.

d. A mixture of 10.3 g of 7-chloro-6-hydroxy-3-(3-methyl-2-thienyl)-1,2-benzisoxazole in 60 ml DMF is added to a suspension of NaH (1.1 g) in 40 ml DMF. Ethyl bromoacetate (6.7 g) is added thereto and the reaction mixture is heated to 50° C. for 30 minutes. 100 ml $H_2O$ and 25% aqueous NaOH is added and the reaction mixture is heated to 90° C. for three hours. The reaction mixture is then poured into $H_2O$ and acidified with concentrated hydrochloric acid. The acidified mixture is extracted with ether, water, washed and dried. Evaporation and recrystallization form an ethyl acetate-hexane mixture which gives {7-chloro-3-(3-methyl-2-thienyl)-1,2-benzisoxazol-6-yl]oxy}acetic acid.

Analysis: Calculated for $C_{14}H_{10}ClNO_4S$: 51.93%C; 3.11%H; 4.33%N. Found: 51.93%C; 3.05%H; 4.28%N.

EXAMPLE 18

A mixture of 15.0 g of ethyl{[7-chloro-3-(5-methyl-2-thienyl)-1,2-benzisoxazole-6-yl]oxy}acetate of Example 9b and 10 ml of 50% NaOH in 800 ml of ethanol is refluxed for 30 minutes and then 100 ml of the 5% HCl is added, making the solution homogeneous. A product begins to crystallize as the solution cools and additional water is added. The product is filtered off and recrystallized form isopropanol giving {[7-chloro-3-(5-methyl-2-thienyl)-1,2-benzisoxazol-6-yl]oxy}acetic acid, mp 235°–238° C.

Analysis: Calculated for $C_{14}H_{10}ClNO_4S$: 51.93%C; 3.11%H; 4.33%N; 9.91%S. Found: 51.69%C; 3.14%H; 4.20%N; 10.02%S.

EXAMPLE 19

3-Furoyl chloride (18.0 g) and 2,3-dichloro anisole (24.7 g) are dissolved in 125 ml of $CS_2$ and treated with $AlCl_3$ (18.7 g), first at 5° C. and then at room temperature. After five hours the reaction is quenched with ice/HCl and extracted with $CH_2Cl_2$. Drying and evaporation gives a crystalline product that is triturated with hexane to yield 4-(3-furoyl)-2,3-dichloroanisole, mp 118°–122° C.

A molten bath of pyridine HCl is prepared by adding 16 ml of concentrated HCl (0.186 mole) to 14.2 g of pyridine and heating the mixture to 210° C. under nitrogen and allowing the $H_2O$ to distill out. The anisole (5.0 g) is added in portions and heating is continued for one hour and the solution poured over ice and extracted with ethyl acetate. Drying and evaporation gives 4-(3-furoyl)-2,3-dichlorophenol, mp 138°–142° C.

The phenol is combined with hydroxylamine hydrochloride in pyridine and refluxed for three hours. The pyridine is evaporated off and the resultant mixture is acidified with hydrochloric acid and then extracted with ethyl acetate. The ethyl acetate extract is water washed, dried and evaporated to dryness to yield an oxime which is dissolved in 100 ml of DMF and added to a suspension of NaH (7.0 g) in 100 ml of DMF. After warming for two hours at 120° C., the reaction is cooled to 45° C. and ethyl bromoacetate (24.0 g) in 20 ml of DMF is added. The reaction is quenched with brine and a resultant solid product filtered and washed with ethanol and then ether to give a crude phenoxy ester. Hydrolysis of the crude ester for 45 minutes in refluxing ethanol (500 ml) containing 10 ml of 50% NaOH gives a crystalline acid after acidifying and chilling. The acid is recrystallized by suspending it in boiling methanol and adding DMF until dissolution occurs. Water is then added and crystallization begins immediately to yield {[7-chloro-3-(3-furyl)-1,2-benzisoxazol-6-yl]oxy}acetic acid, mp 225°–227° C.

Analysis: Calculated for $C_{13}H_8ClNO_5$: 53.17%C; 2.74%H; 4.77%N. Found: 53.36%C; 2.85%H; 4.71%N.

EXAMPLE 20 a. To a solution of 24.6 g of 2,6-difluorobenzoylchloride in 100 ml of 1,2-dichloroethane, 18.5 g of $AlCl_3$ is added in portions over a 30 minute period. A solution of 22.5 g of 2,3-dichloroanisole in 100 ml of 1,2-dichloroethane is added thereto. The mixture is stirred for one hour and poured over 100 ml concentrated HCl and ice. The organic layer is separated and the aqueous layer extracted with $CHCl_3$. The organic extract is washed with water, dried ($Na_2SO_4$) and evaporated to give an oil which crystallizes from hexane to yield solid 2,3-dichloro-4-methoxy-2',6'-difluorobenzophenone which upon recrystallization from ether has an mp 94°–96° C.

Analysis: Calculated for $C_{14}H_8Cl_2F_2O_2$: 53.02%C; 2.54%H; 11.98%F. Found: 53.21%C; 2.50%H; 12.08%F.

b. A mixture of 50.5 g of 2,3-dichloro-4-methoxy-2',6'-difluorobenzophenone, 44.27 g of hydroxylamine HCl in 200 ml of pyridine is refluxed for 48 hours. The pyridine is evaporated in vacuo and the residue partitioned between 5% HCl and ethyl acetate. The extract is washed with water, dried over $Na_2SO_4$ and evaporated to give a mixture of isomers. An analytical sample of 2,3-dichloro-4-methoxy-2',6'-difluorobenzophenone oxime, mp 173°–189° C. is recrystallized from 95% ethanol:

Analysis: Calculated for $C_{14}H_9Cl_2F_2NO_2$: 50.62%C; 2.73%H; 4.22%N. Found: 50.84%C; 2.68%H; 4.14%N.

c. To a mixture of 5 g of NaH in 200 ml of DMF, 48 g of 2,3-dichloro-4-methoxy-2',6'-difluorobenzophenone oxime in 250 ml of DMF is added dropwise in an atmosphere of $N_2$ while the temperature is maintained at approximately 40° C. After the addition, the mixture is stirred 30 minutes and poured into ice water. A crude product, which is a mixture of isomers, is filtered off and chromatographed on silica gel with $CHCl_3$ as eluant to yield 7-chloro-3-(2,6-difluorophenyl)-6-methoxy-1,2-benzisoxazole which is recrystallized from toluene for analysis, mp 175°–179° C.

Analysis: Calculated for $C_{14}H_8ClF_2NO_2$: 56.87%C; 2.73%H; 4.74%N. Found: 56.99%C; 2.64%H; 4.64%N.

d. A mixture of 10.8 g of 7-chloro-3-(2,6-difluorophenyl)-6-methoxy-1,2-benzisoxazole and 40.3 g of pyridine HCl is heated at 200° C. for 1 hour and then poured into vigorously stirred ice water. A product of 7-chloro-3-(2,6-difluorophenyl)-6-hydroxy-1,2-benzisoxazole precipitates and is filtered and dried. An analytical sample is recrystallized from toluene, mp 216°-220° C.

Analysis: Calculated for $C_{13}H_6ClF_2NO_2$: 55.43%C; 2.15%H; 4.97%N. Found: 55.59%C; 2.29%H; 4.96%N.

e. A mixture of 1.18 g of NaH and 9.2 g of 7-chloro-3-(2,6-difluorophenyl)-6-hydroxy-1,2-benzisoxazole in 15 ml of DMF is stirred 1 hour. A solution of 6.06 g of ethyl bromoacetate in 40 ml of DMF is added thereto dropwise and stirred for one half hour. Ten milliliters of 50% NaOH is added and the reaction mixture is warmed to 80° C. for 1 hour. Concentrated HCl is added to the warm solution until acidic. Water is added and {7-chloro-3-(2,6-difluorophenyl)-1,2-benzisoxazol-6-yl]oxy}acetic acid precipitates which is filtered, dried and recrystallized from toluene-acetonitrile to give a product having a melting point of 170°-172° C.

Analysis: Calculated for $C_{15}H_8ClF_2NO_4$: 53.04%C; 2.37%H; 4.12%N. Found: 53.17%C; 2.38%H; 4.18%N.

EXAMPLE 21 a. A mixture of 20.36 g of α-fluorocinnamoyl chloride and 14.4 g of AlCl$_3$ in 100 ml of 1,2-dichloroethane is stirred 1 hour followed by the dropwise addition of 17.7 g of 2,3-dichloroanisole in 100 ml of 1,2-dichloroethane. The reaction mixture is warmed to approximately 80° C. for 1 hour and poured over 100 ml of concentrated HCl and ice. The aqueous layer is extracted with CHCl$_3$ and the combined organic layer washed with water, dried over Na$_2$SO$_4$ and evaporated to a solid residue. The residue is triturated with hexane to give 4-(trans-α-fluorocinnamoyl)-2,3-dichloroanisole. A sample is recrystallized from toluene, mp 137°-138° C.

Analysis: Calculated for $C_{16}H_{11}Cl_2FO_2$: 59.10%C; 3.41%H; 5.84%F. Found: 59.38%C; 3.46%H; 5.86%F.

b. A mixture of 26.6 g of 4-(trans-α-fluorocinnamoyl)-2,3-dichloroanisole and 22.7 g of hydroxylamine HCl is refluxed 18 hours. The pyridine is evaporated in vacuo and the residue triturated with 5% HCl. A product is filtered off, dried and rinsed with ether-hexane giving a mixture of isomers. A sample of 4-(trans-α-fluorocinnamoyl)-2,3-dichloroanisole oxime is recrystallized from ethanol, mp 222°-238° C.

Analysis: Calculated for $C_{16}H_{12}Cl_2FNO_2$: 56.49%C; 3.56%H; 4.12%N. Found: 56.47%C; 3.51%H; 4.02%N.

c. A mixture of 0.43 g of NaH and 4 g of 4-trans-α-fluorocinnamoyl)-2,3-dichloroanisole oxime in 60 ml of DMF is stirred for one half hour and poured into ice water. A precipitate which formed is filtered and dried giving 7-chloro-3-(trans-β-fluorostyryl)-6-methoxy-1,2-benzisoxazole. Recrystallization from toluene gives a pure product, mp 155°-161° C.

Analysis: Calculated for $C_{16}H_{11}ClFNO_2$: 63.27%C; 3.65%H; 4.61%N. Found: 63.18%C; 3.42%H; 4.65%N.

d. A mixture of 1.4 g of 7-chloro-3-(trans-β-fluorostyryl)-6-methoxy-1,2-benzisoxazole and 5.6 g of pyridine HCl is heated at 200° C. for 1 hour and then poured into vigorously stirring ice water. A product of 7-chloro-3-(trans-β-fluorostyryl)-6-hydroxy-1,2-benzisoxazole precipitates and is filtered and dried, mp 226°-229° C.

Analysis: Calculated for $C_{15}H_9ClFNO_2$: 62.19%C; 3.13%H; 4.84%N. Found: 62.43%C; 3.17%H; 4.92%N.

e. To a mixture of 0.84 g of NaH in 100 ml of DMF, 6.77 g of 7-chloro-3-(trans-β-fluorostyryl)-6-hydroxy-1,2-benzisoxazole in 50 ml of DMF is added dropwise in an atmosphere of N$_2$. The mixture is stirred 1 hour and then 4.2 g of ethyl bromoacetate is added dropwise thereto. The reaction mixture is stirred for one half hour and fifteen milliliters of 50% NaOH is added and the reaction mixture warmed to 80° C. for 1 hour. The reaction mixture is made acidic with concentrated HCl and a product precipitates by the addition of water. The crude product is filtered, dried and recrystallized from 95% ethanol giving 7-chloro-3-(trans-β-fluorostyryl)-1,2-benzisoxazol-6-yl]oxy acetic acid, mp 200°-203° C.

Analysis: Calculated for $C_{17}H_{11}ClFNO_4$: 58.72%C; 3.18%H; 4.03%N. Found: 59.03%C; 3.29%H; 4.01%N.

EXAMPLE 22 a. To a solution of 52.23 g of 2,4-difluorobenzoylchloride in 200 ml of 1,2-dichloroethane, 40 g of AlCl$_3$ is added over a 30 minute period. A solution of 48.3 g of 2,3-dichloroanisole in 100 ml 1,2-dichloroethane is added dropwise. There is a slow evolution of gas and the temperature rises to approximately 30° C. The reaction mixture is warmed to 43° C. and the gas continues to evolve for approximately 30 minutes. The mixture is poured over concentrated HCl and ice. The organic layer is separated and the aqueous layer is extracted two times with CHCl$_3$. The combined organic layers are washed with water, dried (Na$_2$SO$_4$) and evaporated to give an oil. Trituration with hexane yields 2,3-dichloro-4-methoxy-2',4'-difluorobenzophenone which is recrystallized from ether, mp 139°-141° C.

Analysis: Calculated for $C_{14}H_8Cl_2F_2O_2$: 53.02%C; 2.54%H; 11.98%N. Found: 53.09%C; 2.43%H; 11.84%N.

b. To 67 g of 2,3-dichloro-4-methoxy-2',4'-difluorobenzophenone in 300 ml of pyridine is added 58 g of hydroxylamine HCl and the resultant mixture is refluxed for 18 hours. The pyridine is evaporated in vacuo and the residue is partitioned between 5% HCl and ethyl acetate. The ethylacetate extract is washed with water, dried over Na$_2$SO$_4$ and evaporated to give 2,3-dichloro-4-methoxy-2',6'-difluorobenzophenone oxime as a mixture of isomers. A sample is recrystallized from 95% ethanol, mp 180°-186° C.

Analysis: Calculated for $C_{14}H_9Cl_2F_2NO_2$: 50.62%C; 2.73%H; 4.22%N. Found: 50.63%C; 2.80%H; 4.55%N.

c. To a mixture of 5.7 g of NaH in 100 ml of DMF, a solution of 53 g of 2,3-dichloro-4-methoxy-2',6'-difluorobenzophenone oxime in 250 ml of DMF is added dropwise maintaining the temperature at approximately 30° C. After the mixture is stirred for one and one half hours, a product is precipitated by the addition of water. The crude product, which is a mixture of isomers, is chromatographed on silica gel with toluene-hexane as eluant to obtain a pure product of 7-chloro-3-(2,4-difluorophenyl)-6-methoxy-1,2-benzisoxazole which is recrystallized from toluene, mp 189°-191° C.

Analysis: Calculated for $C_{14}H_8ClF_2NO_2$: 56.87%C; 2.73%H; 4.74%N. Found: 56.94%C; 2.77%H; 4.66%N.

d. A solid mixture of 7.1 g of 7-chloro-3-(2,4-difluorophenyl)-6-methoxy-1,2-benzisoxazole and 27.8 g of pyridine HCl is heated at 200° C. for one hour and the mixture poured into vigorously stirred ice water to precipitate a product. The product is filtered and dried giving 7-chloro-3-(2,4-difluorophenyl)-6-hydroxy-1,2- benzisoxazole which is recrystallized from toluene, mp 186°-190° C.

Analysis: Calculated for $C_{13}H_6ClF_2NO_2$: 55.43%C; 2.15%H; 4.97%N. Found: 55.68%C; 2.16%H; 4.92%N.

e. To a mixture of 0.86 g of NaH in 100 ml of DMF, under $N_2$, a solution of 6.9 g of 7-chloro-3-(2,4-difluorophenyl)-6-hydroxy-1,2-benzisoxazole in 50 ml of DMF is added dropwise followed by the addition of 4.41 g of ethyl bromoacetate in 25 ml of DMF. The mixture is stirred for one half hour and fifteen milliliters of 50% NaOH is added and the mixture warmed for 1 hour at 80°-85° C. Concentrated HCl is then added until the mixture is acidic. {[7-chloro-3-(2,4-difluorophenyl)-1,2-benzisoxazol-6-yl]oxy}acetic acid is precipitated by the addition of water and recrystallized from toluene-acetonitrile, mp 200°-203° C.

Analysis: Calculated for $C_{15}H_8ClF_2NO_4$: 53.04%C; 2.37%H; 4.12%N. Found: 53.24%C; 2.55%H; 4.39%N.

EXAMPLE 23 a. Dimethylsulfate (94.64 g) is added dropwise over a 40 minute period to a cooled stirred solution of 2,5-dichlorophenol (122.25 g) and sodium hydroxide (31.5 g) in water (300 ml). This mixture is stirred at room temperature for one hour, then at reflux for 2 hours, then cooled to room temperature. The organic layer is separated and combined with ether extracts of the remaining aqueous layer. The ether solution is dried (saturated NaCl, $Na_2SO_4$, $K_2CO_3$) and the ether removed to give 2,5-dichloroanisole. Distillation gives a colorless liquid (115° C. at aspirator vacuum).

A solution of o-fluorobenzoyl chloride (69.76) in carbon disulfide (25 ml) is added at room temperature to a suspension of aluminum chloride (58.67 g) in carbon disulfide (450 ml) followed by the addition at room temperature of 70.81 g of 2,5-dichloroanisole in carbon disulfide (25 ml). The mixture is stirred 4 hours at room temperature, during which time a precipitate forms. The mixture is then refluxed for one hour, cooled, and 58 g of $AlCl_3$ is added. The resultant mixture is then refluxed for 2 hours and stirred at room temperature for 18 hours. The mixture is poured over ice/HCl and extracted with methylene dichloride to give an oil. Trituration with hexane-ether gives a solid. Recrystallization from diisopropyl ether gives a solid, melting partially at about 94° C. then at about 120° C. The solid remaining after removal of the solvent from the filtrate is treated with ether-petroleum ether to give 2,5-dichloro-4-(2-fluorobenzoyl)anisole and recrystallization from methanol gives mp 100°-103° C.

Analysis: Calculated for $C_{14}H_9Cl_2FO_2$: 56.21%C; 3.04%H. Found: 56.26%C; 3.00%H.

b. A mixture of 2,5-dichloro-4-(2-fluorobenzoyl)anisole (3 g) and hydroxylamine hydrochloride (1.4 g) in pyridine (25 ml) is refluxed for several hours until no ketone remains. The pyridine is removed under high vacuum and the residue diluted with water, then extracted with chloroform. The chloroform solution is dried and the chloroform removed to give a solid which is recrystallized from ether to afford (z)-2'-fluoro-2,5-dichloro-4-methoxybenzophenone oxime, mp 188° C.

Analysis: Calculated for $C_{14}H_{10}Cl_2FNO_2$: 53.52%C; 3.21%H; 4.46%N. Found: 53.44%C; 3.22%H; 4.36%N.

c. A solution of (z)-2'-fluoro-2,5-dichloro-4-methoxybenzophenone oxime (3.14 g) in DMF (20 ml) is added dropwise to a stirred suspension of sodium hydride (0.6 g) in DMF (20 ml). The mixture is stirred 18 hours at room temperature, then poured into ice/water and extracted with chloroform. The chloroform solution is washed with water, saturated sodium chloride and dried over $Na_2SO_4$—$MgSO_4$. Removal of the chloroform gives a residue that on treatment with ether-petroleum ether gives a solid, mp 165°-166° C. Removal of the solvent from the filtrate yields a solid that on treatment with ether-petroleum ether gives 5-chloro-3-(2-fluorophenyl)-6-methoxy-1,2-benzisoxazole, mp 165°-166° C.

Analysis: Calculated for $C_{14}H_9ClFNO_2$: 60.55%C; 3.27%H; 5.04%H; 12.77%Cl. Found: 60.71%C; 3.14%H; 4.99%N; 12.75%Cl.

d. A solution of 5-chloro-3-(2-fluorophenyl)-6-methoxy-1,2-benzisoxazole (1 g) and boron tribromide (1.3 ml) in dichloroethane (30 ml) is refluxed for about 24 hours. The reaction mixture is poured onto ice-water and extracted with dichloromethane to give a solid of 5-chloro-3-(2-fluorophenyl)-6-hydroxy-1,2-benzisoxazole, mp 180°-182° C.

Analysis: Calculated for $C_{13}H_7FClNO_2$: 59.22%C; 2.68%H; 5.31%N. Found: 58.90%C; 2.68%H; 5.17%N.

e. A solution of 5-chloro-3-(2-fluorophenyl)-6-hydroxy-1,2-benzisoxazole (14.8 g) in DMF (40 ml) is added dropwise at room temperature to a suspension of sodium hydride (3.0 g) in DMF (40 ml) and the mixture is stirred at room temperature for one half hour. A solution of ethyl bromoacetate (10.31 g) in DMF (40 ml) is then added dropwise and the mixture stirred 18 hours at room temperature. An additional 0.3 g of NaH suspended in DMF is added, followed by 1 g of ethyl bromoacetate. The mixture is warmed to 50° C. for 1 and one half hours, cooled and poured over ice/water and extracted with ether. The ether extracts are washed with water, saturated sodium chloride, dried over sodium sulfate and the solvent is removed to give a solid. Trituration with ether-petroleum ether (1:1) gives ethyl{[5-chloro-3-(2-fluorophenyl)-1,2-benzisoxazol-6-yl]oxy}acetate, mp 114°-115° C.

Analysis: Calculated for $C_{17}H_{13}ClFNO_4$: 58.37%C; 3.75%H; 4.00%N. Found: 58.15%C; 3.66%H; 3.93%N.

f. A mixture of ethyl{[5-chloro-3-(2-fluorophenyl)-1,2-benzisoxazol-6-yl]oxy}acetate (14 g) sodium hydroxide (8 g), ethanol (500 ml) and water (300 ml) is refluxed for five hours, cooled in an ice bath and acidified with concentrated hydrochloric acid. The suspension is extracted with chloroform, the extract dried with saturated sodium chloride and the chloroform removed to give a solid, mp 214°-215° C. Recrystallization from a 3:2 mixture of acetonitrile-toluene gives {[5-chloro-3-(2-fluorophenyl)-1,2-benzisoxazol-6-yl]oxy}acetic acid.

Analysis: Calculated for $C_{15}H_9ClFNO_4$: 56.00%C; 2.82%H; 4.35%N. Found: 55.79%C; 2.69%H; 4.27%N.

EXAMPLE 24 a. To a solution of 57.6 g of 3,4-dichlorobenzoylchloride in 1,2-dichloroethane (150 ml) is added 36.7 g of $AlCl_3$ in portions over a 30 minute period. To the resultant mixture is added dropwise 44.26 g of 2,3-dichloroanisole in 1,2-dichloroethane (150 ml). There is an evolution of gas and the reaction mixture is heated to 60° C. for one hour. The mixture is then poured over 150 ml of concentrated HCl and 150 ml of ice and then extracted with $CHCl_3$ and then ethanol. The resultant organic layer is washed with 10% aqueous $K_2CO_3$, then water, dried over ($Na_2SO_4$) and evaporated to yield 2,3-dichloro-4-methoxy-3',4'-dichlorobenzophenone, mp 113°-140° C.

b. A mixture of 53 g of 2,3-dichloro-4-methoxy-3',4'-dichlorobenzophenone and 40 g AlCl$_3$ in 400 ml of benzene is refluxed for five hours and then cooled to room temperature and maintained there for about 18 hours. The mixture is then poured over 200 ml of concentrated HCl and 200 ml of ice and then stirred at room temperature for one half hour. Ethylacetate is added to the mixture and the ethyl acetate/benzene layer is washed with water, dried over Na$_2$SO$_4$ and then evaporated to yield 2,3-dichloro-4-hydroxy-3',4'-dichlorobenzophenone, mp 179°–180° C.

c. A mixture of 35.43 g of 2,3-dichloro-4-hydroxy-3',4'-di-chlorobenzophenone, and 15.29 g of hydroxylamine HCl in 300 ml of pyridine is refluxed for 2 hours. The pyridine is evaporated in vacuo. The residue partitioned between ethylacetate and 5% HCl. The extract is washed with water, dried over Na$_2$SO$_4$ and evaporated to give the corresponding oxime.

To a solution of 35 g of the oxime in 300 ml of DMF, 6.0 g of NaH is added and the mixture heated to an internal temperature of 103° C. for one hour 45 minutes followed by 100° C. internal temperature for three fourths of an hour. The reaction mixture is cooled to room temperature and a solution of 18.37 g of ethyl bromoacetate in 50 ml of DMF is added dropwise. The mixture is stirred for about 64 hours, poured over water and the precipitate which forms is filtered off and rinsed with hexane. A crude product is recrystallized from ethanol to give ethyl{[7-chloro-3-(3,4-dichlorophenyl)-1,2-benzisoxazol-6-yl]oxy}acetate, mp 123°–125° C.

To a suspension of 19 g of the ester in 400 ml of ethanol, 20 ml of 50% NaOH is added. A precipitate forms and the heterogeneous mixture is refluxed for 1 hour. To the hot mixture 400 ml of water is added followed by concentrated HCl until the mixture is acidic. The suspension is stirred one half hour, filtered and recrystallized from DMF-ethylacetate to give {[7-chloro-3-(3,4-dichlorophenyl)-1,2-benzisoxazol-6-yl]oxy}acetic acid, mp 222°–224° C.

Analysis: Calculated for C$_{15}$H$_8$Cl$_3$NO$_4$: 48.35%C; 2.16%H; 3.76%N. Found: 58.40%C; 2.03%H; 3.93%N.

EXAMPLE 25 a. The Friedel-Crafts procedure of Example 24a is repeated with 48.13 g of o-chlorobenzoyl chloride being combined with 36.7 g AlCl$_3$ and 44.26 g of 2,3-dichloroanisole to yield a white crystalline product of 2,3-dichloro-4-methoxy-2'-chlorobenzophenone, mp 117°–120° C.

b. The procedure of Example 24b is repeated except that 68 g of 2,3-dichloro-4-methoxy-2'-chlorobenzophenone is combined with 58.6 g of AlCl$_3$ in 500 ml of benzene. The resultant product is recrystallized from toluene to yield 2,3-dichloro-4-hydroxy-2'-chlorobenzophenone, mp 74°–77° C.

c. To a solution of 53 g of 2,3-dichloro-4-hydroxy-2'-chlorobenzophenone in 350 ml of pyridine, 25.02 g of hydroxylamine HCl is added. The mixture is refluxed 2 hours. The pyridine is evaporated in vacuo, the residue partioned between ethyl acetate and 5% HCl. The ethyl acetate extract is washed with water, dried over Na$_2$SO$_4$ and evaporated to give the corresponding oxime. To a solution of 49 g of the oxime in 300 ml of DMF, 9.12 g of NaH is added and the mixture heated to an internal temperature of 80°–84° C. for 1 hour. The reaction mixture is cooled to room temperature and a solution of 27.5 g of ethyl bromoacetate in 50 ml of DMF is added dropwise. The mixture is stirred one half hour and water added to decompose excess NaH. The product is extracted with ethyl acetate. The ethyl acetate extract is washed with 10% NaOH and water, dried over Na$_2$SO$_4$ and evaporated to give a mixture. Chromatography of the mixture on silica gel with CHCl$_3$ as eluant yields ethyl{[7-chloro-3-(2-chlorophenyl)-1,2-benzisoxazole-6-yl]oxy}acetate.

To a solution of 5.86 g of the ester in 200 ml of hot ethanol, 6 ml of 50% NaOH is added. A precipitate forms and the suspension is refluxed for one hour. Two hundred milliliters of water are added to the mixture and enough concentrated HCl to make the mixture acidic. The mixture is and enough concentrated HCl to make the mixture acidic. The mixture is stirred 18 hours at room temperature. A solid product precipitates out and is filtered and recrystallized from toluene giving {[7-chloro-3-(2-chlorophenyl)-1,2-benzisoxazol-6-yl]oxy}acetic acid, mp 165°–168° C.

Analysis: Calculated for C$_{15}$H$_9$Cl$_2$NO$_4$: 53.28%C; 2.68%C; 2.68%H; 4.14%N. Found: 53.50%C; 2.67%H; 3.95%N.

EXAMPLE 26 a. The Friedel-Crafts procedure of Example 24a is repeated with 35.4 g of 2,3-dichloroanisole, 32.4 g of o-toluoyl chloride and 28 g of AlCl$_3$ being combined in 125 ml of 1,2-dichloroethane to yield a product of 2,3-dichloro-4-methoxy-2'-methylbenzophenone.

b. The procedure of Example 24b is repeated except that 38 g of 2,3-dichloro-4-methoxy-2'-methylbenzophenone is combined with 34.6 g of AlCl$_3$ in 300 ml of benzene. The resultant product is recrystallized from toluene to yield 2,3-dichloro-4-hydroxy-2'-methylbenzophenone.

c. To a solution of 28 g of 2,3-dichloro-4-hydroxy-2'-methylbenzophenone in 250 ml of pyridine, 13.9 g of hydroxylamine HCl is added and the mixture is refluxed 48 hours. The pyridine is evaporated in vacuo and the residue is partitioned between ethyl acetate and 5% HCl. The ethylacetate extract is washed with water, dried over Na$_2$SO$_4$ and evaporated to give the corresponding oxime. To a solution of 12 g of the oxime in 50 ml of DMF and 50 ml of toluene, 2.43 g of NaH is added. The mixture is heated under N$_2$ to an internal temperature of 95°–98° C. for 5 and one quarter hours. An additional 50 ml of DMF is added and the internal temperature held at 95° C. for another two hours. The reaction mixture is cooled to 30° C. and 7.5 g of ethyl bromoacetate is added dropwise. After addition is complete the mixture is stirred one hour. Water is added and the product extracted ethylacetate, dried over Na$_2$SO$_4$ and evaporated to give ethyl[7-chloro-3-(2-tolyl)-1,2-benzisoxazol-6-yl]oxy acetate.

To a solution of 13.95 g of the ester in 500 ml of hot ethanol, 13 ml of 50% NaOH is added. A precipitate forms and the suspension is refluxed one and one half hours. Five hundred milliliters of water is added followed by the addition of concentrated HCl until the mixture is acidic. A solid product precipitates on cooling and the product is filtered off and recrystallized from toluene giving {[7-chloro-3-(2-tolyl)-1,2-benzisoxazol-6-yl]oxy}acetic acid, mp 179°–181° C.

Analysis: Calculated for C$_{16}$H$_{12}$ClNO$_4$: 60.48%C; 3.81%H; 4.41%N. Found: 60.76%C; 3.91%H; 4.26%N.

EXAMPLE 27 a. The Friedel-Crafts procedure of Example 24a is repeated with 33.7 g of 2,3-dimethylbenzoyl chloride, 54 g of 2,3-dichloroanisole and 26.7 AlCl₃ being reacted to form 2,3-dichloro-4-methoxy-2',3'-dimethylbenzophenone.

b. The procedure of Example 24b is repeated with 39 g of 2,3-dichloro-4-methoxy-2',3'-dimethylbenzophenone in 300 ml of benzene. The resultant product is recrystallized from toluene to yield 2,3-dichloro-4-hydroxy-2',3'-dimethylbenzophenone.

c. A mixture of 31 g of 2,3-dichloro-4-hydroxy-2',3'-dimethylbenzophenone and 30.5 g of hydroxylamine hydrochloride in 250 ml of pyridine is refluxed for about one week. The pyridine is evaporated in vacuo and the residue is partitioned between ethyl acetate and 5% HCl. The ethylacetate extract is washed, dried over Na₂SO₄ and evaporated. Trituration with hexane gives 2,3-dichloro-4-hydroxy-2',3'-dimethylbenzophenone oxime.

d. To a solution of 5 g of 2,3-dichloro-4-hydroxy-2',3'-dimethylbenzophenone oxime in 70 ml of DMF, 0.96 g of NaH is added. The internal temperature is held between 95°–120° C. for seven hours, then the mixture is heated at 130° C. for 1.5 hours. The reaction mixture is cooled and 2.94 g of ethyl bromoacetate is added dropwise. The mixture is stirred one hour and water is added dropwise. The product which forms is filtered off and recrystallized from 95% ethanol to yield ethyl-{[7-chloro-3-(2,3-dimethylphenyl)-1,2-benzisoxazol-6-yl]oxy}acetate, mp 89°–91° C.

Analysis: Calculated for $C_{19}H_{18}ClNO_4$: 63.42%C; 5.04%H; 3.89%N. Found: 63.25%C; 5.02%H; 3.79%N.

e. A suspension of 2 g of ethyl{[7-chloro-3-(2,3-dimethylphenyl)-1,2-benzisoxazol-6-yl]oxy}acetate, 50 ml of ethanol and 5 ml of 50% NaOH is refluxed 1 hour. To the hot mixture 50 ml of water is added enough concentrated HCl to make the reaction mixture acidic. Upon cooling and adding water, {[7-chloro-3-(2,3-dimethylphenyl)-1,2-benzisoxazol-6-yl]oxy}acetic acid is precipitated, mp 170°–172° C.

Analysis: Calculated for $C_{17}H_{14}ClNO_4$: 61.54%C; 4.25%H; 4.22%N. Found: 61.65%C; 4.38%H; 4.01%N.

EXAMPLE 28 a. 29.3 g of 2-bromopyridine in 150 ml of dry THF is added to 75 ml of 2.6M n-butyllithium that was chilled to −65° C. 2,3-dichloro-4-methoxybenzaldehyde (38.0 g) is then added in 300 ml of THF and the reaction mixture allowed to come to room temperature. It is poured into H₂O and the crystalline product filtered off, washed with ether and dried to give α-(2,3-dichloro-4-methoxyphenyl)-2-pyridinemethanol, mp 174°–176° C.

b. α-(2,3-dichloro-4-methoxyphenyl)-2-pyridinemethanol (31.86 g) is dissolved in 600 ml of acetic acid and 100 ml of H₂O. Chromic anhydride (11.0 g) is added portionwise over five minutes. After three hours the reaction mixture is poured into H₂O and extracted with ether. The combined organic phase is washed well with 10% NaHCO₃, then brine and dried. Removal of the solvent under reduced pressure gives a crystalline product of (2,3-dichloro-4-methoxyphenyl)(2-pyridyl)methanone, mp 104°–107° C.

Analysis: Calculated for $C_{13}H_9Cl_2NO_2$: 55.34%C; 3.21%H; 4.97%N. Found: 55.29%C; 3.26%H; 4.93%N.

c. (2,3-dichloro-4-methoxyphenyl)(2-pyridyl)methanone (32.0 g) is refluxed for four hours in 300 ml of ethanol containing 30 g of hydroxylamine hydrochloride. The reaction mixture is poured into H₂O, made basic with NH₄OH and extracted with ethyl acetate. Drying and evaporation gives a crude oxime mixture of E-(2-pyridyl)(2,3-dichloro-4-methoxyphenyl)methanone oxime and Z-(2-pyridyl)(2,3-dichloro-4-methoxyphenyl)methanone oxime.

The oxime mixture is dissolved in 200 ml of DMF and added to a suspension of 3.1 g NaH in 150 ml of DMF. After 15 minutes the reaction mixture is poured into H₂O and the product filtered off. One recrystallization from isopropanol removes unreacted E-oxime, giving 7-chloro-6-methoxy-3-(2-pyridyl)-1,2-benzisoxazole, mp 164°–166° C.

Analysis: Calculated for $C_{13}H_9ClN_2O_2$: 59.89%C; 3.48%H; 10.75%N. Found: 59.53%C; 3.37%H; 10.63%N.

d. 7-chloro-6-methoxy-3-(2-pyridyl)-1,2-benzisoxazole (24.4 g) is refluxed for 1.5 hours in 450 ml of 48% HBr. The precipitated hydrobromide salt is filtered off, washed with ether and neutralized with 10% NaHCO₃ solution. The free base is filtered off and dried, giving 7-chloro-6-hydroxy-3-(2-pyridyl)-1,2-benzisoxazole, mp 209°–211° C.

Analysis: Calculated for $C_{12}H_7ClN_2O_2$: 58.43%C; 2.85%H; 11.36%N. Found: 58.16%C; 2.81%H; 11.42%N.

e. 7-chloro-6-hydroxy-3-(2-pyridyl)-1,2-benzisoxazole (10.0 g) is dissolved in 80 ml of DMF and added to an ice cold suspension of NaH (1.1 g) in 50 ml of DMF. When hydrogen evolution ceases, ethyl bromoacetate (7.5 g) in 20 ml of DMF is added. After an additional 90 minutes, 200 ml of H₂O and 10 ml of 50% NaOH are added and the reaction warmed at 65° C. for 45 minutes. The mixture is poured into H₂O, acidified to pH 1–2, and a solid product filtered and dried to give {[7-chloro-3-(2-pyridyl)-1,2-benzisoxazole-6-yl]oxy}acetic acid, mp 255°–256° C.

Analysis: Calculated for $C_{14}H_9ClN_2O_4$: 55.18%C; 2.48%H; 9.20%N. Found: 55.35%C; 2.88%H; 9.45%N.

EXAMPLE 29 a. 7-chloro-6-hydroxy-3-(2-pyridyl)-1,2-benzisoxazole, Example 28d, (9.9 g) is dissolved in 600 ml of glacial acetic acid at 60° C. m-chloroperbenzoic acid (8.3 g of 85%) is then added portionwise. After warming at 60° C. for a total of 14 hours the reaction mixture is poured into 2 l of H₂O and the product filtered off and washed with methanol, then ether. Obtained in this manner is 7-chloro-6-hydroxy-3-(2-pyridyl)-1,2-benzisoxazole 1'-oxide in the form of a hemihydrate after recrystallization from DMF/H₂O, mp 214° C.

Analysis: Calculated for $C_{12}H_7ClN_2O_3 \cdot 0.5H_2O$: 53.05%C; 2.97%H; 10.31%N. Found: 53.14%C; 2.82%H; 10.47%N.

b. 7-chloro-6-hydroxy-3-(2-pyridyl)-1,2-benzisoxazole 1'-oxide (7.30 g) is dissolved in 200 ml of DMF and added to a suspension of NaH (1.33 g) in 50 ml of DMF. After 15 minutes ethyl bromoacetate (5.0 g) in 20 ml of DMF is added and the reaction is warmed at 50° C. for 10 hours. The reaction mixture is quenched with H₂O, acidified and the precipitate filtered off and dried well. The precipitate is treated again with 1.33 g of NaH and 5.0 g of ethyl bromoacetate in DMF. After 30 minutes 200 ml of H₂O and 10 ml of 50% NaOH are added and the reaction mixture is warmed at 50° C. for 30 minutes. It is then acidified and {[7-chloro-3-(2-pyridyl)-1,2-benzisoxazol-6-yl]oxy}acetic acid 1'-oxide is obtained, mp 214° C. (d).

Analysis: Calculated for $C_{14}H_9ClN_2O_5$: 52.43%C; 2.83%H; 8.74%N. Found: 52.35%C; 2.79%H; 8.93%N.

EXAMPLE 30 a. m-dimethoxybenzene (27.6 g) and o-fluorobenzoyl chloride (31.7 g) are dissolved in 200 ml of dichloroethane and AlCl$_3$ (28.0 g) is added portionwise. After two hours an additional 56 g of AlCl$_3$ is added and the reaction mixture warmed at 60° C. for 1.5 hours. It is then poured into H$_2$O and extracted with ethylacetate. Drying and evaporation gives a crystalline compound. Trituration with toluene gives 2,4-dihydroxy-2'-fluorobenzophenone, mp 109°–111° C.

Analysis: Calculated for C$_{13}$H$_9$FO$_3$: 67.24%C; 3.91%H; 8.18%F. Found: 66.85%C; 3.75%H; 8.35%F.

b. 2,4-dihydroxy-2'-fluorobenzophenone (25.0 g) is refluxed 18 hours in 250 ml of pyridine containing 17.1 g of hydroxylamine hydrochloride. The reaction mixture is then partitioned between ether and 5% HCl and the organic layer is separated. Drying and evaporation gives, after crystallization from toluene, one pure isomer of 2,4-dihydroxy-2'-fluorobenzophenone [E-oxime], mp 170°–172° C.

Analysis: Calculated for C$_{13}$H$_{10}$FNO$_3$: 63.16%C; 4.08%H; 5.67%N. Found: 63.56%C; 4.28%H; 5.56%N.

c. The E-oxime 2,4-dihydro-2'-fluorobenzophenone oxime (18.6 g) is warmed at 50° C. in 18.0 ml of acetic anhydride for 5 hours then at 60° C. for 6 hours. An additional 3.0 ml of acetic anhydride is added and the reaction is allowed to remain undisturbed at room temperature for about 73 hours. The crystalline product which separates from the reaction mixture is washed with cold ether to give a pure product of E-4-acetoxy-2-hydroxy-2'-fluorobenzophenone O-acetyl oxime, mp 132°–134° C.

Analysis: Calculated for C$_{17}$H$_{14}$FNO$_5$: 61.63%C; 4.26%H; 4.23%N. Found: 61.80%C; 4.08%H; 4.07%N.

d. E-4-acetoxy-2-hydroxy-2'-fluorobenzophenone O-acetyloxime (18.4 g) is dissolved in 80 ml of DMF and added to an ice-cold suspension of NaH (3.3 g) in 100 ml of DMF. After 90 minutes the reaction mixture is poured into H$_2$O and a little insoluble precipitate is filtered off. Acidification of the aqueous filtrate and extraction with ether gives, after drying and evaporation, 3-(2-fluorophenyl)-6-hydroxy-1,2-benzisoxazole, mp 206°–210° C.

Calculated for C$_{13}$H$_8$FNO$_2$: 68.12%C; 3.52%H; 6.11%N. Found: 68.43%C; 3.59%H; 6.14%N.

e. 3-(2-fluorophenyl)-6-hydroxy-1,2-benzisoxazole (9.7 g) is dissolved in 80 ml of DMF and added to an ice-cooled suspension of NaH (1.4 g) in 50 ml of DMF. When hydrogen evolution stops, ethyl bromoacetate (7.5 g) in 20 ml of DMF is added and the reaction mixture is allowed to come to room temperature. After two hours 200 ml of H$_2$O and 10 ml of 50% NaOH are added and the reaction warmed at 50° C. After an additional 30 minutes a product is collected after acidification and filtering. Recrystallization from toluene/CH$_3$CN gives {[3-(2-fluorophenyl)-1,2-benzisoxazol-6-yl]oxy}acetic acid, mp 182°–184° C.

Analysis: Calculated for C$_{15}$H$_{10}$FNO$_4$: 62.72%C; 3.51%H; 4.88%N. Found: 62.56%C; 3.61%H; 5.06%N.

EXAMPLE 31 a. The Friedel-Crafts procedure of Example 24a is repeated with 31.55 g of p-fluorobenzoyl chloride, 32 g of 2,3-dichloroanisole and 35.22 g of AlCl$_3$ combined in 1,2-dichloroethane and reacted. The resultant crude product is triturated with warm hexane, cooled and filtered to yield 2,3-dichloro-4-methoxy-4'-fluorobenzophenone.

b. A mixture of 39.5 g of 2,3-dichloro-4-methoxy-4'-fluorobenzophenone and 160 g of pyridine hydrochloride is heated at 200° C. for one hour. The reaction mixture is poured into ice water with stirring and a precipitate forms. The precipitate is filtered and dried for about 18 hours to yield 2,3-dichloro-4-hydroxy-4'-fluorobenzophenone.

c. To a solution of 35 g of 2,3-dichloro-4-hydroxy-4'-fluorobenzophenone in 250 ml pyridine, 34.6 g of hydroxylamine HCl is added. The mixture is refluxed for 4 hours. The pyridine is evaporated in vacuo. The residue is partitioned between 5% HCl and ethyl acetate. The ethyl acetate extract is washed with water, dried over Na$_2$SO$_4$ and evaporated to give 2,3-dichloro-4-hydroxy-4'-fluorobenzophenone oxime as a mixture of isomers, mp 150°–156° C.

Analysis: Calculated for C$_{13}$H$_8$Cl$_2$FNO$_2$: 52.02%C; 2.69%H; 4.67%N. Found: 52.19%C; 2.74%H; 4.69%N.

d. To a mixture of 4.0 g NaH in 50 ml DMF, a solution of 20 g of 2,3-dichloro-4-hydroxy-4'-fluorobenzophenone oxime in 100 ml of DMF is added dropwise in an atmosphere of N$_2$. The reaction mixture is heated to an internal temperature of 96° C. for 2 hours. The reaction mixture is cooled to 40° C. and 12.3 g of ethyl bromoacetate is added dropwise and the mixture is stirred for one hour. Twenty milliliters of 50% NaOH and 100 ml of water is added and the reaction is heated at 80°–90° C. for one hour. Concentrated HCl is added until the reaction mixture is acidic and the mixture is stirred for one half hour and water added. A solid product is collected by filtration and recrystallized to give a pure product of {[7-chloro-3-(4-fluorophenyl)-1,2-benzisoxazol-6-yl]oxy}acetic acid, mp 233°–237° C.

Analysis: Calculated for C$_{15}$H$_9$ClFNO$_4$: 56.00%C; 2.83%H; 4.36%N. Found: 55.76%C; 2.90%H; 4.29%N.

EXAMPLE 32 a. 2,6-dimethoxytoluene (20.0 g) and o-fluorobenzoyl chloride (19.8 g) are dissolved in 250 ml of dichloroethane and chilled to 5° C. AlCl$_3$ is added portionwise and when the addition is complete the reaction mixture is allowed to warm to room temperature over 30 minutes, then refluxed 30 minutes. It is then poured into 5% HCl and allowed to stand undisturbed 18 hours. Extraction with ether, followed by drying and concentration, gives crystalline material that is washed with hexane to give 2'-fluoro-2-hydroxy-4-methoxy-3-methylbenzophenone, mp 118°–120° C.

Analysis: Calculated for C$_{15}$H$_{13}$FO$_3$: 69.22%C; 5.04%H; 7.30%F. Found: 69.23%C; 5.01%H; 6.98%F.

b. 2'-fluoro-2-hydroxy-4-methoxy-3-methylbenzophenone (30.0 g) is refluxed 18 hours in 350 ml of pyridine containing 32.0 g of hydroxylamine hydrochloride. The solvent is removed in vacuo and the residue is distributed between ether and 5% HCl. Drying and concentration of the ether gives a crude product that is heated as a melt at 200° C. for 30 minutes in a nitrogen atmosphere. The melt is allowed to cool and the solid mass is triturated well with hexane to give E-2'-fluoro-2-hydroxy-4-methoxy-3-methylbenzophenone oxime, mp 167°–169° C.

Analysis: Calculated for C$_{15}$H$_{14}$FNO$_3$: 65.44%C; 5.13%H; 5.09%N. Found: 65.49%C; 5.26%H; 4.83%N.

c. E-2'-fluoro-2-hydroxy-4-methoxy-3-methylbenzophenone oxime (20.0 g) is warmed on a steam bath for one hour with 12 ml of acetic anhydride. The acetic anhydride is evaporated in vacuo and the product is distributed between ether and H$_2$O, then the ether is washed with 10% NaHCO$_3$. Evaporation and trituration of the crystalline product with hexane gives E-2'-fluoro-2-hydroxy-4-methoxy-3-methylbenzophenone O-acetyl oxime, mp 83°–86° C.

Analysis: Calculated for C$_{12}$H$_{16}$FNO$_4$: 64.34%C; 5.08%H; 4.42%N. Found: 64.30%C; 5.08%H; 4.26%N.

d. E-2'-fluoro-2-hydroxy-4-methoxy-3-methylbenzophenone O-acetyl oxime (22.0 g) is dissolved in 100 ml of DMF and added to a suspension of 2.5 g NaH in 100 ml DMF. An ice bath is applied to keep the reaction temperature <30° C. After 40 minutes the reaction is poured into H$_2$O and extracted with ether. After washing well with H$_2$O, the ether is dried and evaporated to give a crystalline product that is washed with cold hexane to give 3-(2-fluorophenyl)-6-methoxy-7-methyl-1,2-benzisoxazole, mp 105°–108° C.

Analysis: Calculated for C$_{15}$H$_{12}$FNO$_2$: 70.03%C; 4.70%H; 5.45%N. Found: 69.96%C; 4.76%H; 3.36%N.

e. 3-(2-fluorophenyl)-6-methoxy-7-methyl-1,2-benzisoxazole (16.1 g) is heated at 200° C. for two hours with 64 g of pyridine hydrochloride. The melt is poured into H$_2$O and extracted with ethyl acetate. After washing with 5% HCl the ethyl acetate is dried and evaporated to give 3-(2-fluorophenyl)-6-hydroxy-7-methyl-1,2-benzisoxazole, mp 216°–219° C.

Analysis: Calculated for C$_{14}$H$_{10}$FNO$_2$: 69.13%C; 4.14%H; 5.76%N. Found: 68.91%C; 4.03%H; 5.82%N.

f. 3-(2-fluorophenyl)-6-hydroxy-7-methyl-1,2-benzisoxazole (10.6 g) is dissolved in 90 ml of DMF and treated with 8.0 g of ethyl bromoacetate and 6.7 g of K$_2$CO$_3$. The reaction is warmed at 60° C. for 2 hours then allowed to return to ambient. After 18 hours at ambient, water (200 ml) and 50% NaOH (15 ml) are added and the solution heated at 90° C. for 90 minutes. The mixture is poured into H$_2$O and acidified and then it is extracted into ether. Drying and evaporation gives crystalline product of {[3-(2-fluorophenyl)-7-methyl-1,2-benzisoxaol-6-yl]oxy}acetic acid, mp 158°–160° C.

Analysis: Calculated for C$_{16}$H$_{12}$FNO$_4$: 63.78%C; 4.02%H; 4.65%N. Found: 63.89%C; 4.06%H; 4.58%N.

EXAMPLE 33 a. m-chloroanisole (28.5 g) and o-fluorobenzoyl chloride (31.7 g) are dissolved in 200 ml of dichloroethane and treated at 10° C. with 26.7 g of AlCl$_3$. After 45 minutes the reaction mixture is poured over ice and extracted with ether. Drying and evaporation, followed by trituration with hexane gives material that contains 2-chloro-2'-fluoro-4-methoxybenzophenone. Recrystallization from Et$_2$O/hexane gives 2-chloro-2'-fluoro-4-methoxybenzophenone, mp 77°–79° C.

Analysis: Calculated for C$_{14}$H$_{10}$ClFO$_2$: 63.53%C; 3.81%H; 7.18%F. Found: 63.77%C; 3.75%H; 7.25%F.

b. 2-chloro-2'-fluoro-4-methoxybenzophenone (15.5 g) is refluxed for three hours in 150 ml of pyridine containing 10.0 g of hydroxylamine hydrochloride. The pyridine is removed in vacuo and the residue is distributed between ether and 5% HCl. Drying and evaporation of the organic phase gives an isomeric mixture of oximes. The mixture is dissolved in 50 ml of DMF and is added to a suspension of 1.5 g NaH in 30 ml of DMF. After warming at 60° C. for 30 minutes the reaction mixture is poured into H$_2$O and extracted with ether. Concentration under reduced pressure gives a solid. Recrystallization from ether gives 3-(2-fluorophenyl)-6-methoxy-1,2-benzisoxazole, mp 101°–103° C.

Analysis: Calculated for C$_{14}$H$_{10}$FNO$_2$: 69.13%C; 4.14%H; 5.76%N. Found: 69.08%C; 4.29%H; 5.65%N.

c. 10 g of 3-(2-fluorophenyl)-6-methoxy-1,2-benzisoxazole are dissolved in 400 ml of dry THF at −40° C. and treated with 21 ml of 2.2M n-butyllithium. After stirring for one hour, I$_2$ (11.7 g) in 90 ml of ether is added. The reaction mixture is poured into Na$_2$S$_2$O$_3$, then H$_2$O. Drying and concentration gives 3-(2-fluorophenyl)-7-iodo-6-methoxy-1,2-benzisoxazole, mp 135°–138° C.

Analysis: Calculated for: C$_{14}$H$_9$FINO$_2$: 45.55%C; 2.46%H; 3.80%N; 34.38%I. Found: 44.94%C; 2.43%H; 3.70%N; 34.09%I.

d. 3-(2-fluorophenyl)-7-iodo-6-methoxy-1,2-benzisoxazole (8.2 g) is refluxed 18 hours in 130 ml of CH$_2$Cl$_2$ containing 6.6 ml of BBr$_3$. The reaction mixture is poured into H$_2$O and extracted into ether. Drying and evaporation gives a crystalline product that is triturated well with hexane to yield 3-(2-fluorophenyl)-6-hydroxy-7-iodo-1,2-benzisoxazole, mp 212°–214° C.

Analysis: Calculated for C$_{13}$H$_7$FINO$_2$: 43.97%C; 1.99%H; 3.95%N; 35.74%I. Found: 44.19%C; 2.00%H; 3.86%N; 35.12%I.

e. 3-(2-fluorophenyl)-6-hydroxy-7-iodo-1,2-benzisoxazole (7.80 g) in 80 ml of DMF is treated at 60° C. with 6.6 g of K$_2$CO$_3$ and 7.9 g of ethyl bromoacetate. After one hour the temperature is increased to 90° C. and 80 ml of H$_2$O and 8 ml of 50% NaOH are added. After an additional 30 minutes the mixture is poured into H$_2$O and acidified and then extracted into ether, dried and evaporated to yield {[3-(2-fluorophenyl)-7-iodo-1,2-benzisoxazol-6-yl]oxy}acetic acid, mp 178°–180° C.

Analysis: Calculated for C$_{15}$H$_9$FINO$_4$: 43.61%C; 2.20%H; 3.39%N. Found: 43.25%C; 2.12%H; 3.28%N.

EXAMPLE 34 a. 10 g of 3-(2-fluorophenyl)-6-methoxy-1,2-benzisoxazole of Example 33b are dissolved in 400 ml of dry THF and treated at −40° C. with 21 ml of 2.2M n-butyllithium. After stirring for one hour, bromine (2.5 ml) is added dropwise. The reaction mixture is poured into H$_2$O, extracted into ether and washed with Na$_2$S$_2$O$_3$ solution. Drying and evaporating gives a material that contains the desired brominated product, 7-bromo-3-(2-fluorophenyl)-6-methoxy-1,2-benzisoxazole, mp 150°–153° C.

Analysis: Calculated for C$_{14}$H$_9$BrFNO$_2$: 52.19%C; 2.82%H; 4.35%N; 24.81%Br. Found: 51.97%C; 2.83%H; 4.28%N; 25.17%Br.

b. 7-bromo-3-(2-fluorophenyl)-6-methoxy-1,2-benzisoxazole (7.20 g) is refluxed for 18 hours in 130 ml of CH$_2$Cl$_2$ containing 6.6 ml of BBr$_3$. The reaction mixture is poured into H$_2$O and extracted into ethyl acetate. Evaporation and trituration with hexane gives the corresponding phenol, mp 231°–234° C.

The phenol (6.30 g) in 80 ml of DMF is treated at 60° C. with 6.6 g of K$_2$CO$_3$ and 7.9 g of ethyl bromoacetate. After one hour, 80 ml of H$_2$O and 8 ml of 50% NaOH are added and the temperature is raised to 90° C. After an additional 45 minutes the reaction is acidified and extracted into ethylacetate. Evaporation and recrystallization from toluene/CH$_2$CN gives {[7-bromo-3-(2-fluorophenyl)-1,2-benzisoxazol-6-yl]oxy}acetic acid, mp 180°–182° C.

Analysis: Calculated for C$_{15}$H$_9$BrFNO$_4$: 49.20%C; 2.48%H; 3.83%N. Found: 49.19%C; 2.47%H; 3.88%N.

EXAMPLE 35 a. To a mixture of 4 g of 2-chlororesorcinol dimethyl ether and 3.7 g of 2,3-difluorobenzoyl chloride in 60 ml of 1,2-dichloroethane at 5° C., 3.06 g of $AlCl_3$ is added in portions. The mixture is allowed to warm to room temperature and then refluxed for 30 minutes. The reaction mixture is poured into concentrated HCl-ice and is permitted to stand about 72 hours. The aqueous layer is extracted with additional organic solvent, dried over $Na_2SO_4$ and evaporated to give 3-chloro-2-hydroxy-4-methoxy-2',3'-difluorobenzophenone, mp 161°–162° C.

Analysis: Calculated for $C_{14}H_9ClF_2O_3$: 56.30%C; 3.04%H; 12.72%F. Found: 56.26%C; 3.06%H; 12.56%F.

b. To a solution of 24 g of 3-chloro-2-hydroxy-4-methoxy-2',3'-difluorobenzophenone in 160 ml pyridine, 22 g of hydroxylamine HCl is added. The mixture is refluxed for 2 hours and the pyridine evaporated in vacuo. The residue is partitioned between ethyl acetate and 5% HCl. The ethyl acetate extract is washed with water, dried over $Na_2SO_4$ and evaporated to give a pale yellow solid which consists of two isomers. The solid is melted at 205° C. for approximately 13 minutes. The residue is dissolved in hot ethylacetate and then evaporated to dryness giving E-3-chloro-2',3'-difluoro-2-hydroxy-4-methoxybenzophenone oxime, mp 198°–199° C.

Analysis: Calculated for $C_{14}H_{10}ClF_2NO_3$: 53.60%C; 3.21%H; 4.47%N. Found: 53.95%C; 3.29%H; 4.42%N.

c. A mixture of 1.5 g of E-3-chloro-2',3'-difluoro-2-hydroxy-4-methoxybenzophenone oxime and 0.67 g of acetic anhydride are warmed at 60° C. for 30 minutes. The mixture is dissolved and then solidifies. The residue is partitioned between ethyl acetate and 10% $NaHCO_3$. The ethyl acetate extract is washed, dried over $Na_2SO_4$ and evaporated to give E-3-chloro-2',3'-difluoro-2-hydroxy-4-methoxybenzophenone O-acetyl oxime, mp 136°–139° C.

Analysis: Calculated for $C_{16}H_{12}ClF_2NO_4$: 54.02%C; 3.40%H; 3.94%N. Found: 53.89%C; 3.48%H; 3.97%N.

d. To a mixture of 1.4 g of NaH in 200 ml of DMF, a solution of 19 g of E-3-chloro-2',3'-difluoro-2-hydroxy-4-methoxybenzophenone O-acetyl oxime in 200 ml of DMF is added dropwise in an atmosphere of $N_2$. The mixture is stirred for one half hour and then warmed at 45° C. for one half hour. Water is added and a product precipitates and is filtered and dried giving 7-chloro-3-(2,3-difluorophenyl)-6-methoxy-1,2-benzisoxazole, mp 184°–189° C.

Analysis: Calculated for $C_{14}H_8ClF_2NO_2$: 56.87%C; 2.73%H; 4.47%N. Found: 56.95%C; 2.84%H; 4.77%N.

e. A solid mixture of 12.4 g of 7-chloro-3-(2,3-difluorophenyl)-6-methoxy-1,2-benzisoxazole and 50 g of pyridine HCl is heated to 200° C. for 45 minutes. The mixture is poured into vigorously stirred ice water and 7-chloro-6-hydroxy-3-(2,3-difluorophenyl)-1,2-benzisoxazole precipitates, mp 250°–254° C.

Analysis: Calculated for $C_{13}H_6ClF_2NO_2$: 55.43%C; 2.15%H; 4.97%N. Found: 55.60%C; 2.25%H; 4.91%N.

f. To a solution of 12 g of 7-chloro-6-hydroxy-3-(2,3-difluorophenyl)-1,2-benzisoxazole in 120 ml of DMF, 6.36 g of $K_2CO_3$ is added followed by 7.83 g of $BrCH_2CO_2C_2H_5$. The reaction is warmed at 60° C. for two hours and then allowed to stand for 18 hours. To the mixture 200 ml of water and 15 ml of 50% NaOH are added. The mixture is warmed at 90° C. for 90 minutes, poured into water and acidified. The product is extracted into ethylacetate which is dried over $Na_2SO_4$ and evaporated to give {[7-chloro-3-(2,3-difluorophenyl)-1,2-benzisoxazol-6-yl]oxy}acetic acid, mp 183°–187° C.

Analysis: Calculated for $C_{15}H_8ClF_2NO_4$: 53.04%C; 2.37%H; 4.12%N. Found: 53.20%C; 2.49%H; 3.88%N.

EXAMPLE 36 a. To a solution of 10 g (0.033 m) of 2'-fluoro-4-methoxy-2,3-dichlorobenzophenone of Example 1 a in 100 ml of pyridine, 3.17 g of hydroxylamine HCl is added. The mixture is refluxed for about 64 hours. The pyridine is evaporated and the residue partitioned between 5% HCl and ethylacetate. The ethylacetate extract is washed with water, dried over $Na_2SO_4$ and evaporated to give 2,3-chloro-4-methoxy-2'-fluorobenzophenone oxime mp 195°–197° C.

Analysis: Calculated for $C_{14}H_{10}Cl_2FNO_2$: 53.52%C; 3.21%H; 4.46%N. Found: 53.55%C; 3.10%H; 4.42%N.

b. To a solution of 8 g of 2,3-dichloro-4-methoxy-2'-fluorobenzophenone oxime in 50 ml of DMF, 0.67 g of NaH is added under a $N_2$ atmosphere. The mixture is stirred for one hour and water is added to precipitate 7-chloro-3-(2-fluorophenyl)-6-methoxy-1,2-benzisoxazole which is filtered and dried, mp 155°–158° C.

Analysis: Calculated for $C_{14}H_9ClFNO_2$: 60.55%C; 3.26%H; 5.05%N. Found: 60.63%C; 3.15%H; 5.01%N.

c. A solid mixture of 2 g of 7-chloro-3-(2-fluorophenyl)-6-methoxy-1,2-benzisoxazole and 20 g of pyridine hydrochloride is heated at 190°–210° C. for one hour. The hot reaction mixture is poured into vigorously stirred ice water. The mixture is made slightly acidic. 7-chloro-6-hydroxy-3-(2-fluorophenyl)-1,2-benzisoxazole is collected by filtration and dried, mp 140°–141° C.

Analysis: Calculated for $C_{13}H_7ClFNO_2$: 59.22%C; 2.68%H; 5.31%N. Found: 59.16%C; 2.65%H; 5.23%N.

d. The procedure of Example 35f may be employed with 7-chloro-6-hydroxy-3-(2-fluorophenyl)-1,2-benzisoxazole to yield {[7-chloro-3-(2-fluorophenyl)-1,2-benzisoxazol-6-yl]oxy}acetate, the product of Example 1d.

EXAMPLE 37 a. 2-chlororesorcinol dimethyl ether (22.0 g) and o-fluorobenzoyl chloride (20.2 g) are dissolved in 250 ml of dichloroethane, chilled in an ice bath and treated with $AlCl_3$ (18.6 g). Fifteen minutes after the addition is complete, the reaction is heated to reflux for 30 minutes. It is poured into $H_2O$ and extracted with ethylacetate. Evaporation and trituration with hexane gives 3-chloro-2'-fluoro-2-hydroxy-4-methoxybenzophenone, mp 132°–133° C.

Analysis: Calculated for $C_{14}H_{10}ClFO_3$: 59.90%C; 3.59%H; 12.63%Cl. Found: 59.77%C; 3.59%H; 12.51%Cl.

b. 3-chloro-2'-fluoro-2-hydroxy-4-methoxybenzophenone (24.6 g) is refluxed for 18 hours in 300 ml of pyridine containing 12.2 g of hydroxylamine hydrochloride. The reaction mixture is concentrated under reduced pressure and is distributed between ether and 5% HCl. The organic phase is dried and evaporated and the resulting crystalline product fused at 205° C. for 45 minutes. The product is cooled and recrystallized from toluene to give E-3-chloro-2'-fluoro-2-hydroxy-4-methoxybenzophenone oxime, mp 184°–186° C.

Analysis: Calculated for $C_{14}H_{11}ClFNO_3$: 56.86%C; 3.75%H; 4.79%N. Found: 56.67%C; 3.68%H; 4.66%N.

c. E-3-chloro-2'-fluoro-2-hydroxy4-methoxybenzophenone oxime (18.1 g) is warmed at 60° C. for 30 minutes with 9 ml of acetic anhydride. The reaction mixture is distributed between ether and 10% NaHCO$_3$ and washed with 10% NaHCO$_3$ until the washes remained basic. Drying, evaporation and trituration with hexane gives E-3-chloro-2'-fluoro-2-hydroxy-4-methoxybenzophenone O-acetyl oxime, mp 125°–128° C.

Analysis: Calculated for C$_{16}$H$_{13}$ClFNO$_4$: 56.90%C; 3.88%H; 4.15%N. Found: 59.79%C; 3.85%H; 4.20%N.

d. The procedure of Example 35d may be repeated to yield 7-chloro-3-(2-fluorophenyl)-6-methoxy-1,2-benzisoxazole. Thereafter the procedures of Example 36c and d may be employed to yield ethyl{[7-chloro-3-(2-fluorophenyl)-1,2-benzisoxazol-6-yl]oxy}acetate.

EXAMPLE 38 a. 5.0 g of 7-chloro-6-hydroxy-3-(2-fluorophenyl)-1,2-benzisoxazole of Example 36c in 30 ml of DMF is added dropwise with stirring to 1.1 g NaH in 30 ml DMF. After one hour, 2.6 ml of ethyl-2-bromoproprionate is added and the solution is stirred 1.5 hours. The solution is then poured onto ice and ethyl-2-{[7-chloro-3-(2-fluorophenyl)-1,2-benzisoxazole-6-yl]oxy}propionate precipitates which is filtered and dried, mp 79° C.

Analysis: Calculated for C$_{18}$H$_{15}$ClFNO$_4$: 59.50%C; 4.13%H; 3.85%N; 9.60%Cl. Found: 59.48%C; 4.09%H; 4.00%N; 9.58%Cl.

b. 6.8 g of ethyl-2-{[7-chloro-3-(2-fluorophenyl)-1,2-benzisoxazole-6-yl]oxy}propionate is dissolved in 35 ml of methanol and 25 ml of a 15% NaOH solution is added. The suspension is heated for two hours. The reaction mixture is poured onto ice, acidified with HCl and a solid precipitates which is filtered and dried in vacuo to give 2-{[7-chloro-3-(2-fluorophenyl)-1,2-benzisoxazole-3-yl]oxy}propionic acid, mp 159°–161° C.

Analysis: Calculated for C$_{16}$H$_{11}$ClFNO$_4$: 57.2%C; 3.28%H; 4.18%N; 10.55%Cl. Found: 56.8%C; 3.24%H; 4.17%N; 10.51%Cl.

EXAMPLE 39 a To a mixture of 21 g of 2,5-difluorobenzoyl chloride and 20.4 g of 2-chlororesorcinol dimethyl ether in 250 ml of 1,2-dichloroethane at 5°–10° C. 15.7 g of AlCl$_3$ is added in portions. The mixture is allowed to warm to room temperature and is then refluxed for 30 minutes. The mixture is poured into concentrated HCl and ice and stirred for approximately one hour. The product is extracted with ethyl acetate, dried over Na$_2$SO$_4$ and evaporated to give 3-chloro-2',5'-dilfluoro-2-hydroxy-4-methoxybenzophenone, mp 178°–180° C.

Analysis: Calculated for C$_{14}$H$_9$ClF$_2$O$_3$: 56.30%C; 3.04%H; 12.72%N. Found: 56.16%C; 3.01%H; 12.75%N.

b. A mixture of 28 g of 3-chloro-2',5'-difluoro-4-hydroxy-4-methoxybenzophenone and 26 g of hydroxylamine HCl in 250 ml pyridine is refluxed for three hours. Pyridine is evaporated and the residue partitioned between ethyl acetate and 5% HCl. The ethyl acetate extract is washed with water, dried over Na$_2$SO$_4$ and evaporated to give a solid product as a mixture of isomers. The solid is heated at 200°–210° C. for approximately 30–45 minutes and recrystallized from toluene giving E-3-chloro-2',5'-difluro-2-hydroxy-4-methoxybenzophenone oxime, mp 209°–210° C.

Analysis: Calculated for C$_{14}$H$_{10}$ClF$_2$NO$_3$: 53.60%C; 3.29%H; 4.47%N. Found: 53.61%C; 3.22%H; 4.43%N.

c. A mixture of 19 g of E-3-chloro-2',5'-difluoro-2-hydroxy-4-methoxybenzophenone oxime and 10 ml of acetic anhydride was warmed at 60° C. for 30 minutes. On cooling the mixture solidifies. The residue is partitioned between ethyl acetate and 10%NaHCO$_3$. The ethylacetate extract is washed with water, dried over Na$_2$SO$_4$ and evaporated to give E-3-chloro-2',5'-difluoro-2-hydroxy-4-methoxybenzophenone O-acetyl oxime, mp 130°–131° C.

Analysis: Calculated for C$_{16}$H$_{12}$ClF$_2$NO$_4$: 54.02%C; 3.40%H; 3.94%N. Found: 53.76%C; 3.37%H; 3.89%N.

d. To a suspension of NaH/200 ml of DMF in an atmosphere of N$_2$, 19.5 g of E-3-chloro-2',5'-difluoro-2-hydroxy-4-methoxybenzophenone O-acetyl oxime in 50 ml of DMF is added dropwise. The mixture is stirred 30 minutes and water is added to precipitate 7-chloro-3-(2,5-difluorophenyl)-6-methoxy-1,2-benzisoxazole, mp 198°–199° C.

Analysis: Calculated for C$_{14}$H$_8$ClF$_2$NO$_2$: 56.87%C; 2.73%H; 4.74%N. Found: 56.74%C; 2.70%H; 4.70%N.

e. A mixture of 10 g of 7-chloro-3-(2,5-difluorophenyl)-6-methoxy-1,2-benzisoxazole and 40 g of pyridine HCl is heated at 200° C. for 45 minutes. The hot mixture is poured into vigorously stirred ice water and a product precipitates out. The product is filtered and dried giving 7-chloro-3-(2,5-difluorophenyl)-6-hydroxy-1,2-benzisoxazole, mp 256°–257° C.

Analysis: Calculated for C$_{13}$H$_6$ClF$_2$NO$_2$: 55.43%C; 2.15%H; 4.97%N. Found: 55.26%C; 2.02%H; 4.93%N.

f. To a solution of 9.3 g of 7-chloro-3-(2,5-difluorophenyl)-6-hydroxy-1,2-benzisoxazole in 100 ml of DMF, 4.97 g of K$_2$CO$_3$ and 6.07 g of ethyl bromoacetate is added dropwise. The mixture is heated for two hours at 60° C. To the mixture 200 ml of water and 15 ml of 50% NaOH are added. The mixture is stirred at 90° C. for 90 minutes and then poured into water and acidified. The product is extracted with ethylacetate, dried over Na$_2$SO$_4$ and evaporated to give {[7-chloro-3-(2,5-difluorophenyl)-1,2-benzisoxazol-6-yl]oxy}acetic acid.

Analysis: Calculated for C$_{15}$H$_8$ClF$_2$NO$_4$: 53.04%C; 2.37%H; 4.12%N. Found: 53.37%C; 2.39%H; 4.01%N.

EXAMPLE 40 a. 2-chlororesorcinol dimethyl ether (3.4 g) is dissolved in 20 ml of CH$_2$Cl$_2$ and TiCl$_4$ (4.3 ml) is added. To this solution is added dichloromethyl methyl ether (2.3 g). After 30 minutes the reaction mixture is poured into H$_2$O into H$_2$O and extracted with ether. Drying and evaporation gives 3-chloro-2,4-dimethoxybenzaldehyde, mp 107°–108° C.

Analysis: Calculated for C$_9$H$_9$ClO$_3$: 53.88%C; 4.52%H; 17.68%Cl. Found: 53.93%C; 4.52%H; 17.42%Cl.

b. 3-chloro-2,4-dimethoxybenzaldehyde (2.75 g) is refluxed for 30 minutes in 20 ml of dichloroethane containing 1.8 g of AlCl$_3$. The reaction mixture is then poured into H$_2$O and extracted with CH$_2$Cl$_2$. Evaporation and recrystallization from isopropanol gives 3-chloro-2-hydroxy-4-methoxybenzaldehyde, mp 125° C.

Analysis: Calculated for C$_8$H$_7$ClO$_3$: 51.49%C; 3.78%H; 19.00%Cl. Found: 51.33%C; 3.78%H; 18.65%Cl.

c. 3-chloro-2-hydroxy-4-methoxybenzaldehyde (1.48 g) is suspended in 15 ml of H$_2$O and hydroxylamine-O-sulfonic acid (1.08 g) is added, along with 0.1 g of Na$_2$SO$_4$. After three hours an additional 15 ml of H$_2$O is added. After a total of four hours the reaction mixture is treated with 8% NaHCO₃ solution and then extracted into ether. Evaporation and trituration with hexane gives a solid product. Recrystallization from toluene/hexane gives 7-chloro-6-methoxy-1,2-benzisoxazole, mp 115°–118° C.

Analysis: Calculated for $C_8H_6ClNO_6$: 52.33%C; 3.29%H; 7.63%N. Found: 52.35%C; 3.30%H; 7.71%N.

d. The procedure of Example 35e and f may be employed with 7-chloro-6-methoxy-1,2-benzisoxazole to yield {[7-chloro-1,2-benzisoxazol-6-yl]oxy}acetic acid.

EXAMPLE 41 a. To a solution of 1.7 g of 2-chlororesorcinol dimethyl ether and 2.08 g of o-trifluoromethyl benzoyl chloride in 50 ml of 1,2-dichloroethane at 5°–7° C., 1.6 g of ferric chloride is added gradually. The mixture is brought to room temperature and allowed to stand 18 hours. The reaction mixture is refluxed 30 minutes and poured into 5% HCl and ice. The aqueous phase is extracted with additional organic solvent. The combined organic extracts are washed with water, dried over Na₂SO₄ and evaporated to give 3-chloro-2-hydroxy-4-methoxy-2'-trifluoromethylbenzophenone, mp 101°–102° C.

Analysis: Calculated for $C_{15}H_{10}ClF_3O_3$: 54.48%C; 3.05%H; 17.24%F. Found: 54.16%C; 2.91%H; 17.16%F.

b. The procedures described in the foregoing examples (such as Example 35) may be employed with 3-chloro-2-hydroxy-4-methoxy-2'-trifluoromethylbenzophenone to obtain the corresponding oxime, cyclizing the oxime and forming the acid to yield {[7-chloro-3-(2-trifluoromethylphenyl)-1,2-benzisoxazol-6-yl]oxy}acetic acid.

EXAMPLE 42 a. 10 g of 7-chloro-3-(2-fluorophenyl)-6-methoxy-1,2-benzisoxazole of Example 36b is dissolved in glacial acetic acid (800 ml) with stirring and chlorine gas is bubbled through at a slow rate for one half hour to give a solution containing a small amount of suspended starting material. The reaction mixture is stirred for 18 hours at room temperature and then the reaction mixture is poured onto ice water with stirring to precipitate 5,7-dichloro-3-(2-fluorophenyl)-6-methoxy-1,2-benzisoxazole, mp 121° C.

Analysis: Calculated for $C_{14}H_8Cl_2FNO_2$: 53.87%C; 2.59%H; 4.49%N. Found: 53.54%C; 2.59%H; 4.51%N.

b. 10 g of 5,7-dichloro-3-(2-fluorophenyl)-6-methoxy-1,2-benzisoxazole is combined with 100 g pyridine hydrochloride and heated at 200° C. for 0.5 hours. The hot melt is quickly poured into stirred ice water and a resultant precipitate is filtered and dried for 48 hours in vacuo (64° C.). The solid is recrystallized from toluene affording 5,7-dichloro-3-(2-fluorophenyl)-6-hydroxy-1,2-benzisoxazole, mp 194°–196° C.

Analysis: Calculated for $C_{13}H_6Cl_2FNO_2$: 52.44%C; 2.01%H; 4.70%N; 23.53%Cl. Found: 52.07%C; 2.08%H; 4.96%N; 23.92%Cl.

c. 1.4 g NaH is suspended in 50 ml DMF with stirring. A solution of 7.2 g of 5,7-dichloro-3-(2-fluorophenyl)-6-hydroxy-1,2-benzisoxazole in 50 ml DMF is added dropwise. The solution is heated to 45° C. for one hour. Ethyl bromoacetate (4.0 g) in 20 ml DMF is added dropwise and the reaction is stirred at 40° C. for two hours. The solution is poured into 1 l of water, stirred and extracted with ethyl acetate. The organic extracts are washed with saturated NaCl solution and the solvent removed in vacuo affording ethyl{[5,7-chloro-3-(2-fluorophenyl)-1,2-benzisoxazole-6yl]oxy}acetate, mp 105°–106° C.

Analysis: Calculated for $C_{17}H_{12}Cl_2FNO_2$: 53.26%C; 3.13%H; 3.65%N; 18.39%Cl. Found: 52.91%C; 3.00%H; 3.41%N; 18.09%Cl.

d. 14.0 g of ethyl{[5,7-dichloro-3-(2-fluorophenyl)-1,2-benzisoxazole-6-yl]oxy}acetate is heated in 75% ethanol/H₂O (700 ml) with stirring until a solution results. 20 ml of a 50% solution of NaOH is added and a precipitate forms. With additional heating and stirring the precipitate goes into solution and is allowed to stir for 2.5 hours. The ethanol is then evaporated in vacuo and the residue is made acidic with 10% HCl. The precipitated solid is filtered and dried in vacuo to afford {[5,7-dichloro-3-(2-fluorophenyl)-1,2-benzisoxazole-6-yl]oxy}acetic acid, mp 160°–170° C.

Analysis: Calculated for $C_{15}H_8Cl_2FNO_4$: 50.59%C; 2.26%H; 3.93%N. Found: 50.53%C; 2.32%H; 3.88%N.

EXAMPLE 43 a. To a suspension of NaH (1.0 g) of a 50% dispersion in mineral oil 50 ml DMF is added a solution of 5.0 g of 7-chloro-3-(2-fluorophenyl)-6-hydroxy-1,2-benzisoxazole of Example 36c in 50 ml DMF. The solution is stirred one hour at room temperature, then cooled to 5° C. and 3.5 g of N,N-dimethylthiocarbamoyl chloride is added all at once. The reaction is brought gradually to 60° C. and stirred for 2.5 hours. The solution is then poured into water and extracted with methylene chloride until the extracts are colorless. The combined organic extracts are washed with 10% K₂CO₃, then with saturated NaCl. The solvent is removed in vacuo yielding 7-chloro-6-(O-N,N-dimethylthiocarbamyl)-3-(2-fluorophenyl)-1,2-benzisoxazole, mp 153°–154° C.

Analysis: Calculated for $C_{16}H_{12}ClFN_2O_2S$: 54.8%C; 3.4%H; 7.9%N; 9.1%S. Found: 54.4%C; 3.4%H; 7.9%N; 9.1%S.

b. 4.5 g of 7-chloro-6-(O-N,N-dimethylthiocarbamyl)-3-(2-fluorophenyl)-1,2-benzisoxazole is heated under nitrogen at 205° C. for 45 minutes. A resultant cooled solid is recrystallized from ethyl acetate affording colorless prisms of 7-chloro-6-(S-N,N-dimethylthiocarbamyl)-3-(2-fluorophenyl)-1,2-benzisoxazole, mp 140°–142° C.

Analysis: Calculated for $C_{16}H_{12}ClFN_2O_2S$: 54.77%C; 3.44%H; 7.98%N; 9.14%S. Found: 54.87%C; 3.56%H; 7.86%N; 9.28%S.

c. 2.0 g of 7-chloro-6-(S-N,N-dimethylthiocarbamyl)-3-(2-fluorophenyl)-1,2-benzisoxazole is dissolved in methanol and 25 ml of 15% aqueous NaOH is added. The solution is refluxed for three hours. The reaction mixture is poured into a large quantity of water, acidified with HCl to precipitate 7-chloro-3-(2-fluorophenyl)-6-mercapto-1,2-benzisoxazole, mp 125°–129° C.

Analysis: Calculated for $C_{13}H_7ClFNOS$: 55.81%C; 2.50%H; 5.01%N; 11.46%S. Found: 55.94%C; 2.58%H; 5.09%N; 11.52%S.

d. 3.2 g of 7-chloro-3-(2-fluorophenyl)-6-mercapto-1,2-benzisoxazole, 3.1 g K₂CO₃ and 3.67 g of ethyl bromoacetate are added to 60 ml DMF and warmed for two hours at 50° C. with stirring. The solution is poured into 700 ml H₂O and extracted with ethyl acetate. The combined organic extracts are dried over K₂CO₃, and the solvent is removed in vacuo to afford ethyl{[7-chloro-3-(2-fluorophenyl)-1,2-benzisoxazole-6-yl]thio}acetate.

Analysis: Calculated for $C_{17}H_{13}ClFNO_3S$: 55.89%C; 3.56%H; 3.83%N; 8.76%S. Found: 55.92%C; 3.70%H; 3.80%N; 8.91%S.

e. 1.7 g of ethyl{[7-chloro-3-(2-fluorophenyl)-1,2-benzisoxazole-6-yl]thio}acetate is dissolved in 50 ml of ethanol with stirring and warming. A 50% solution of NaOH is added (3 ml) with 25 ml water and a precipitate of a solid is obtained. After one hour, the ethanol is removed and the residue is made acidic with HCl. The precipitate is filtered and dried affording {[5,7-dichloro-3-(2-fluorophenyl)-1,2-benzisoxazole-6-yl]thio}acetic acid, mp 165° C.

Analysis: Calculated for $C_{15}H_9ClFNO_3S$: 53.41%C; 2.67%H; 4.15%N; 9.49%S. Found 53.39%C; 2.68%H; 4.19%N; 9.44%S.

EXAMPLE 44 a. To a solution of o-fluorobenzoyl chloride (47.6 g) in 100 ml dichloromethane is added $AlCl_3$ (40.0 g) portionwise, in about thirty minutes. To this resultant dark solution is added dropwise a solution of 1-chloro-3,5-dimethoxybenzene (52.0 g) in 120 ml dichloromethane, in fifteen minutes. After stirring at ambient temperature for four hours, the mixture is poured into one liter iced-dilute HCl solution and then stirred for 30 minutes. The organic layer is collected, evaporated to an oil, which is dissolved into ether, washed with water, dilute NaOH solution, water, then dried (saturated NaCl, anhydrous $MgSO_4$). After filtering, the solvent is evaporated to a solid, which is purified by silica gel, eluted with dichloromethane to yield 2-chloro-4,6-dimethoxy-2'-fluorobenzophenone, mp 88°–92° C.

Analysis: Calculated for $C_{15}H_{12}ClFO_3$: 61.13%C; 4.11%H; 12.03%Cl; 6.45%F. Found: 60.95%C; 4.06%H; 11.85%Cl; 6.38%F.

b. To a solution of 2-chloro-4,6-dimethoxy-2'-fluorobenzophenone (33 g) in 150 ml dichloroethane is added, portionwise in fifteen minutes, $AlCl_3$ (15 g). After stirring at reflux (90° C.) for three hours, the mixture is cooled, poured into one liter ice-dilute HCl solution, stirred for 30 minutes then extracted into ether. The ether/dichloroethane solution is washed with water, then dried (saturated NaCl, anhydrous $MgSO_4$) and filtered.

After filtering, the solvents are evaporated to yield 2-chloro-2'-fluoro-6-hydroxy-4-methoxybenzophenone, mp 85°–90° C.

Analysis: Calculated for $C_{14}H_{10}ClFO_3$: 59.90%C; 3.59%H; 6.77%F. Found: 59.78%C; 3.53%H; 7.00%F.

c. To 125 ml pyridine is added 2-chloro-2'-fluoro-6-hydroxy-4-methoxybenzophenone (28.5 g) and hydroxylamine hydrochloride (14 g). After stirring at reflux (120° C.) for three hours, the mixture is cooled, the pyridine evaporated to a yellow semi-solid. The solid is dissolved in ether, washed with water, then dried (saturated NaCl, anhydrous $MgSO_4$). After filtering, the solvent is evaporated to an oil, which solidifies to Z-2-chloro-2'-fluoro-6-hydroxy-4-methoxybenzophenone oxime, mp 130°–140° C., upon trituration with petroluem ether.

Analysis: Calculated for $C_{14}H_{11}ClFNO_3$: 56.86%C; 3.75%H; 4.74%N. Found: 56.74%C; 3.70%H; 4.74%N.

d. The Z-2-chloro-2'-fluoro-6-hydroxy-4-methoxybenzophenone oxime may be reacted with acetic anhydride as described in Example 30c to form E-2-chloro-2'-fluoro-6-hydroxy-4-methoxybenzophenone O-acetyl oxime.

e. To a suspension of NaH (2.4 g) in 20 ml DMF, is added a solution of E-2-chloro-2'-fluoro-6-hydroxy-4-methoxybenzophenone O-acetyl oxime (15 g) in 50 ml DMF. After stirring at ambient temperature for two hours, the mixture is poured into one l ice-water, stirred for 30 minutes and a precipitate is collected. The precipitate is washed with water then dried to yield 4-chloro-3-(2-fluorophenyl)-6-methoxy-1,2-benzisoxazole, mp 113°–115° C.

Analysis: Calculated for $C_{14}H_{19}ClFNO_2$: 60.55%C; 3.27%H; 5.05%N. Found: 60.52%C; 3.33%H; 4.96%N.

f. Using 4-chloro-3-(2-fluorophenyl)-6-methoxy-1,2-benzisoxazole with the procedures described in the foregoing examples, such as Example 20d and e, {4-chloro-3-(2-fluorophenyl)-1,2-benzisoxazol-6-yl]oxy}acetic acid, mp 172°–174° C. is obtained.

EXAMPLE 45 a. To a mixture of 3.9 g of $AlCl_3$ and 4.67 g of 2,3-dichloroanisole in 70 ml of 1,2-dichloroethane at −10° C., 5 g of o-methoxybenzoyl chloride is added dropwise. The mixture is stirred for 2.5 hours and is gradually warmed to 5° C. The reaction mixture is poured into concentrated HCl and ice. The mixture is stirred one half hour to decompose the complex. The aqueous layer is extracted with additional organic solvent. The combined organic layers are washed until neutral, dried over $Na_2SO_4$ and evaporated to give an oil which solidifies on trituration with hexane. The crude product is recrystallized from 95% ethanol giving 2,3-dichloro-2',4-dimethoxybenzophenone, mp 94°–96° C.

Analysis: Calculated for $C_{15}H_{12}Cl_2O_3$: 58.00%C; 3.89%H; Found: 57.84%C; 3.81%H;

b. A solid mixture of 13 g of 2,3-dichloro-2',4-dimethoxybenzophenone and 52 g of pyridine HCl is heated at 200° C. for one hour. The hot mixture is then poured into vigorously stirred ice water. The product is extracted with ethyl acetate. The extract is dried over $Na_2SO_4$ and evaporated to give 2,3-dichloro-2',4-dihydroxybenzophenone, mp 197°–201° C.

Analysis: Calculated for $C_{13}H_3Cl_2O_3$: 55.15%C; 2.80%H. Found: 55.26%C; 2.86%H.

c. To a suspension of 2.87 g of NaH in 150 ml DMF, 30.76 g of 2,3-dichloro-2',4-dihydroxybenzophenone in 100 ml of DMF is added followed by the addition of 18.37 g of ethyl bromoacetate. The mixture is stirred approximately one and one half hours, poured into ice and acid and extracted with $CHCl_3$. The $CHCl_3$ extract is dried over $Na_2SO_4$ and evaporated to give ethyl 2,3-dichloro-4-(2-hydroxybenzoyl)phenoxy acetate, mp 109°–110° C.

Analysis: Calculated for $C_{17}H_{14}Cl_2O_5$: 55.30%C; 3.82%H. Found: 55.15%C; 3.81%H.

d. Employing ethyl 2,3-dichloro-4-(2-hydroxybenzoyl)phenoxy acetate and the procedures of the foregoing examples, the corresponding oxime may be formed and cyclized and the ester hydrolyzed to yield [7-chloro-3-2-hydroxyphenyl)-1,2-benzisoxazol-6-yl]oxy acetic acid.

EXAMPLE 46 a. To a stirring solution of phenacetyl chloride (25 g) in 150 ml carbon disulfide, is added $AlCl_3$ (22 g) portionwise over a period of thirty minutes, followed by a solution of 2,3-dichloroanisole (28 g) in 50 ml carbon disulfide.

After stirring at reflux (50° C.) for three hours, the mixture is cooled, then $AlCl_3$ (22 g) is added and the mixture is stirred at reflux for two hours. The mixture is cooled, poured into a solution of cold 15% HCl, stirred for 30 minutes then extracted with ethyl acetate/ethyl ether. The organic extract is washed with water then dried (saturated NaCl, anhydrous $MgSO_4$).

After filtering, the solvents are evaporated to give 2,3-dichloro-4-phenacetylphenol, mp 173°–180° C.

Analysis: Calculated for $C_{14}H_{10}Cl_2O_2$: 59.81%C; 3.59%H. Found: 60.15%C; 3.65%H.

b. 2,3-dichloro-4-phenacetylphenol is reacted with hydoxylamine hydrochloride in pyridine as generally described in the foregoing examples to yield 2,3-dichloro-4-phenacetylphenol oxime.

c. To a suspension of NaH (2.54 g) in 10 ml of dry DMF is added a solution of 2,3-dichloro-4-phenacetylphenol oxime (6.3 g) in 25 ml dry DMF.

After stirring at 80° C. for two hours, the mixture is cooled, then a solution of ethyl bromoacetate (4.2 g) in 10 ml dry DMF is added and stirred at ambient temperature for 30 minutes and then at 60° C. for 30 minutes.

After cooling, the mixture is poured into 500 ml of water, stirred for 30 minutes, then extracted with ethylacetate. The organic layer is washed with water then dried (saturated NaCl, anhydrous $MgSO_4$). After filtering, the solvent is evaporated to an oil from which ethyl {[3-benzyl-7-chloro-1,2-benzisoxazol-6-yl]oxy}acetate was obtained, mp 120°–122° C.

Analysis: Calculated for $C_{18}H_{16}ClNO_4$: 62.52%C; 4.66%H; 4.05%N. Found: 62.35%C; 4.74%H; 3.83%N.

d. To 650 ml absolute ethanol is added ethyl{(3-benzyl-7-chloro-1,2-benzisoxazol-6-yl)oxy}acetate (25.0 g), followed by 50% NaOH solution (30 ml). After stirring at reflux (80° C.) for one hour, 500 ml of water is added, the pH adjusted to 1 with concentrated HCl, then further diluted with 1 liter water. The resultant precipitate is collected, washed with water, then dissolved in dichloromethane. The dichloromethane solution is washed with water, then dried (saturated NaCl, anhydrous $MgSO_4$).

After filtering, the solvent is evaporated to {(3-benzyl-7-chloro-1,2-benzisoxazol-6-yl)oxy}acetic acid, mp 147°–153° C.

Analysis: Calculated for $C_{16}H_{12}ClNO_4$: 60.48%C; 3.81%H; 4.41%N; 11.16%Cl. Found: 60.36%C; 3.96%H; 4.33%N; 10.91%Cl.

EXAMPLE 47 a. The Friedel-Crafts procedure of Example 46 is repeated with 2,3-dichloroanisole, 1-naphthyl chloride and $AlCl_3$ to yield (2,3-dichloro-4-hydroxyphenyl)(1-naphthyl)methanone.

b. To a solution of 22.48 g of (2,3-dichloro-4-hydroxyphenyl)(1-naphthyl)methanone in 150 ml of pyridine, 9.87 g of hydroxylamine-hydrochloride are added. The mixture is refluxed for about 64 hours. Additional hydroxylamine-HCl (9.87 g) is added and reaction mixture refluxed for 18 hours. The pyridine is evaporated in vacuo and the residue is partitioned between 5% HCl and ethyl acetate. The ethyl acetate extract is washed with water, dried over $Na_2SO_4$ and evaporated to give a semi-solid product. This product is dissolved in approximately 100 ml of ethyl acetate and passed through a column of charcoal. The filtrate is evaporated to give a solid which upon trituration with hexane-ether yielded(2,3-dichloro-4-hydroxyphenyl)(1-naphthyl)methanone oxime, mp 145°–160° C.

Analysis: Calculated for $C_{17}H_{11}Cl_2NO_2$: 61.46%C; 3.34%H; 4.22%N. Found: 61.53%C; 3.45%H; 4.14%N.

c. To a solution of 3 g of (2,3-dichloro-4-hydroxyphenyl)(1-naphthyl)methanone oxime in 25 ml of DMF, 0.54 g of NaH is added under $N_2$. The mixture is heated to an internal temperature of 100° C. for one hour and 20 minutes. The reaction mixture is cooled to room temperature and 1.65 g of ethyl bromoacetate is added dropwise. The mixture is stirred for 18 hours, water is added and the product is extracted with ethyl acetate. The ethyl acetate extract is washed with water, dried over $Na_2SO_4$ and evaporated to give ethyl{[7-chloro-3-(1-napthyl)-1,2-benzisoxazol-6-yl]oxy}acetate, mp 75°–85° C.

Analysis: Calculated for $C_{21}H_{16}ClNO_4$: 66.06%C; 4.22%H; 3.67%N. Found: 65.81%C; 4.24%H; 3.53%N.

d. A suspension of 1.85 g of ethyl-{[7-chloro-3-(1-naphthyl)-1,2-benzisoxazol-6-yl]oxy}acetate, 100 ml of ethanol and 2 ml of 50% NaOH is refluxed for one hour. To the hot mixture, 100 ml of water is added followed by enough concentrated HCl to make the mixture acidic. The reaction mixture is stirred and a precipitate forms on cooling. Ethanol is evaporated in vacuo and {[7-chloro-3-(1-naphthyl)-1,2-benzisoxazol-6-yl]oxy}acetic acid is filtered off and dried in vacuum, mp 172°–174° C.

Analysis: Calculated for $C_{19}H_{12}ClNO_4$: 64.50%C; 3.42%H; 3.96%N. Found: 64.51%C; 3.38%H; 3.97%N.

EXAMPLE 48 a. The Friedel-Crafts reaction described in the foregoing examples is repeated with 2,3-dichloroanisole, 3--fluorobenzoyl chloride and $AlCl_3$ to yield 2,3-dichloro-4-hydroxy-3'-fluorobenzophenone.

b. To a solution of 5 g of 2,3-dichloro-4-hydroxy-3'-fluorobenzophenone in 50 ml of pyridine, 1.58 g of hydroxylamine hydrochloride is added. The mixture is refluxed for 18 hours. The pyridine is evaporated in vacuo and the residue is partitioned between 5% HCl and ethylacetate. The ethylacetate is washed with water, dried over $Na_2SO_4$ and evaporated to give 2,3-dichloro-4-hydroxy-3'-fluorobenzophenone oxime as a mixture of isomers, mp 178°–185° C.

Analysis: Calculated for $C_{14}H_{10}Cl_2FNO_2$: 53.52%C; 3.21%H; 4.46%N. Found: 53.66%C; 3.14%H; 4.39%N.

c. To a solution of 3 g of 2,3-dichloro-4-hydroxy-3'-fluorobenzophenone oxime in 20 ml of DMF, 0.25 g of NaH is added in an atmosphere of $N_2$. The mixture is stirred for 18 hours. The mixture is heated to 100° C. for one hour. The reaction mixture is poured into ice water to yield 7-chloro-3-(3-fluorophenyl)-6-methoxy-1,2-benzisoxazole, mp 149°–150° C.

Analysis: Calculated for $C_{14}H_9ClFNO_2$: 60.55%C; 3.26%H; 5.05%N. Found: 60.54%C; 3.00%H; 4.91%N.

d. A solid mixture of 14.47 g of 7-chloro-3-(3-fluorophenyl)-6-methoxy-1,2-benzisoxazole and 58 g of pyridine hydrochloride is heated at 190°–200° C. for one hour. The hot mixture is poured into vigorously stirred ice water and 7-chloro-6-hydroxy-3-(3-fluorophenyl)-1,2-benzisoxazole is collected by filtration and washed well with $H_2O$, mp 215°–217° C.

Analysis: Calculated for $C_{13}H_7ClFNO_2$: 59.22%C; 2.68%H; 5.31%N. Found: 59.15%C; 2.66%H; 5.16%N.

e. A solution of 10.2 g of 7-chloro-6-hydroxy-3-(3-fluorophenyl)-1,2-benzisoxazole is added to a mixture of 1.3 g of NaH in 25 ml of DMF. A solution of 6.68 g of ethyl bromoacetate in 25 ml of DMF is added and the mixture is stirred for two and one half hours. 10 ml of 50% NaOH, 175 ml of $H_2O$ and 30 ml of DMF are added to the reaction mixture which is then heated at 80°–85° C. for one hour. The mixture is made acidic with concentrated HCl, water is added and {[7-chloro-3-(3-fluorophenyl)-1,2-benzisoxazol-6-yl]oxy}acetic acid is collected by filtration, mp 205°–209° C.

Analysis: Calculated for $C_{15}H_9ClFNO_4$: 56.00%C; 2.83%H; 4.36%N. Found: 55.96%C; 2.81%H; 4.21%N.

EXAMPLE 49 a. To a solution of 1.0 g of 4-chloro-3-(o-fluorophenyl)-6-methoxy-1,2-benzisoxazole, of Example 44 e, in 50 ml glacial acetic acid is added chlorine gas (the solution is purged for five minutes). After stirring at ambient temperature for one hour, the mixture is poured into 500 ml water, stirred for fifteen minutes and a resultant precipitate is extracted into ether/ethyl acetate. The organic layer is washed with water, then dried (saturated NaCl, anhydrous $MgSO_4$) and after filtering the solvents are evaporated to yield 3-(o-fluorophenyl)-6-methoxy-4,5,7-trichloro-1,2-benzisoxazole, mp 120°–140° C.

Analysis: Calculated for $C_{14}H_7Cl_3FNO_2$: 48.51%C; 2.04%H. Found: 48.15%C; 2.27%H.

b. The procedures of Examples 20d and e may be employed with 3-(o-fluorophenyl)-6-methoxy-4,5,7-trichloro-1,2-benzisoxazole to yield {[4,5,7-trichloro-3-(2-fluorophenyl)-1,2-benzisoxazol-6-yl]oxy}acetic acid.

EXAMPLE 50

10 g of 7-chloro-6-hydroxy-3-(2-fluorophenyl)-1,2-benzisoxazole of Example 36 c is dissolved in 70 ml DMF and 7.86 g $K_2CO_3$ is added with stirring. 3.6 ml of chloroacetonitrile is added and the mixture is stirred 0.5 hours at room temperature, then raised to 55° C. for 2 hours. Stirring is continued 15 hours at room temperature and 1.5 ml of chloroacetonitrile is added and the reaction stirred 6 hours at 50° C. It is poured into a large volume of ice/$H_2O$ and {[7-chloro-3-(2-fluorophenyl)-1,2-benzisoxazole-6-yl]oxy}acetonitrile which is precipitated is collected by filtration, mp 147° C.

Analysis: Calculated for $C_{15}H_8ClFN_2O_2$: 59.51%C; 2.66%H; 9.25%N. Found: 59.38%C; 2.67%H; 9.36%N.

EXAMPLE 51

15 g 7-chloro-6-hydroxy-3-(2-fluorophenyl)-1,2-benzisoxazole in 75 ml DMF is added to a suspension of 3.0 g NaH in 75 ml DMF. After one hour at room temperature, 16.7 ml of ethyl-2-bromoisobutyrate is added. After 72 hours at 50° C. the reaction mixture is poured into ice/HCl and extracted with $CH_2Cl_2$ and the organic phase is washed with 5% $K_2CO_3$, followed by washing with saturated NaCl. It is dried over $MgSO_4$, filtered and is evaporated to a brown oil. The oil is distilled at reduced pressure to remove unreacted ethyl-2-bromoisobutyrate and the residue is triturated with ether/petroleum ether, filtered and the mother liquor is evaporated to an oil which is distilled (200° C., 0.1 mm) affording ethyl-2-{[7-chloro-3-(2-fluorophenyl)-1,2-benzisoxazole-6-yl]oxy}-2-methyl propionate.

Analysis: Calculated for $C_{19}H_{17}ClFNO_4$: 60.6%C; 4.53%H; 3.70%N. Found: 60.0%C; 4.72%H; 3.60%N.

EXAMPLE 52 a. To a mixture of 46 g of 4-chloro-2-fluorobenzoyl chloride and 38.9 g of 2,3-dichloroanisole in 150 ml of 1,2-dichloroethane, 32 g of $AlCl_3$ is added gradually. The mixture is warmed to 40° C. with a vigorous evolution of gas. The mixture is poured into concentrated HCl and ice. The organic layer is separated and the aqueous layer is extracted with additional organic solvent. The combined organic extracts are washed with water, dried over $Na_2SO_4$ and evaporated. The crude product is triturated with hexane to give 2,3-dichloro-4-methoxy-4'-chloro-2'-fluorobenzophenone. An analytical sample is recrystallized from EtOH, mp 115°–116° C.

Analysis: Calculated for $C_{14}H_8Cl_3FO_2$: 50.41%C; 2.42%H; 5.80%F. Found: 50.11%C; 2.36%H; 6.17%F.

b. In a manner similar to that of Example 21 b, 2,3-dichloro-4-methoxy-4'-chloro-2'-fluorobenzophenone is converted into 2,3-dichloro-4-methoxy-4'-chloro-2'-fluorobenzophenone oxime.

c. To a mixture of 2.24 g of NaH in 100 ml DMF, 21.75 g of 2,3-dichloro-4-methoxy-4'-chloro-2'-fluorobenzophenone oxime in 100 ml of DMF is added dropwise. After addition the mixture is stirred one hour and the reaction mixture poured into ice water. A product which precipitates is filtered and dried giving a mixture of isomers which is chromatographed on silica gel with 50% hexane and 50% toluene as eluant to yield 7-chloro-3-(4-chloro-2-fluorophenyl)-6-methoxy-1,2-benzisoxazole, mp 193°–194° C.

Analysis: Calculated for $C_{14}H_8Cl_2FNO_2$: 53.87%C; 2.58%H; 4.49%N. Found: 54.01% C; 2.56%H; 4.44%N.

d. A solid mixture of 5.4 g of 7-chloro-3-(4-chloro-2-fluorophenyl)-6-methoxy-1,2-benzisoxazole and 22.4 g of pyridine HCl is heated at 200° C. for two hours. The reaction mixture is then poured into vigorously stirring ice water and a demethylated product is obtained.

To a solution of 3.9 g of the demethylated product in 40 ml of DMF, 1.9 g of $K_2CO_3$ and 2.3 g of ethyl bromo acetate are added. The reaction is warmed to 60° C. for two hours and permitted to stand 18 hours. To the reaction mixture 100 ml of water and 10 ml of 50% NaOH are added. The mixture is heated at 90° C. for 90 minutes and the reaction mixture is poured into water, acidified and extracted with ethyl acetate, dried and evaporated to yield {[7-chloro-3-(4-chloro-2-fluorophenyl)-1,2-benzisoxazol-6-yl]oxy}acetic acid, mp 226°–227° C.

Analysis: Calculated for $C_{15}H_8Cl_2FNO_4$: 50.59%C; 2.26%H; 3.93%N. Found: 50.39%C; 2.24%H; 4.06%N.

EXAMPLE 53

To a suspension of 0.9 g lithium aluminum hydride (98%) in 100 ml anhydrous ether is added a solution of 10 g ethyl-2-{[7-chloro-3-(2-fluorophenyl)-1,2-benzisoxazole-6-yl]oxy}acetate of Example 1 d in 200 ml ether containing sufficient tetrahydrofuran to effect solution. The reaction mixture is stirred for two hours at room temperature and one hour at reflux. To the reaction mixture is added 0.9 ml $H_2O$, 0.9 ml 15% NaOH and 2.7 ml $H_2O$. The stirred suspension is filtered and the filtrate is concentrated to afford 2-{[7-chloro-3-(2-fluorophenyl)-1,2-benzisoxazole-6-yl]oxy}ethanol, mp 112° C.

Analysis: Calculated for $C_{15}H_{11}ClFNO_3$: 58.63%C; 3.58%H; 4.56%N. Found: 58.48%C; 3.62%H; 4.49%N.

EXAMPLE 54

4.5 g of ethyl-2-{[7-chloro-3-(2-fluorophenyl)-1,2-benzisoxazole-6-yl]oxy}-2-methylpropionate, of Example 51, is dissolved in 35 ml methanol and 30 ml of a 15% NaOH solution is added thereto. The suspension is heated at reflux for 4 hours and then poured into ice-water, and acidified, producing an oily precipitate. This precipitate is extracted with ether and the ether extracts are washed with 10% NaHCO$_3$. The basic extracts are acidified with concentrated HCl and chilling thereof affords 2-{[7-chloro-3-(2-fluorophenyl)-1,2-benzisoxazole-6-yl]oxy}-2-methyl propionic acid, mp 108° C.

Analysis: Calculated for C$_{17}$H$_{13}$ClFNO$_4$: 58.45%C; 3.72%H; 4.01%N. Found: 58.39%C; 3.75%H; 3.96%N.

EXAMPLE 55

3.35 g NaN$_3$ and 2.25 g of AlCl$_3$ are stirred in 50 ml THF at reflux for 0.5 hour. A solution of 5 g {[7-chloro-3-(2-fluorophenyl)-1,2-benzisoxazole-6-yl]oxy}acetonitrile, of Example 50, in 50 ml THF is added and the reaction mixture is stirred at reflux for about 120 hours. To the reaction mixture is added water and the solvent is removed. The residue is treated with dilute HCl and extracted with CHCl$_3$. Upon attempted extraction of the chloroform solution with 15% NaOH a precipitate forms which is filtered, dissolved in hot water and acidified to afford 7-chloro-3-(2-fluorophenyl)-6- {[5-tetrazolylmethyl]oxy}-1,2-benzisoxazole, mp 198°-200° C.

Analysis: Calculated for C$_{15}$H$_9$ClFN$_5$O$_2$: 52.17%C; 2.60%H; 20.28%N. Found: 52.02%C; 2.69%H; 20.37%N.

EXAMPLE 56

To a solution of 10.0 g of {[7-chloro-3-(2-fluorophenyl)-1,2-benzisoxazol-6-yl]oxy}acetic acid in 70 ml of ice-cold sulfuric acid, 2.5 ml of 16N nitric acid is added. The reaction mixture is stirred for 2 hr in the cold and then allowed to warm to room temperature over 1 hr. The reaction mixture is then poured onto ice and the solid is collected. The filter cake is washed with water until the washes are no longer acidic and then recrystallized from acetic acid to afford {[7-Chloro-3-(2-fluoro-5-nitrophenyl)-1,2-benzisoxazol-6-yl]oxy}acetic acid, mp 238°-240° C.

Analysis: Calculated for C$_{15}$H$_8$ClFN$_2$O$_6$: 49.13%C; 2.05%H; 7.60%N. Found: 48.72%C; 2.00%H; 7.57%N.

EXAMPLE 57

To a solution of 10.9 g of {[7-chloro-3-(2-fluorophenyl)-1,2-benzisoxazol-6-yl]oxy}acetic acid in 70 ml of ice-cold sulfuric acid, 2.2 ml of 16N nitric acid is added. The reaction mixture is stirred in the cold for 2 hr, allowed to warm to room temperature over 1 hr and poured into ice-water. The precipitate is collected to afford {[7-chloro-3-(2-fluoro-5-nitrophenyl)-1,2-benzisoxazol-6-yl]oxy}acetic acid. The fluoro-compound is treated with excess sodium methoxide in refluxing methanol for a total of 48 hr. The reaction mixture is acidified and the product is collected by filtration. Recrystallization from acetonitrile affords {[7-Chloro-3-(2-methoxy-5-nitrophenyl)-1,2-benzisoxazol-6-yl]oxy}acetic acid, mp 260°-262° C. (dec.)

Analysis: Calculated for C$_{16}$H$_{11}$ClN$_2$O$_7$: 50.74%C; 2.93%H; 7.40%N. Found: 50.27%C; 2.87%H; 7.43%N.

EXAMPLE 58

A solution of 5.0 g of 7-chloro-6-hydroxy-3-(2-fluorophenyl)-1,2-benzisoxazole in 30 ml dimethylformamide is added to a suspension of 1 g (50% suspension in oil) sodium hydride in 30 ml of dimethylformamide with stirring. Bromoacetaldehyde diethylacetal (6.2 ml) is added and the reaction mixture is heated at 80° C. for 24 hrs. The resulting dark solution is poured onto ice/water and extracted with four-100 ml portions of ether. The combined ether extracts are washed with dilute sodium hydroxide solution, saturated sodium chloride solution and dried over anhydrous magnesium sulfate. Removal of the solvent followed by recrystallization from ether/petroleum ether affords {[7-chloro-3(2-fluorophenyl)-1,2-benzisoxazol-6-yl]oxy}acetaldehyde diethyl acetal as white needles, mp 59° C.

Analysis: Calculated for C$_{19}$H$_{19}$ClFNO$_4$: 60.08%C; 5.04%H; 3.68%N. Found: 59.92%C; 4.91%H; 3.59%N.

EXAMPLE 59

To a solution of 1.00 g of hydroxylamine hydrochloride in 50 ml of 1:1 ethanol/water and 4 ml of 50% sodium hydroxide is added 5.0 g of ethyl {[7-chloro-3-(2-fluorophenyl)-1,2-benzisoxazol-6-yl]oxy}acetate in small portions, adding methanol as necessary to achieve solution. After stirring for 18 hr (a solid is formed), hydrochloric acid is added to pH 6. The solvent is evaporated, water is added to the residue and the mixture extracted with ether. The extracts are dried over anhydrous magnesium sulfate, filtered and evaporated. Recrystallization from toluene-acetonitrile affords {[7-chloro-3-(2-fluorophenyl)-1,2-benzisoxazol-6-yl]oxy}acetohydroxamic acid as a white solid mp 151° C.

Analysis: Calculated for C$_{15}$H$_{10}$ClFN$_2$O$_4$: 53.50%C; 2.99%H; 8.32%N. Found: 53.23%C; 2.94%H; 8.18%N.

EXAMPLE 60

To 12.5 g of 3-(2-fluorophenyl)-6-methoxy-4,5,7-trichloro-1,2-benzisoxazole is added 80.0 g of pyridine hydrochloride. The mixture is immersed in an oil bath at 200° C. for thirty minutes with stirring. The melt is poured into one liter of iced-hydrochloric acid solution, stirred for thirty minutes, and the resultant precipitate collected and dried to yield 3-(2-fluorophenyl)-6-hydroxy-4,5,7-trichloro-1,2-benzisoxazole, mp 110° C. (dec). To 50 ml of dry dimethylformamide is added 12 g of 3-(2-fluorophenyl)-6-hydroxy-4,5,7-trichloro-1,2-benzisoxazole, 4.4 ml of ethyl bromoacetate and 20 g of potassium carbonate. The reaction is stirred at 70° C. for 2 hrs, filtered and solvent evaporated to afford an oil, which is stirred with 500 ml water for ten minutes and then extracted with ether/ethyl acetate. The organic extract is washed with water (2X), saturated sodium chloride solution, dried over anhydrous magnesium sulfate and filtered. Evaporation of the filtrate followed by recrystallization from 95% ethanol yields ethyl {[3-(2-fluorophenyl)-4,5,7-trichloro-1,2-benzisoxazol-6-yl]oxy}acetate, mp 140°-3° C.

Analysis: Calculated for C$_{17}$H$_{11}$Cl$_3$FNO$_4$: 48.77%C; 2.65%H; 3.35%N. Found: 48.75%C; 2.55%H; 3.43%N.

EXAMPLE 61

A solution of 4.0 g of {[7-chloro-3-(2-fluorophenyl)-1,2-benzisoxazol-6-yl]oxy}acetyl chloride in methylene chloride is added dropwise to a solution of 0.9 g of methylamine hydrochloride in 50 ml methylene chloride and 25 ml of 15% sodium hydroxide solution at 0° C. After 18 hr at room temperature the reaction mixture is acidified, filtered, and the filtrate partitioned. The aqueous solution is washed with methylene chloride. The organic solutions are combined, washed with saturated sodium chloride solution and dried over magnesium sulfate. Removal of the solution gives N-methyl{[7-chloro-3-(2-fluorophenyl)-1,2-benzisoxazol-6-yl]oxy}acetamide, mp 164° C.

Analysis: Calculated for C$_{16}$H$_{12}$ClFN$_2$O$_3$: 57.40%C; 3.61%H; 8.37%N. Found: 57.13%C; 3.66%H; 8.12%N.

EXAMPLE 62

To 3.5 g of {[7-chloro-3-(2-fluorophenyl)-1,2-benzisoxazol-6-yl]oxy}acetyl chloride is added 50 ml of conc ammonium hydroxide at 0° C. After stirring for 2 hr the precipitate is filtered and washed with ice-cold acetonitrile. Recrystallization of the filter cake from acetonitrile gives }[7-chloro-3-(2-fluorophenyl)-1,2-benzisoxazol-6-yl]oxy}acetamide, mp 172° C.

Analysis: Calculated for $C_{15}H_{10}ClFN_2O_3$: 56.17%C; 3.14H; 8.74%N. Found: 56.01%C; 3.19%H; 8.57%N.

EXAMPLE 63

A solution of 3.5 g of {[7-chloro-3-(2-fluorophenyl)-1,2-benzisoxazol-6-yl]oxy}acetyl chloride in 35 ml dimethylformamide is heated at 100° C. for 4 hr. The reaction mixture is then poured into ice, acidified and extracted with ether (4×200 ml). The organic extracts are washed with saturated sodium chloride solution, dried over anhydrous magnesium sulfate, filtered and the filtrate evaporated in vacuo to afford an oil which crystallizes on trituration with ether/petroleum ether. Chromatography on silica gel affords N,N-dimethyl{[7-chloro-3-(2-fluorophenyl)-1,2-benzisoxazol-6-yl]oxy}acetamide mp 116° C.

Analysis: Calculated for $C_{17}H_{14}ClFN_2O_3$: 58.54%C; 4.04%H; 8.03%N. Found: 58.31%C; 4.00%H; 7.82%N.

EXAMPLE 64

To a suspension of 3.0 g of ethyl {[3-(2-fluorophenyl)-4,5,7-trichloro-1,2-benzisoxazol-6-yl]oxy}acetate in 50 ml of ethanol, is added 8 ml of 10% sodium hydroxide solution. After stirring at room temperature for ten minutes a solid begins to precipitate from solution. Stirring is continued for thirty minutes. Water (20 ml) is added and the precipitate dissolves. The reaction mixture is poured into 500 ml of dilute hydrochloric acid, stirred for 15 minutes, and the resultant precipitate is collected and dried at 60° C. overnight in a vacuum oven. Recrystallization from toluene yields {[3-(2-fluorophenyl)-4,5,6-trichloro-1,2-benzisoxazol-6-yl]oxy}acetic acid mp 222°–4° C.

Analysis: Calculated for $C_{15}H_7Cl_3FNO_4$: 46.12%C; 1.81%H; 3.59%N. Found: 46.38%C; 1.86%H; 3.47%N.

EXAMPLE 65

A solution of 4.0 g of 3-(4-chlorophenyl)-6-hydroxy-1,2-benzisoxazole in 20 ml dimethylformamide is added dropwise with stirring to 0.86 g of sodium hydride (50% suspension in oil) which is washed with hexane and dispersed in 20 ml dimethylformamide. A precipitate forms. When the addition is complete, the reaction mixture is stirred for 20 min and 2.28 ml of ethyl bromoacetate is added. The reaction mixture is poured into ice/water with stirring and the resultant precipitate is filtered and dried. Recrystallization from ether gives ethyl {[3-(4-chlorophenyl)-1,2-benzisoxazol-6-yl]oxy}acetate, mp 97° C.

Analysis: Calculated for $C_{17}H_{14}ClNO_4$: 61.63%C; 4.23%H Found: 61.34%C; 4.07%H

EXAMPLE 66

A solution of 4.5 g of 3-(4-chlorophenyl)-6-hydroxy-1,2-benzisoxazole in 10 ml of dimethylformamide is added dropwise to 1.0 g of sodium hydride (50% susp. in oil) which is washed with hexane and then suspended in 60 ml dimethylformamide. Ethyl-2-bromopropionate (3.67 ml) is added. The reaction mixture is poured into ice/water with stirring and the solid is collected. Recrystallization from ether affords ethyl-2-{[3-(4-chlorophenyl)-1,2-benzisoxazol-6-yl]oxy}propionate, mp 95° C.

Analysis: Calculated for $C_{18}H_{16}ClNO_4$: 62.61%C; 4.63%H. Found: 62.61%C; 4.60%H.

EXAMPLE 67

A suspension of 4 g of ethyl {[5-bromo-3-(2-fluorophenyl)-1,2-benzisoxazol-6-yl]oxy}acetate in 125 ml of ethanol, 50 ml of water and 4 ml of 50% sodium hydroxide solution is refluxed for several hours, acidified with dilute hydrochloric acid and extracted with ethyl acetate. The extract is dried, the solvent is removed and the residue is recrystallized from acetonitrile to give {[5-bromo-3-(2-fluorophenyl)-1,2-benzisoxazol-6-yl]oxy}acetic acid, mp 223°–224° C.

Analysis: Calculated for $C_{15}H_9BrFNO_4$: 49.20%C; 2.48%H; 3.83%N. Found: 49.14%C; 2.49%H; 3.76%N.

EXAMPLE 68

A solution of sodium ethoxide, prepared from 0.50 g of sodium and 15 ml of absolute ethanol is added to a stirred suspension of 6.0 g of {[7-chloro-3-(2-fluorophenyl)-1,2-benzisoxazol-6-yl]oxy}acetonitrile and 1.4 g of hydroxylamine hydrochloride in 60 ml of absolute ethanol. The reaction mixture is refluxed for 30 min, poured into water and the precipitate is collected and dried. The precipitate is dissolved in warm methanol and treated with ethereal hydrogen chloride to give N-hydroxy-{[7-chloro-3-(2-fluorophenyl)-1,2-benzisoxazol-6-yl]oxy}acetimidamide, mp 218° C. (dec.).

Analysis: Calculated for $C_{15}H_{11}ClFN_3O_3 \cdot HCl$: 48.41%C; 3.25%H; 11.29%N. Found: 48.31%C; 3.25%H; 11.32%N.

EXAMPLE 69

A solution of 5.3 g of 3-(4-chlorophenyl)-6-hydroxy-1,2-benzisoxazole in 30 ml of dimethylformamide is added dropwise to a suspension of 0.65 g of sodium hydride (50% suspension in oil) in 30 ml of dimethylformamide. After stirring for 20 min, 1.4 ml of ethyl bromoacetate is added. The reaction mixture is stirred for 1 hr, poured into water and the precipitate is collected. The precipitate is added to 30 ml of 15% sodium hydroxide solution and 30 ml methanol and heated at reflux for 3 hr. The mixture is poured into water, acidified and filtered. Recrystallization from toluene and acetonitrile gives {[3-(4-chlorophenyl)-1,2-benzisoxazol-6-yl]oxy}-acetic acid, mp 207° C.

Analysis: Calculated for $C_{15}H_{10}ClNO_4$: 59.21%C; 3.29%H. Found: 58.93%C; 3.34%H.

EXAMPLE 70 a. 2-Bromoresorcinol dimethyl ether is condensed with 2-fluorobenzoyl chloride to give 5-bromo-2'-fluoro-2-hydroxy-4-methoxybenzophenone which is reacted with hydroxylamine hydrochloride to afford E-5-bromo-2'-fluoro-2-hydroxy-4-methoxybenzophenone and converted with acetic anhydride to E-5-bromo-2'-fluoro-2-hydroxy-4-methoxybenzophenone O-acetyl oxime, all steps being performed by the process of Example 37. E-5-bromo-2'-fluoro-2-hydroxy-4-methoxybenzophenone O-acetyl oxime is cyclized to 5-bromo-3-(2-fluorophenyl)-6-methoxy-1,2-benzisoxazole and demethylated to 5-bromo-3-(2-fluorophenyl)-6-hydroxy-1,2-benzisoxazole, both steps being performed by the process of Example 35.

b. A mixture of 12 g of 5-bromo-3-(2-fluorophenyl)-6-hydroxy-1,2-benzisoxazole, 10.8 g of potassium carbonate and 7.8 g of ethyl bromoacetate in 200 ml of 2-butanone is stirred at reflux for 6 hours. The reaction mixture is filtered and the solvent removed from the filtrate under vacuum. Recrystallization of the residue from ether-chloroform-hexane gives ethyl {[5-bromo-3-(2-fluorophenyl)-1,2-benzisoxazol-6-yl]oxy}acetate, mp 130°-132° C.

Analysis: Calculated for $C_{17}H_{13}BrFNO_4$: 51.79%C; 3.33%H; 3.55%N. Found: 51.50%C; 3.10%H; 3.51%N.

EXAMPLE 71

A mixture of 11.6 g of 7-bromo-3-(2-fluorophenyl)-6-methoxy-1,2-benzisoxazole, 17.5 g of ethyl bromoacetate, 13.3 g of potassium carbonate and 100 ml of dimethylformamide is heated at 65° C. for 5 hr. The reaction mixture is poured into water and the mixture is extracted with ether. The ether extracts are washed, dried and evaporated to afford ethyl {[7-bromo-3-(2-fluorophenyl)-1,2-benzisoxazol-6-yl]oxy}acetate, mp 130°-131° C.

Analysis: Calculated for $C_{17}H_{13}BrFNO_4$: 51.79%C; 3.33%H; 3.55%N. Found: 51.95%C; 3.28%H; 3.54%N.

EXAMPLE 72

To a mixture of 4.5 g of 3-(4-chlorophenyl)-6-thiol-1,2-benzisoxazole, 5 g of potassium carbonate in 50 ml of dimethylformamide is added, with stirring, 2.00 ml of ethyl 2-bromopropionate. The mixture is heated to 95° C. for 3 hr. The reaction mixture is poured with stirring onto ice/dil hydrochloric acid. The aqueous suspension is extracted with ethyl ether (3×200 ml) and the extracts are dried over anhydrous magnesium sulfate. Evaporation of the solvent affords an oil which on trituration with isopropyl ether gives a solid. Recrystallization from isopropyl ether affords ethyl 2-{[3-(4-chlorophenyl-1,2-benzisoxazol-6-yl]thio}propionate, mp 74° C.

Analysis: Calculated for $C_{18}H_{16}ClNO_3S$: 59.83%C; 4.43%H; 8.86%S. Found: 59.84%C; 4.54%H; 8.62%S.

EXAMPLE 73

A solution of 9.0 g of 3-(4-chlorophenyl)-6-hydroxy-1,2-benzisoxazole in 25 ml of dimethylformamide is added with stirring to a suspension of 1.93 g of sodium hydride (50% suspension in oil) in 25 ml dimethylformamide. To the mixture is added 5.5 ml of ethyl 2-bromo-2-methylpropionate. The reaction mixture is stirred 24 hr at 80° C., poured onto ice/water and extracted with ether. The ether extracts are combined and washed with dil sodium hydroxide solution and dried over anhydrous magnesium sulfate. The solvent is removed in vacuo to give a yellow oil which crystallizes on standing. Recrystallization from ether affords ethyl 2-{[3-(4-chlorophenyl)-1,2-benzisoxazol-6-yl]oxy}-2-methylpropionate, mp 70° C.

Analysis: Calculated for $C_{19}H_{18}ClNO_4$: 63.51%C; 5.01%H. Found: 63.29%C; 5.07%H.

EXAMPLE 74

A mixture of 14.2 g of 7-chloro-3-(4-ethoxy-2-fluorophenyl)-6-methoxy-1,2-benzisoxazole and pyridine hydrochloride is heated at 180° C. for 2 hr. The reaction is worked up with 2-butanone and 5% hydrochloric acid and the product crystallized from toluene to give 7-chloro-3-(4-ethoxy-2-fluorophenyl)-6-hydroxy-1,2-benzisoxazole, mp 170°-172° C. The hydroxy compound is alkylated with 0.045 mole of ethyl bromoacetate and 0.043 mole of potassium carbonate in 75 ml dimethylformamide at 65° C. for 1 hr. Workup with water gives ethyl [7-chloro-3-(2-fluoro-4-ethoxyphenyl)-1,2-benzisoxazol-6-yl]oxy}acetate, mp 118°-119° C., after recrystallization from acetonitrile.

Analysis: Calculated for $C_{19}H_{17}ClFNO_5$: 57.95%C; 4.35%H; 3.56%N. Found: 58.06%C; 4.28%H; 3.52%N.

EXAMPLE 75

A mixture of 3.2 g of 3-(4-chlorophenyl)-6-mercapto-1,2-benzisoxazole, 2.52 g of potassium carbonate, 2.39 g of ethyl-2-bromo-2-methylpropionate and 75 ml dimethylformamide is heated at 60° C. for 8 hr. The reaction mixture is poured onto ice/dil hydrochloric acid and extracted with ether. The combined ether extracts are washed with dil sodium hydroxide solution, saturated sodium chloride solution and the solvent is removed in vacuo to afford a yellow oil. The oil is distilled in a Kugelrohr oven at 175° C. and 1.0 mm Hg to give an oil which crystallizes on standing. The solid is recrystallized from isopropyl ether using a brine-chilled Buchner funnel to afford ethyl 2-{[3-(4-chlorophenyl)-1,2-benzisoxazol-6-yl]thio}-2-methylpropionate.

Analysis: Calculated for $C_{19}H_{18}ClNO_3S$: 60.8%C; 4.8%H. Found: 60.7%C; 4.8%H.

EXAMPLE 76

A solution of 9.3 g of ethyl {[7-chloro-3-(2-fluoro-4-ethoxyphenyl)-1,2-benzisoxazol-6-yl]oxy}acetate in 120 ml of methylene chloride is treated with 11.3 g of boron tribromide. The mixture is refluxed for 2 hr and then an additional 3.8 g of boron tribromide is added. Another 3.8g of boron tribromide is added after 3 hr of reflux and then the reaction mixture is quenched with water after a total of 4 hr of reflux. The crude product which is isolated by diethyl ether extraction is hydrolyzed by heating under reflux in 100 ml ethanol and 150 ml 5% sodium hydroxide for 30 min. The precipitate is collected and the acid is isolated by distribution between 2-butanone and 5% hydrochloric acid and recrystallized from acetic acid. Additional product is obtained from the mother liquors by chromatography over silica gel, eluting successively with methylene chloride, 5% acetic acid/methylene chloride, 10% acetic acid/methylene chloride and 20% acetic acid/methylene chloride. The combined products are recrystallized twice from toluene/acetic acid to give {[7-chloro-3-(2-fluoro-4-hydroxyphenyl)-1,2-benzisoxazol-6-yl]oxy}acetic acid, mp 216°-218° C.

Analysis: Calculated for $C_{15}H_9ClFNO_5$: 53.35%C; 2.69%H; 4.15%N. Found: 53.68%C; 2.80%H; 4.15%N.

EXAMPLE 77

To 3.3 g of ethyl 2-{[3-(4-chlorophenyl-1,2-benzisoxazol-6-yl]oxy}butyrate and 25 ml of methanol is added 20 ml of 15% sodium hydroxide solution. The suspension is stirred at reflux for 45 min. The methanol is then removed by evaporation and the basic solution is poured into dilute hydrochloric acid/ice. The precipitate is collected and dried. The solid is recrystallized from toluene to give 2-{[3-(4-chlorophenyl)-1,2-benzisoxazol-6-yl]oxy}-2-methylpropionic acid, mp 132° C.

Analysis: Calculated for $C_{17}H_{14}ClNO_4$: 61.63%C; 4.23%H. Found: 61.78%C; 4.24%H.

EXAMPLE 78

A mixture of 6.5 g of 3-(4-chlorophenyl)-6-hydroxy-1,2-benzisoxazole, 7.5 g of potassium carbonate, 5.16 g of ethyl 2-bromobutyrate and 100 ml 2-butanone is heated under reflux with stirring for 5 hr. The reaction mixture is poured into ice/dil hydrochloric acid. The oil, which solidified on scratching, was collected and dried in vacuo. Recrystallization from isopropyl ether (decolorizing carbon) gives ethyl 2-{[3-(4-chlorophenyl)-1,2-benzisoxazol-6-yl]oxy}butyrate, mp 73° C.

Analysis: Calculated for $C_{19}H_{18}ClNO_4$: 63.51%C; 5.01%H. Found: 63.24%C; 5.06%H.

EXAMPLE 79

A solution of 3.6 g of ethyl-2-{[3-(4-chlorophenyl)-1,2-benzisoxazol-6-yl]oxy}butyrate, 30 ml of 15% sodium hydroxide solution and 30 ml of methanol, is stirred under reflux for 3 hr. The methanol is evaporated and the solution is poured into dilute hydrochloric acid/ice affording a flocculant precipitate. The precipitate is collected, dried in vacuo and recrystallized from toluene to afford 2-{[3-(4-chlorophenyl)-1,2-benzisoxazol-6-yl]oxy}butyric acid, mp 144° C.

Analysis: Calculated for $C_{17}H_{14}ClNO_4$: 61.63%C; 4.24%H. Found: 61.59%C; 4.27%H.

EXAMPLE 80

A solution of 3.7 g of ethyl 2-{[3-(4-chlorophenyl)-1,2-benzisoxazol-6-yl]thio}-2-methylpropionate, 30 ml of 15% sodium hydroxide solution and 30 ml of methanol, is stirred under reflux for 3 hr. The methanol is evaporated and the aqueous solution poured into ice/dilute hydrochloric acid. The precipitate is collected, dried and recrystallized from toluene to afford 2-{[3-(4-chlorophenyl)-1,2-benzisoxazol-6-yl]thio}-2-methylpropionic acid, mp 176°-7° C.

Analysis: Calculated for $C_{17}H_{14}ClNO_3S$: 58.78%C; 4.03%H. Found: 58.81%C; 4.08%H.

EXAMPLE 81

A solution of 6 g of 3-(4-chlorophenyl)-6-hydroxy-1,2-benzisoxazole, 10.2 g of potassium carbonate, 5.12 g of ethyl 2-bromovalerate and 100 ml of methylethyl ketone is stirred under reflux for 3 hr. The reaction mixture is poured into 1 liter of ice/dil hydrochloric acid and the precipitate is collected and dried. Recrystallization from ether gives ethyl 2-{[3-(4-chlorophenyl)-1,2-benzisoxazol-6-yl]oxy}pentanoate, mp 88° C.

Analysis: Calculated for $C_{20}H_{20}ClNO_4$: 64.34%C; 5.36%H. Found: 64.20%C; 5.37%H.

EXAMPLE 82

A solution of 3.5 g of ethyl 2-{[3-(4-chlorophenyl)-1,2-benzisoxazol-6-yl]oxy}pentanoate, 30 ml 15% sodium hydroxide and 30 ml methanol is heated under reflux for 1.5 hr. The reaction mixture is poured into ice/dil hydrochloric acid with stirring. The precipitate is collected, washed with water and dried in vacuo. Recrystallization from toluene/acetonitrile affords 2-{[3-(4-chlorophenyl)-1,2-benzisoxazol-6-yl]oxy}pentanoic acid, mp 170° C.

Analysis: Calculated for $C_{18}H_{16}ClNO_4$: 62.60%C; 4.63%H. Found: 62.42%C; 4.65%H.

EXAMPLE 83

A solution of 8 g of 7-chloro-3-(2-fluorophenyl)-6-thiol-1,2-benzisoxazole, 12.0 g of potassium carbonate, 7.2 ml of ethyl-2-bromoisobutyrate and 150 ml of 2-butanone is heated under reflux for 2 hr. The reaction mixture is poured into 1 liter of ice and water and extracted with ether (3×300 ml). The combined organic extracts are washed with saturated sodium chloride solution, dried over anhydrous magnesium sulfate and the solvent is evaporated at reduced pressure to give an oil, which crystallized on standing. Recrystallization from hexane containing a little ether gives ethyl 2-{[7-chloro-3-(2-fluorophenyl)-1,2-benzisoxazol-6-yl]thio}-2-methylpropionate, mp 83.4° C.

Analysis: Calculated for $C_{19}H_{17}ClFNO_3S$: 57.93%C; 4.35%H. Found: 57.65%C; 4.34%H.

EXAMPLE 84

A mixture of 5.0 g of ethyl 2-{[7-chloro-3-(2-fluorophenyl)-1,2-benzisoxazol-6-yl]thio}-2-methylpropionate, 30 ml of 15% sodium hydroxide and 30 ml of methanol is heated under reflux for 2 hr. The reaction mixture is poured into ice/conc hydrochloric acid. The precipitate is collected, dried and recrystallized from toluene to afford 2-{[7-chloro-3-(2-fluorophenyl)-1,2-benzisoxazol-6-yl]thio}-2-methylpropionic acid, mp 149° C.

Analysis: Calculated for $C_{17}H_{13}ClFNO_3S$: 55.89%C; 3.56%H. Found: 55.74%C; 3.53%H.

EXAMPLE 85

A solution of 7.32 g of {[7-bromo-3-(2-fluorophenyl)-1,2-benzisoxazol-6-yl]oxy}acetic acid, 135 ml of dry tetrahydrofuran and 2.02 g of triethylamine is added dropwise to a solution of 2.16 g of ethyl chloroformate in ice-cold tetrahydrofuran. The precipitate is filtered off. A solution of 0.80 g of sodium hydroxide in 25 ml of hot methanol is added to a solution of 1.4 g of hydroxylamine hydrochloride in 25 ml of hot methanol. The precipitate is collected. The solution is added to the tetrahydrofuran filtrate. The reaction mixture is warmed for 15 min of a steam bath, poured into water and extracted with 2-butanone. Evaporation and recrystallization from nitromethane gives {[7-bromo-3-(2-fluorophenyl)-1,2-benzisoxazol-6-yl]oxy}acetohydroxamic acid, mp 165°-167° C.

Analysis: Calculated for $C_{15}H_{10}BrFN_2O_4.0.2H_2O$: 46.71%C; 2.74%H; 7.27%N. Found: 46.65%C; 2.63%H; 6.99%N.

EXAMPLE 86 a. To a mixture of 30 g of 2,5-difluorobenzoyl chloride and 23.5 g of 1,3-dimethoxybenzene in 300 ml 1,2-dichloroethane, 23 g of aluminum chloride is added in portions with the internal temperature maintained at approximately 8°-12° C. The reaction mixture is stirred 0.5 hr and refluxed one hr. The reaction mixture is poured into concentrated hydrochloric acid and ice. The organic layer is separated, washed, dried over anhydrous sodium sulfate and evaporated. Trituration of the crude residue gives 2',5'-difluoro-2-hydroxy-4-methoxybenzophenone, mp 109° C. followed by recrystallization from toluene.

Analysis: Calculated for $C_{14}H_{10}F_2O_3$: 63.64%C; 3.81%H. Found: 64.01%C; 3.80%H.

b. A mixture of 40 g of 2',5'-difluoro-2-hydroxy-4-methoxybenzophenone hydrochloride and 230 ml of pyridine is refluxed overnight. The pyridine is evaporated in vacuo. The residue is partitioned between 5% hydrochloric acid and ethyl acetate. The ethyl acetate solution is dried over anhydrous sodium sulfate and evaporated. The residue was triturated with hexane to give E-2',5'-difluoro-2-hydroxy-4-methoxybenzophenone oxime. A mixture of 35 g of the oxime and 25.6 g of acetic anhydride is placed in an oil bath at 60° C. for 45 min. The reaction mixture is partitioned between ether and sodium bicarbonate solution. The ether extract is dried over anhydrous sodium sulfate and evaporated. Recrystallization of the residue from 95% ethanol gives 30 g of E-2',5'-difluoro-2-hydroxy-4-methoxybenzophenone O-acetyl oxime, mp 110°-111° C.

Analysis: Calculated for $C_{16}H_{13}F_2NO_4$: 59.81%C; 4.07%H. Found: 59.67%C; 3.84%H.

c. To a mixture of 34 g of E-2',5'-difluoro-2-hydroxy-4-methoxybenzophenone O-acetyl oxime in 70 ml dimethylformamide at 65° C., 18.2 g of potassium carbonate is added. The mixture is stirred for 45 min and poured into water. The precipitate is collected and dried. Recrystallization from ether gives 3-(2,5-difluorophenyl)-6-methoxy-1,2-benzisoxazole, mp 121°-122° C.

Analysis: Calculated for $C_{14}H_9F_2NO_2$: 63.64%C; 3.81%H. Found: 63.79%C; 3.75%H.

d. 3-(2,5-Difluorophenyl)-6-methoxy-1,2-benzisoxazole may be demethylated by the procedure described in Example 60 to 3-(2,5-difluorophenyl)-6-hydroxy-1,2-benzisoxazole which in turn may be condensed with ethyl bromoacetate according to the method described in Example 60 to ethyl {[3-(2,5-difluorophenyl-1,2-benzisoxazol-6-yl]oxy}acetate and hydrolyzed by the process disclosed in Example 64 to {[3-(2,5-difluorophenyl-1,2-benzisoxazol-6-yl]oxy}acetic acid.

EXAMPLE 87 a. To a mixture of 20 g of 2,6-difluorobenzoyl chloride and 15.5 g of 1,3-dimethoxybenzene in 200 ml of 1,2-dichloroethane, 15.28 g of aluminum chloride is added in portions with the internal temperature maintained at 0°-10° C. The mixture is stirred 1 hour and then refluxed 45 min. The reaction mixture is poured into concentrated hydrochloric acid and ice. The organic layer is separated, washed, dried over anhydrous sodium sulfate and evaporated. Trituration with hexane followed by recrystallization from 95% ethanol gives 2',6'-difluoro-2-hydroxy-4-methoxybenzophenone, mp 71°-72° C.

Analysis: Calculated for $C_{14}H_{10}F_2O_3$: 63.64%C; 3.81%H. Found: 63.79%C; 3.75%H.

b. 2',6'-Difluoro-2-hydroxy-4-methoxybenzophenone may be condensed with hydroxylamine to E-2',6'-difluoro-2-hydroxy-4-methoxybenzophenone oxime which in turn may be converted to E-2',6'-difluoro-2-hydroxy-4-methoxybenzophenone O-acetyl oxime and cyclized to 3-(2,6-difluorophenyl)-6-methoxy-1,2-benzisoxazole, all steps being performed by the procedures described in Example 86. 3-(2',6'-Difluorophenyl)-6-methoxy-1,2-benzisoxazole then may be demethylated to 3-(2,6-difluorophenyl)-6-hydroxy-1,2-benzisoxazole and condensed with ethyl bromoacetate to ethyl {[3-(2,6-difluorophenyl-1,2-benzisoxazol-6-yl]oxy}acetate both steps being performed by the methods disclosed in Example 64. Ethyl {[3-(2,6-difluorophenyl-1,2-benzisoxazol-6-yl]oxy}acetate may be hydrolyzed to {[3-(2,6-difluorophenyl-1,2-benzisoxazol-6-yl]oxy}acetic acid.

EXAMPLE 88 a. 4'-Chloro-2-hydroxy-4-methoxybenzophenone is prepared by condensing resorcinal dimethyl ether with 4-chlorobenzoyl chloride in the presence of aluminum chloride according to the procedure of Example 37.

b. A mixture of 382 g of 4'-chloro-2-hydroxy-4-methoxybenzophenone, 230 g hydroxylamine hydrochloride and 1.5 liters of pyridine is heated under reflux for 3 hr. The solvent is evaporated and the residue is partitioned between hydrochloric acid and ethyl acetate. The organic extracts are combined and washed with saturated sodium chloride solution. The solvent is removed to afford a mixture of E- and Z-oxime isomers which is separated on a Waters Prep IC System 500 using 5% ethyl acetate/toluene as the eluting system to afford E-4'-chloro-2-hydroxy-4-methoxybenzophenone oxime, mp 159° C.

Analysis: Calculated for $C_{14}H_{12}ClNO_3$: 60.64%C; 4.34%H. Found: 60.54%C; 4.33%H.

EXAMPLE 89

A solution of E- and Z-4'-chloro-2-hydroxy-4-methoxybenzophenone and 19 ml acetic anhydride is heated for 1 hr at 60° C. The reaction mixture is poured into ice-water and extracted with chloroform. The extracts are dried over anhydrous magnesium sulfate and the solvent is evaporated. Recrystallization from ether hexane affords E-4'-chloro-2-hydroxy-4-methoxybenzophenone-O-acetyl oxime, mp 167° C.

Analysis: Calculated for $C_{16}H_{14}ClNO_4$: 60.18%C; 4.38%H. Found: 59.97%C; 4.38%H.

EXAMPLE 90

A mixture of 5.32 g of E-4'-chloro-2-hydroxy-4-methoxybenzophenone-O-acetyl oxime, 3.45 g of potassium carbonate and 50 ml of 2-butanone is heated under reflux at 80° C. for 2 hr. The reaction mixture is poured into water/ice. The precipitate is filtered, dried, and recrystallized from toluene/ether to give 3-(4-chlorophenyl)-6-methoxy-1,2-benzisoxazole, mp 148°-9° C.

Analysis: Calculated for $C_{14}H_{10}ClNO_2$: 64.86%C; 3.86%H. Found: 64.49%C; 3.90%H.

EXAMPLE 91 a. A mixture of 60 g of pyridine hydrochloride and 12.0 g 3-(4-chlorophenyl)-6-methoxy-1,2-benzisoxazole is heated with stirring at 210° C. for 75 min. The hot reaction mixture is poured with vigorous stirring onto ice and the solid is filtered, dried, and recrystallized from toluene to afford 3-(4-chlorophenyl)-6-hydroxy-1,2-benzisoxazole, mp 203° C.

Analysis: Calculated for $C_{13}H_8ClNO_2$: 63.67%C; 3.26%H. Found: 63.39%C; 3.27%H.

b. 3-(4-chlorophenyl)-6-hydroxy-1,2-benzisoxazole is converted to 6-(O,N,N-dimethylthiocarbamyl)-3-(4-chlorophenyl)-1,2-benzisoxazole which is thermally rearranged to 6-(S,N,N-dimethylthiocarbamyl)-3-(4-chlorophenyl)-1,2-benzisoxazole and hydrolyzed to 3-(4-chlorophenyl)-6-mercapto-1,2-benzisoxazole, all steps being performed according to the processes of Example 43.

EXAMPLE 92

To 29.8 g of 2,3-dichloro-4-methoxybenzoyl chloride in 150 ml of 1,2-dichloroethane, 16.3 g of m-fluorophenetole is added. The solution is chilled to 5° C. as 16.5 g of aluminum chloride is added slowly. After 2 hr, the reaction mixture is worked up with water and diethyl ether to give a mixture of 2,3-dichloro-4'-ethoxy-2'-fluoro-4-methoxybenzophenone and 2,3-dichloro-2'-ethoxy-4'-fluoro-4-methoxybenzophenone. The mixture is separated by preparative high pressure liquid chromatography (10% ethyl acetate/hexane 250 ml/min) to give 2,3-dichloro-4'-ethoxy-2'-fluoro-4-methoxybenzophenone, mp 94°–96° C.

Analysis: Calculated for $C_{16}H_{13}Cl_2FO_3$: 55.99%C; 3.82%H. Found: 55.86%C; 3.81%H.

EXAMPLE 93

A mixture of 26.7 g of 2,3-dichloro-4'-ethoxy-2'-fluoro-4-methoxybenzophenone, in 250 ml of pyridine and 18.0 g of hydroxylamine hydrochloride is heated under reflux overnight. Workup with 5% hydrochloric acid and diethyl ether gives diethyl ether insoluble product. The diethyl ether filtrate is evaporated and the residue hydrolyzed overnight in 150 ml of 1:1 ethanol/water containing 15 g of sodium bisulfite. Workup with 5% hydrochloric acid/diethyl ether gives after filtration through silica gel (toluene) starting ketone. Repetition of the hydroxylamine hydrochloride in pyridine reaction gives additional Z-oxime. Recrystallization from toluene gives Z-2,3-Dichloro-4'-ethoxy-2'-fluoro-4-methoxybenzophenone oxime, mp 188°–189° C.

Analysis: Calculated for $C_{16}H_{14}Cl_2FNO_3$: 53.65%C; 3.94%H; 3.91%N. Found: 53.66%C; 4.06%H; 3.77%N.

EXAMPLE 94

A solution of 23.3 g of Z-2,3-dichloro-4'-ethoxy-2'-fluoro-4-methoxybenzophenone oxime in 175 ml dimethylformamide is added to 1.85 g of sodium hydride in 35 ml of dimethylformamide. After stirring 30 min at room temperature, the reaction is worked up with water and 1:1 diethyl ether/2-butanone. Concentration of the dried organic phase, trituration of the product with hexane and recrystallization from toluene/hexane gives 7-chloro-3-(4-ethoxy-2-fluorophenyl)-6-methoxy-1,2-benzisoxazole, mp 151°–152° C.

Analysis: Calculated for $C_{16}H_{13}ClFNO_3$: 59.73%C; 4.07%H; 4.35%N. Found: 59.54%C; 4.13%H; 4.31%N.

EXAMPLE 95

To 29.8 g of 2,3-dichloro-4-methoxybenzoyl chloride in 150 ml of 1,2-dichloroethane is added 16.3 g of m-fluorophenetole. The solution is chilled to 5° C. as 16.5 g of aluminum chloride is added slowly. After 2 hr, the reaction mixture is worked up with water and diethyl ether to give a mixture of 2,3-dichloro-2'-ethoxy-4'fluoro-methoxybenzophenone and 2,3-dichloro-4'-ethoxy-2'-fluoro-4-methoxybenzophenone. The mixture is separated by preparative high pressure liquid chromatography (10% ethyl acetate/hexane; 250 ml/min) to give 2,3-dichloro-2'-ethoxy-4'-fluoro-4-methoxybenzophenone, mp 107°–109° C., after recrystallization from cyclohexane.

Analysis: Calculated for $C_{16}H_{13}Cl_2FO_3$: 55.99%C; 3.82%H. Found: 55.83%C; 3.77%H.

EXAMPLE 96 a. A mixture of 12.0 g of 2,3-dichloro-2'-ethoxy-4'-fluoro-4-methoxybenzophenone in 100 ml of pyridine containing 7.0 g of hydroxylamine hydrochloride is heated under reflux for 3 hr. A standard work up with 5% hydrochloric acid and diethyl ether gives E- and Z-2,3-dichloro-2'-ethoxy-4'-fluoro-4-methoxybenzophenone oxime. The mixture of oximes is dissolved in 60 ml of dimethylformamide and 40 ml of tetrahydrofuran and added to a suspension of 2.1 g of 50% sodium hydride in 100 ml of tetrahydrofuran. The reaction mixture is refluxed 2.5 hr. Workup with water and diethyl ether gives crystalline material. Two recrystallizations from acetonitrile give 7-Chloro-3-(2-ethoxy-4-fluorophenyl)-6-methoxy-1,2-benzisoxazole, mp 150°–152° C.

Analysis: Calculated for $C_{16}H_{13}ClFNO_3$: 59.73%C; 4.07%H; 4.35%N. Found: 59.63%C; 4.11%H; 4.41%N.

b. 7-chloro-3-(2-ethoxy-4-fluorophenyl)-6-methoxy-1,2-benzisoxazole may be demethylated to 7-chloro-3-(2-ethoxy-4-fluorophenyl)-6-hydroxy-1,2-benzisoxazole which may be condensed ethyl bromoacetate to ethyl {[7-chloro-3-(2-ethoxy-4-fluorophenyl)-1,2-benzisoxazol-6-yl]oxy}acetate, both steps may be performed by the process of Example 74. Ethyl {[7-chloro-3-(2-ethoxy-4-fluorophenyl)-1,2-benzisoxazol-6-yl]oxy}acetate may be hydrolyzed to {[7-chloro-3-(2-ethoxy-4-fluorophenyl)-1,2-benzisoxazol-6-yl]oxy}acetic acid by the method of Example 64.

We claim:
1. A compound depicted by the formula

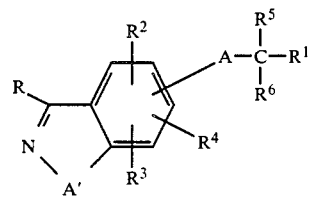

wherein
R is naphthyl,

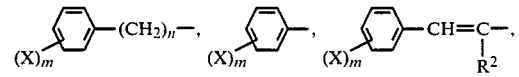

thienyl, furyl, pyrryl, pyridyl, or pyridyl N-oxide;
$R^1$ is a free or esterified carboxyl group of 1 to 8 carbon atoms,

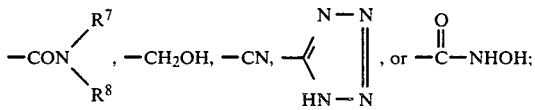

$R^2$, $R^3$ and $R^4$ are the same or different and each can be hydrogen, halogen, or loweralkyl of 1 to 4 carbon atoms;
X is hydrogen, halogen, loweralkyl of 1 to 4 carbon atoms, loweralkoxy of 1 to 4 carbon atoms, loweralkylthio of 1 to 4 carbon atoms, hydroxy, trifluoromethyl, nitro, amino or acylamino;
$R^5$, $R^6$, $R^7$, and $R^8$ are the same or different and can be hydrogen or loweralkyl of 1 to 4 carbon atoms;
A and A' are the same or different and can be O or S; and
m and n are the same or different and each can be the integer 1, 2 or 3;
or a physiologically acceptable salt thereof.

2. A compound according to claim 1 depicted by the formula

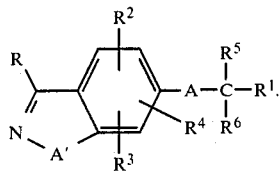

3. A compound according to claim 1 depicted by the formula

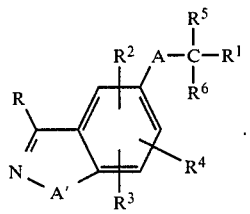

4. A compound according to claim 1 depicted by the formula

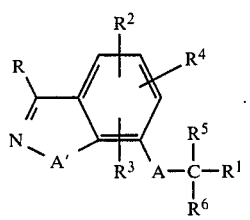

5. A compound according to claim 1 in which R is

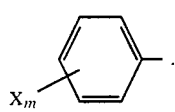

6. A compound according to claim 5 depicted by the formula

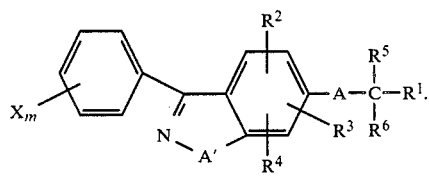

7. A compound according to claim 6 in which $R^1$ is COOH.

8. A compound according to claim 5 depicted by the formula

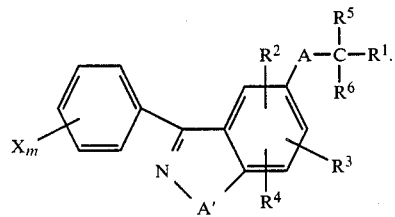

9. A compound according to claim 8 in which $R^1$ is COOH.

10. A compound according to claim 5 depicted by the formula

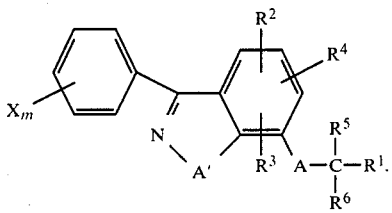

11. A compound according to claim 10 in which $R^1$ is COOH.

12. A compound according to claim 1 in which A and A' are O.

13. A compound according to claim 12 depicted by the formula

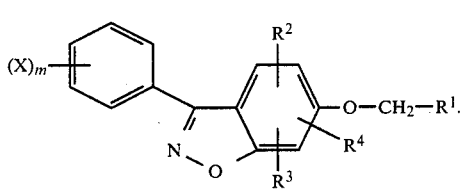

14. A compound according to claim 13 in which $R^1$ is COOH.

15. A compound according to claim 1 in which A is S and A' is O.

16. A compound according to claim 15 depicted by the formula

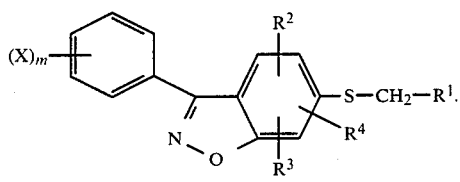

17. A compound according to claim 16 in which $R^1$ is COOH.

18. A compound according to claim 1 in which A is O and A' is S.

19. A compound according to claim 18 depicted by the formula

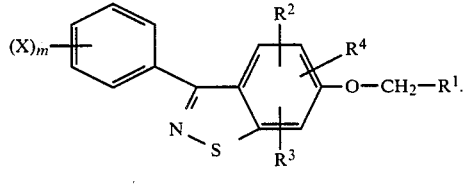

20. A compound according to claim 19 in which $R^1$ is COOH.

21. A compound according to claim 1 in which R is thienyl, furyl, pyrryl, pyridyl or pyridyl N-oxide.

22. A compound according to claim 1 depicted by the formula

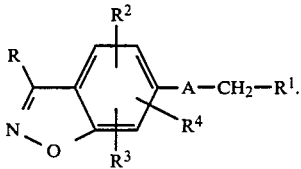

23. A compound according to claim 22 in which R¹ is COOH.

24. A compound according to claim 1 in which A and A' are S.

25. A compound according to claim 24 depicted by the formula

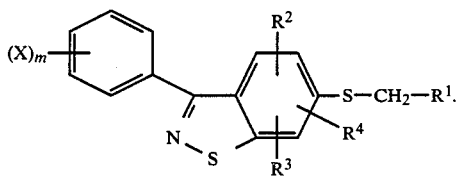

26. A compound according to claim 25 in which R¹ is COOH.

27. The compound defined in claim 1 which is {[7-chloro-3-(2-fluorophenyl)-1,2-benzisoxazol-6-yl]oxy}acetic acid.

28. The compound defined in claim 1 which is ethyl{[7-chloro-3-(2-thienyl)-1,2-benzisoxazole-6-yl]oxy}acetate.

29. The compound defined in claim 1 which is ethyl{[7-chloro-3-(2-fluorophenyl)-1,2-benzisoxazol-6-yl)oxy}acetate.

30. The compound defined in claim 1 which is ethyl[(7-chloro-3-phenyl-1,2-benzisoxazol-6-yl)oxy-]acetate.

31. The compound defined in claim 1 which is [(7-chloro-3-phenyl-1,2-benzisoxazol-6-yl)oxy]acetic acid.

32. The compound defined in claim 1 which is ethyl{[7-chloro-3-(2-furyl)-1,2-benzisoxazol-6-yl]oxy-}acetate.

33. The compound defined in claim 1 which is {[7-chloro-3-(2-furyl)-1,2-benzisoxazol-6-yl]oxy}acetic acid.

34. The compound defined in claim 1 which is {[7-chloro-3-(3-methyl-2-thienyl)-1,2-benzisoxazol-6-yl]oxy}acetic acid.

35. The compound defined in claim 1 which is ethyl{[7-chloro-3-(5-methyl-2-furyl)-1,2-benzisoxazol-6-yl]oxy}acetate.

36. The compound defined in claim 1 which is {[7-chloro-3-(5-methyl-2-furyl)-1,2-benzisoxazol-6-yl]oxy}acetic acid.

37. The compound defined in claim 1 which is ethyl {[7-chloro-3-(4-tolyl)-1,2-benzisoxazol-6-yl]oxy}acetate.

38. The compound defined in claim 1 which is {[7-chloro-3-(4-tolyl)-1,2-benzisoxazol-6-yl]oxy}acetic acid.

39. The compound defined in claim 1 which is ethyl {[7-chloro-3-(4-chlorophenyl)-1,2-benzisoxazol-6-yl]oxy}acetate.

40. The compound defined in claim 1 which is {[7-chloro-3-(4-chlorophenyl)-1,2-benzisoxazol-6-yl]oxy}acetic acid.

41. The compound defined in claim 1 which is ethyl {[7-chloro-3-(5-methyl-2-thienyl)-1,2-benzisoxazol-6-yl]oxy}acetate.

42. The compound as defined in claim 1 which is {[7-chloro-3-(2-thienyl)-1,2-benzisoxazol-6-yl]-oxy}acetic acid.

43. The compound as defined in claim 1 which is {[7-chloro-3-(5-methyl-2-thienyl)-1,2-benzisoxazol-6-yl]oxy}acetic acid.

44. The compound as defined in claim 1 which is {[7-chloro-3-(3-furyl)-1,2-benziosoxazol-6-yl)oxy}acetic acid.

45. The compound as defined in claim 1 which is {[7-chloro-3-(2,6-difluorophenyl)-1,2-benzisoxazol-6-yl]oxy}acetic acid.

46. The compound as defined in claim 1 which is {[7-chloro-3-(trans-β-fluorostyryl-1,2-benzisoxazol-6-yl]oxy}acetic acid.

47. The compound as defined in claim 1 which is {[7-chloro-3-(2,4-difluorophenyl)-1,2-benzisoxazol-6-yl]-oxy}acetic acid.

48. The compound as defined in claim 1 which is {[5-chloro-3-(2-fluorophenyl)-1,2-benzisoxazol-6-yl]-oxy}acetic acid.

49. The compound as defined in claim 1 which is {[7-chloro-3-(3,4-dichlorophenyl)-1,2-benzisoxazol-6-yl]-oxy}acetic acid.

50. The compound as defined in claim 1 which is {[7-chloro-3-(2-chlorophenyl)-1,2-benzisoxazol-6-yl]oxy}acetic acid.

51. The compound as defined in claim 1 which is {[7-chloro-3-(2-tolyl)-1,2-benzisoxazol-6-yl]oxy}acetic acid.

52. The compound as defined in claim 1 which is ethyl {[7-chloro-3-(1-naphthyl)-1,2-benzisoxazol-6-yl]oxy}acetate.

53. The compound as defined in claim 1 which is {[7-chloro-3-(1-naphthyl)-1,2-benzisoxazol-6-yl]oxy}-acetic acid.

54. The compound as defined in claim 1 which is ethyl{[7-chloro-3-(2,3-dimethylphenyl)-1,2-benzisoxazol-6-yl]oxy}acetate.

55. The compound as defined in claim 1 which is {[7-chloro-3-(2,3-dimethylphenyl)-1,2-benzisoxazol-6-yl]oxy}acetic acid.

56. The compound as defined in claim 1 which is {[7-chloro-3-(3-fluorophenyl)-1,2-benzisoxazol-6-yl]-oxy}acetic acid.

57. The compound as defined in claim 1 which is {[7-chloro-3-(2-pyridyl)-1,2-benzisoxazol-6-yl]oxy}acetic acid.

58. The compound as defined in claim 1 which is {[7-chloro-3-(2-pyridyl)-1,2-benzisoxazol-6-yl]oxy}acetic acid 1'-oxide.

59. The compound as defined in claim 1 which is {[3-(2-fluorophenyl)-1,2-benzisoxazol-6-yl]oxy}acetic acid.

60. The compound as defined in claim 1 which is {[7-chloro-3-(4-fluorophenyl)-1,2-benzisoxazol-6-yl]oxy}acetic acid.

61. The compound as defined in claim 1 which is {[3-(2-fluorophenyl)-7-methyl-1,2-benzisoxazol-6-yl]oxy}acetic acid.

62. The compound as defined in claim 1 which is {[7-chloro-3-(4-chloro-2-fluorophenyl)-1,2-benzisoxazol-6-yl]oxy}acetic acid.

63. The compound as defined in claim 1 which is {[3-(2-fluorophenyl)-7-iodo-1,2-benzisoxazol-6-yl]oxy}acetic acid.

64. The compound as defined in claim 1 which is {[7-bromo-3-(2-fluorophenyl)-1,2-benzisoxazol-6-yl]oxy}acetic acid.

65. The compound as defined in claim 1 which is ethyl {[3-benzyl-7-chloro-1,2-benzisoxazol-6-yl]oxy}acetate.

66. The compound as defined in claim 1 which is {(3-benzyl-7-chloro-1,2-benzisoxazol-6-yl)oxy}acetic acid.

67. The compound as defined in claim 1 which is ethyl{[5,7-dichloro-3-(2-fluorophenyl)-1,2-benzisoxazol-6-yl]oxy}acetate.

68. The compound as defined in claim 1 which is {[5,7 dichloro-3-(2-fluorophenyl)-1,2-benzisoxazol-6-yl]oxy}acetic acid.

69. The compound as defined in claim 1 which is ethyl {[7-chloro-3-(2-fluorophenyl)-1,2-benzisoxazol-6-yl]thio}acetate.

70. The compound as defined in claim 1 which is {[5,7-dichloro-3-(2-fluorophenyl)-1,2-benzisoxazol-6-yl]thio acetic acid.

71. The compound as defined in claim 1 which is {[4-chloro-3-(2-fluorophenyl)-1,2-benzisoxazol-6-yl]oxy}acetic acid.

72. The compound as defined in claim 1 which is {[7-chloro-3-(2,3-difluorophenyl)-1,2-benzisoxazol-6-yl]-oxy}acetic acid.

73. The compound as defined in claim 1 which is ethyl-2-{[7-chloro-3-(2-fluorophenyl)-1,2-benzisoxazole-6-yl]oxy}propionate.

74. The compound as defined in claim 1 which is 2-{[7-chloro-3-(2-fluorophenyl)-1,2-benzisoxazole-6-yl]oxy}propionic acid.

75. The compound as defined in claim 1 which is {[7-chloro-3-(2,5-difluorophenyl)-1,2-benzisoxazol-6-yl]oxy}acetic acid.

76. The compound as defined in claim 1 which is [(7-chloro-1,2-benzisoxazol-6-yl)oxy]acetic acid.

77. The compound as defined in claim 1 which is {[7-chloro-3-(2-trifluoromethylphenyl)-1,2-benzisoxazol-6-yl]oxy}acetic acid.

78. The compound as defined in claim 1 which is {[7-chloro-3-(2-hydroxyphenyl)-1,2-benzisoxazol-6-yl]oxy}acetic acid.

79. The compound as defined in claim 1 which is [4,5,7-trichloro-3-(2-fluorophenyl)-1,2-benzisoxazol-6-yl]oxy acetic acid.

80. The compound as defined in claim 1 which is [7-chloro-3-(2-fluorophenyl)-1,2-benzisoxazol-6-yl]oxy acetonitrile.

81. The compound as defined in claim 1 which is ethyl-2-{[7-chloro-3-(2-fluorophenyl)-1,2-benzisoxazole-6-yl]oxy}-2-methyl propionate.

82. The compound as defined in claim 1 which is {[7-chloro-3-(2-methoxy-5-nitrophenyl)-1,2-benzisoxazol-6-yl]oxy}acetic acid.

83. The compound as defined in claim 1 which is {[7-chloro-3-(2-fluorophenyl)-1,2-benzisoxazol-6-yl]oxy}acetohydroxamic acid.

84. The compound as defined in claim 1 which is ethyl {[3-(2-fluorophenyl)-4,5,7-trichloro-1,2-benzisoxazol-6-yl]oxy}acetate.

85. The compound as defined in claim 1 which is N-methyl-{[7-chloro-3-(2-fluorophenyl)-1,2-benzisoxazol-6-yl]oxy}acetamide.

86. The compound as defined in claim 1 which is {[7-chloro-3-(2-fluorophenyl)-1,2-benzisoxazol-6-yl]oxy}acetamide.

87. The compound as defined in claim 1 which is N,N-dimethyl {[7-chloro-3-(2-fluorophenyl)-1,2-benzisoxazol-6-yl]oxy}acetamide.

88. The compound as defined in claim 1 which is {[3-(2-fluorophenyl)-4,5,7-trichloro-1,2-benzisoxazol-6-yl]oxy}acetic acid.

89. The compound as defined in claim 1 which is ethyl {[3-(4-chlorophenyl)-1,2-benzisoxazol-6-yl]oxy}acetate.

90. The compound as defined in claim 1 which is ethyl 2-{[3-(4-chlorophenyl)-1,2-benzisoxazol-6-yl]oxy} propionate.

91. The compound as defined in claim 1 which is {[5-bromo-3-(2-fluorophenyl)-1,2-benzisoxazol-6-yl]oxy}acetic acid.

92. The compound as defined in claim 1 which is {[3-(4-chlorophenyl)-1,2-benzisoxazol-6-yl]oxy}acetic acid.

93. The compound as defined in claim 1 which is ethyl {[5-bromo-3-(2-fluorophenyl)-1,2-benzisoxazol-6-yl]oxy}acetate.

94. The compound as defined in claim 1 which is ethyl {[7-bromo-3-(2-fluorophenyl)-1,2-benzisoxazol-6-yl]oxy}acetate.

95. The compound as defined in claim 1 which is ethyl 2-{[3-(4-chlorophenyl)-1,2-benzisoxazol-6-yl]thio}propionate.

96. The compound as defined in claim 1 which is ethyl 2-{[3-(4-chlorophenyl)-1,2-benzisoxazol-6-yl]oxy}-2-methylpropionate.

97. The compound as defined in claim 1 which is ethyl {[7-chloro-3-(2-fluoro-4-ethoxyphenyl)-1,2-benzisoxazol-6-yl]oxy}acetate.

98. The compound as defined in claim 1 which is ethyl 2-{[3-(4-chlorophenyl)-1,2-benzisoxazol-6-yl]thio}-2-methylpropionate.

99. The compound as defined in claim 1 which is {[7-chloro-3-(2-fluoro-4-hydroxyphenyl)-1,2-benzisoxazol-6-yl]oxy}acetic acid.

100. The compound as defined in claim 1 which is 2-{[3-(4-chlorophenyl)-1,2-benzisoxazol-6-yl]oxy}-2-methylpropionic acid.

101. The compound as defined in claim 1 which is ethyl 2-{[3-(4-chlorophenyl)-1,2-benzisoxazol-6-yl]oxy} butyrate.

102. The compound as defined in claim 1 which is 2-{[3-(4-chlorophenyl)-1,2-benzisoxazol-6-yl]oxy} butyric acid.

103. The compound as defined in claim 1 which is 2-{[3-(4-chlorophenyl)-1,2-benzisoxazol-6-yl]thio}-2-methylpropionic acid.

104. The compound as defined in claim 1 which is ethyl 2-{[3-(4-chlorophenyl)-1,2-benzisoxazol-6-yl]oxy} pentanoate.

105. The compound as defined in claim 1 which is 2-{[3-(4-chlorophenyl)-1,2-benzisoxazol-6-yl]oxy}pentanoic acid.

106. The compound as defined in claim 1 which is ethyl 2-{[7-chloro-3-(2-fluorophenyl)-1,2-benzisoxazol-6-yl]thio}-2-methylpropionate.

107. A compound as defined in claim 1 which is 2-{[7-chloro-3-(2-fluorophenyl)-1,2-benzisoxazol-6-yl]thio}-2-methylpropionic acid.

108. A compound as defined in claim 1 which is {[7-bromo-3-(2-fluorophenyl)-1,2-benzisoxazol-6-yl]oxy}acetohydroxamic acid.

109. A compound as defined in claim 1 which is ethyl {[3-(2,5-difluorophenyl)-1,2-benzisoxazol-6-yl]oxy}acetate.

110. A compound as defined in claim 1 which is {[3-(2,5-difluorophenyl)-1,2-benzisoxazol-6-yl]oxy}acetic acid.

111. A compound as defined in claim 1 which is ethyl {[3-(2,6-difluorophenyl)-1,2-benzisoxazol-6-yl]oxy}acetate.

112. A compound as defined in claim 1 which is {[3-(2,6-difluorophenyl)-1,2-benzisoxazol-6-yl]oxy}acetic acid.

113. A compound as defined in claim 1 which is ethyl {[7-chloro-3-(2-ethoxy-4-fluorophenyl)-1,2-benzisoxazol-6-yl]oxy}acetate.

114. A compound as defined in claim 1 which is {[7-chloro-3-(2-ethoxy-4-fluorophenyl)-1,2-benzisoxazol-6-yl]oxy}acetic acid.

* * * * *